US007189791B2

(12) United States Patent
Solan et al.

(10) Patent No.: US 7,189,791 B2
(45) Date of Patent: Mar. 13, 2007

(54) CATALYST COMPOSITION II

(75) Inventors: Gregory Adam Solan, Leicester (GB); Christopher James Davies, Lancashire (GB)

(73) Assignee: ExxonMobil Chemical Patents Inc., Houston, TX (US)

( * ) Notice: Subject to any disclaimer, the term of this patent is extended or adjusted under 35 U.S.C. 154(b) by 261 days.

(21) Appl. No.: 10/855,585

(22) Filed: May 27, 2004

(65) Prior Publication Data

US 2004/0266961 A1 Dec. 30, 2004

(51) Int. Cl.
*C08F 4/695* (2006.01)
*C08F 4/70* (2006.01)
*B01J 31/12* (2006.01)
*B01J 31/14* (2006.01)
*C07F 13/00* (2006.01)
*C07F 15/00* (2006.01)
*C07F 15/04* (2006.01)

(52) U.S. Cl. ............... 526/175; 526/161; 526/169; 502/103; 502/167; 556/1; 556/45; 556/138

(58) Field of Classification Search ............... 502/167, 502/103; 556/110, 138, 1, 45; 526/169, 526/161, 172
See application file for complete search history.

(56) References Cited

U.S. PATENT DOCUMENTS 6,274,684 B1 * 8/2001 Loveday et al. ............ 526/114
6,809,058 B2 * 10/2004 Boffa et al. ................. 502/167

FOREIGN PATENT DOCUMENTS

| FR | 1 476 587 | 4/1967 | |
|----|-----------|--------|---|
| US | 4008211 | 2/1977 | ............ 260/147 |
| WO | 99/02472 | 1/1999 | |
| WO | 99/12981 | 3/1999 | |
| WO | 00/50470 | 8/2000 | |
| WO | 01/14391 | 3/2001 | |
| WO | 01/83571 | 11/2001 | |
| WO | 03/020778 | 3/2003 | |

OTHER PUBLICATIONS

Kickelbick et al., "Structural Comparison of $Cu^{11}$ complexes in atom transfer radical polymerization", New Journal of Chemistry, (2002) 26(4), 462-468.

Matyjaszewski et al., "Tridentate Nitrogen-Based Ligands in Cu-Based ATRP: A Structure—Activity Study", Macromolecules, 2001, 34, 430-440.

Halfpenny et al., "Structural Effects of Chelate Chain Length in High-Spin Nickel(II) Complexes of Triamines", Inorganica Chimica Acta, 32 (1979) 229-233.

Stebani et al., "Metallomesogens with Branched, Dendrimeric Amino Ligands", Angewandte Chemie, International Edition in English, (1996) 35(16), 1858-1861.

Britovsek et al., "Imine Versus Amine Donors in Iron-Based Ethylene Polymerisation Catalysts", European Journal of Inorganic Chemistry, (2001) (2), 431-437.

B. Elvers et al., Ed. Ullmann's Encyclopedia of Industrial Chemistry, vol. A13, VCH Verlagsgesellschaft mbH, Weinheim, 1989, p. 243-247 and 275-276.

B. Cornils et al., Ed., Applied Homogeneous Catalysis with Organometallic Compounds, A Comprehensive Handbook, vol. 1, VCH Verlagsgesellschaft mbH, Weinheim, 1996, p. 245-258.

B. L. Small and M. Brookhart, Iron-Based Catalysts with Exceptionally High Activities and Selectivities for Oligomerization of Ethylene to Linear α-Olefins, J. Am. Chem. Soc. 1998, 120, 7143.

G. J. P. Britovsek, S. P. D. Baugh, O. Hoarau, V. C. Gibson, D. F. Wass, A. J. P. White, D. J. Williams, The Role of Bulky Substituents in the Polymerization of Ethylene Using Late Transition Metal Catalysts: A Comparative Study of Nickel and Iron Catalyst Systems, Inorg. Chim. Acta 2003, 345, 279.

G. J. P. Britovsek, V. C. Gibson, B. S. Kimberley, S. Mastroianni, C. Redshaw, G. A. Solan, A. J. P. White, D. J. Williams, Bis(imino)pyridyl iron and cobalt complexes: the effect of nitrogen substituents on ethylene oligomerisation and polymerisation, J. Chem. Soc., Dalton Trans. 2001, 1639.

G. J. P. Britovsek, S. Mastroianni, G. A. Solan, S. P. D. Baugh, C. Redshaw, V. C. Gibson, A. J. P. White, D. J. Williams, M. R. J. Elsegood, Oligomerisation of Ethylene by Bis(imino)pyridyliron and -cobalt Complexes, Chem. Eur. J. 2000, 6, 2221.

* cited by examiner

*Primary Examiner*—Caixia Lu
(74) *Attorney, Agent, or Firm*—Catherine L. Bell

(57) ABSTRACT

This invention relates to a transition metal catalyst compound represented by the formula: $LMX_2$ or $(LMX_2)_2$ wherein each M is independently a Group 7 to 11 metal, preferably a Group 7, 8, 9, or 10 metal; each L is, independently, a tridentate or tetradentate neutrally charged ligand that is bonded to M by three or four nitrogen atoms, (where at least one of the nitrogen atoms is a central nitrogen atom and at least two of the nitrogen atoms are terminal nitrogen atoms), and at least two terminal nitrogen atoms are substituted with one $C_3$–$C_{50}$ hydrocarbyl and one hydrogen atom or two hydrocarbyls wherein at least one hydrocarbyl is a $C_3$–$C_{50}$ hydrocarbyl, and the central nitrogen atom is bonded to three different carbon atoms or two different carbon atoms and one hydrogen atom; X is independently a monoanionic ligand, or two X may join together to form a bidentate dianionic ligand.

163 Claims, 3 Drawing Sheets

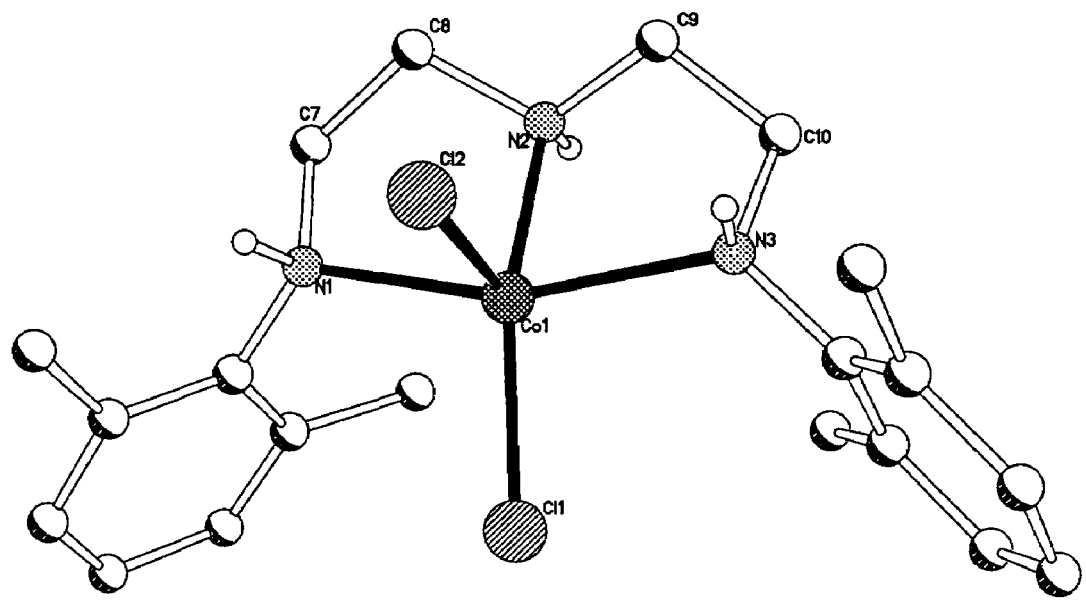
Figure 1 Molecular structure of 3a
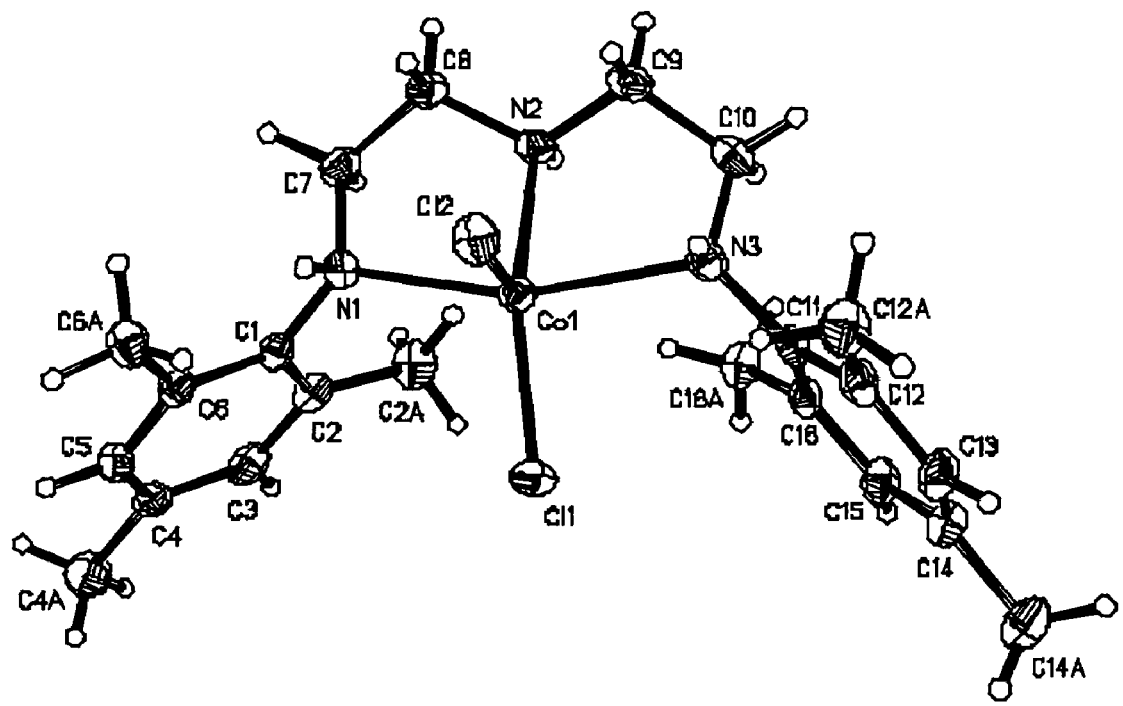
Figure 2 Molecular structure of 3b

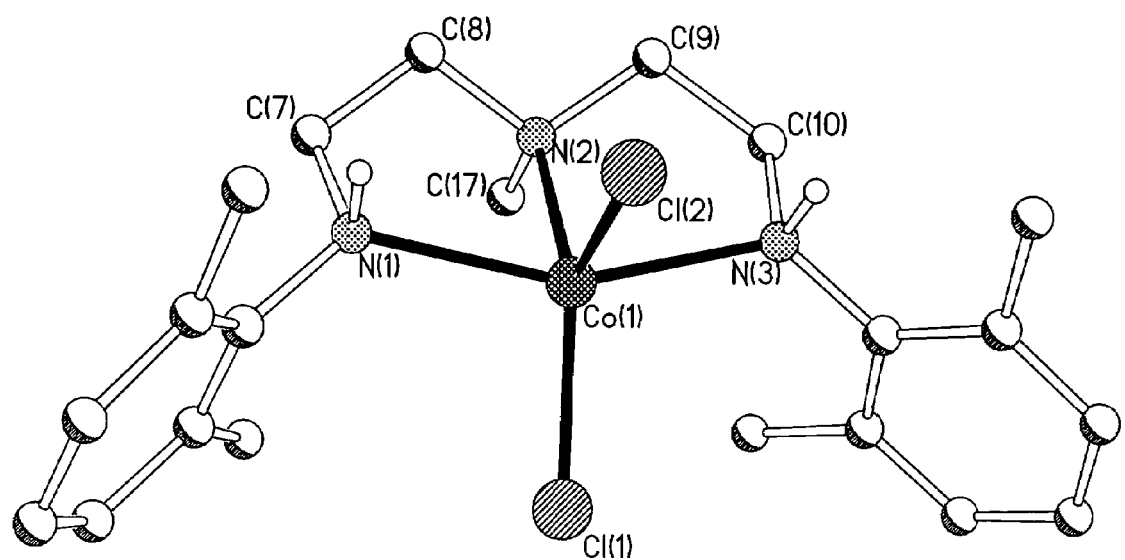
Figure 3 Molecular structure of 3c
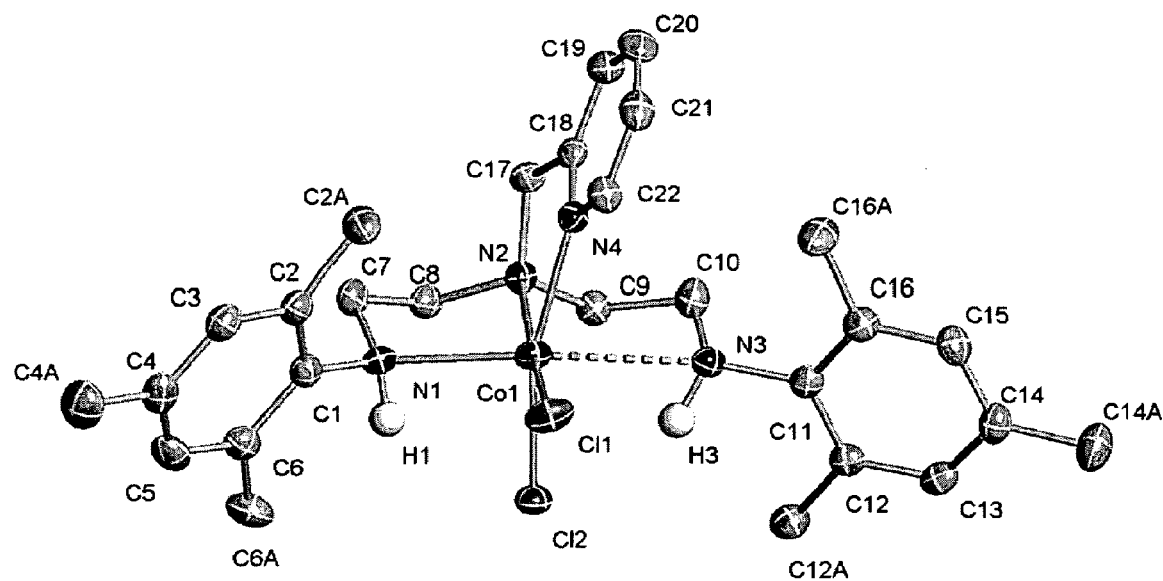
Figure 4 Molecular structure of 4b

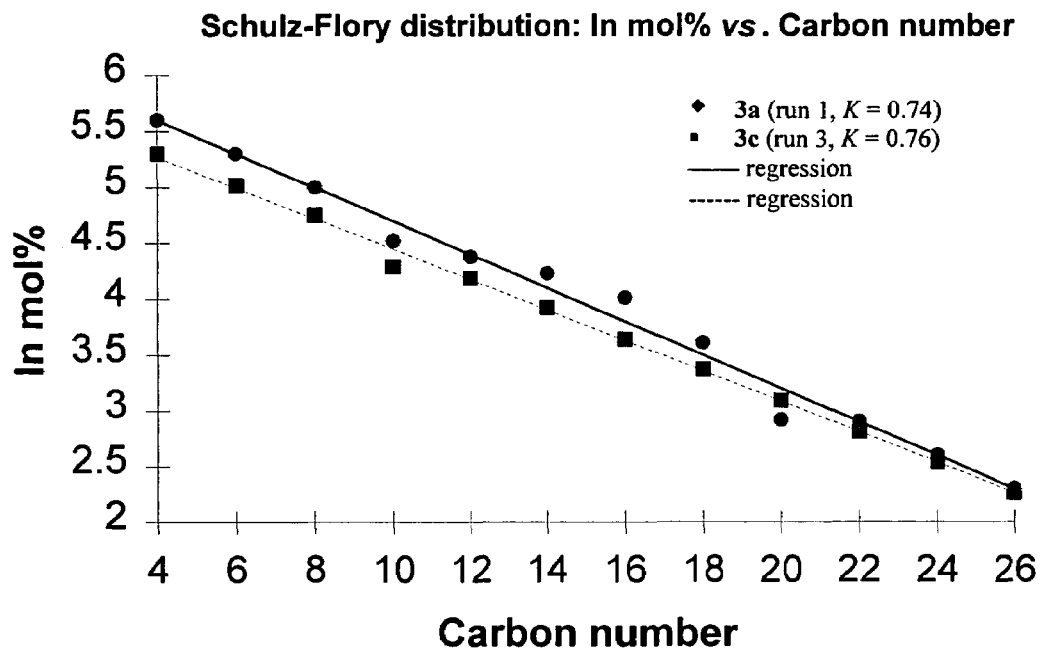
Figure 5  Schulz-Flory distribution for runs 1 and 3 using pre-catalysts, 3a and 3c, respectively.
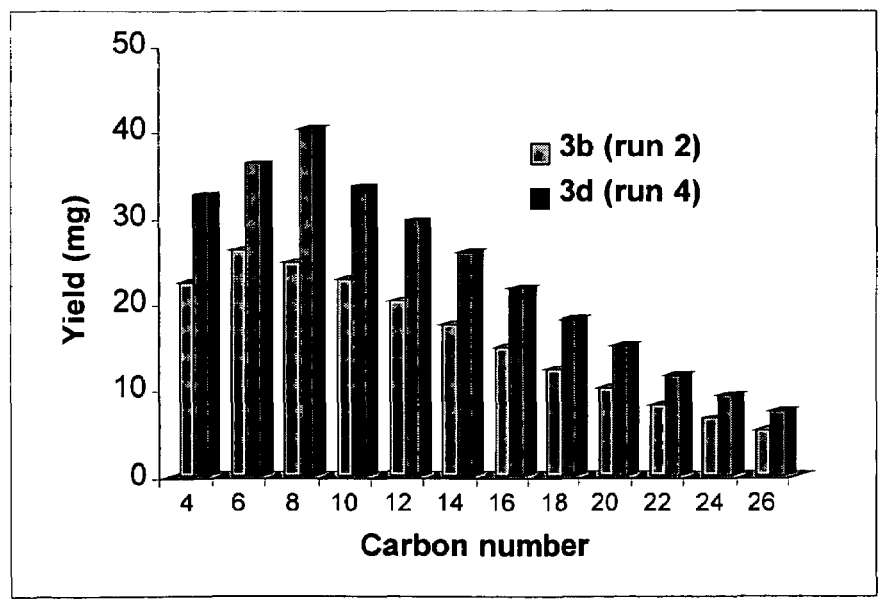
Figure 6  Oligomer distribution of oligomer fractions versus carbon number for runs 2 and 4 using pre-catalysts 3b and 3d, respectively.

CATALYST COMPOSITION II

FIELD OF THE INVENTION

This invention relates to late transition metal catalysts for olefin oligomerization or polymerization and to methods for making and using these catalysts.

BACKGROUND OF THE INVENTION

Olefins, especially those containing 6 to 20 carbon atoms, are important items of commerce. They are used as intermediates in the manufacture of detergents, as monomers (especially in linear low-density polyethylene), and as intermediates for many other types of products. Consequently, improved methods of making these compounds are desired. Especially desired, is a process capable of making a range of linear and branched olefins such as butene, hexene, octene and even higher olefins since as octadecene.

Most commercially produced alpha-olefins are made by the oligomerization of ethylene, catalyzed by various types of compounds, see for instance B. Elvers, et al., Ed. Ullmann's Encyclopedia of Industrial Chemistry, Vol. A13, VCH Verlagsgesellschaft mbH, Weinheim, 1989, p. 243–247 and 275–276, and B. Cornils, et al., Ed., Applied Homogeneous Catalysis with Organometallic Compounds, A Comprehensive Handbook, Vol. 1, VCH Verlagsgesellschaft mbH, Weinheim, 1996, p. 245–258. The major types of commercially used catalysts are alkylaluminum compounds, certain nickel-phosphine complexes, and a titanium halide with a Lewis acid such as $AlCl_3$. In all of these processes, significant amounts of branched internal olefins and diolefins are produced. Since in most instances these are undesirable and often difficult to separate, these byproducts are avoided commercially.

More recently, some iron complexes bearing tridentate chelating bis(imino)pyridine ligands when activated have been reported to produce oligomers (B. L. Small and M. Brookhart, *J. Am. Chem. Soc.* 1998, 120, 7143; M. Brookhart and B. L. Small, PCT Int. Appl. WO9902472, 1999 (DuPont)). Imino-bipyridine based iron complexes when activated produce low molecular weight oligomers (G. J. P. Britovsek, S. D. Baugh, O. Hoarau, V. C. Gibson, D. F. Wass, A. J. P. White, D. J. Williams, *Inorg. Chim. Acta* 2003, 345, 279. Bis(hydrazone)pyridine complexes of iron afford mixtures of low molecular weight polymer and oligomers (G. J. P. Britovsek, V. C. Gibson, B. S. Kimberley, S. Mastroianni, C. Redshaw, G. A. Solan, A. J. P. White, D. J. Williams, *J. Chem. Soc., Dalton Trans.* 2001, 1639; M. O. Kristen, A. Gonioukh, D. Lilge, S. Lehmann, B. Bildstein, C. Amort, M. Malaun PCT Int. Appl. WO0114391, 2001 (BASF); L. S. Moody, P. B. MacKenzie, C. M. Killian, G. G. Lavoie, J. A. Ponasik Jr., T. W. Smith, J. C. Pearson, A. G. M. Barrett, G. W. Coates, PCT Int. Appl. WO0183571, 2001 (Eastman); L. S. Moody, P. B. MacKenzie, C. M. Killian, G. G. Lavoie, J. A. Ponasik Jr., A. G. M. Barrett, T. W. Smith, J. C. Pearson, PCT Int. Appl. WO0050470, 2000 (Eastman)). Iron based oligomerization catalysts have been reported in G. J P. Britovsek, S. Mastroianni, G. A. Solan, S. P. D. Baugh, C. Redshaw, V. C. Gibson, A. J. P. White, D. J. Williams and M. Elsegood, Chem. Eur. J., 2000, 6, 221, and in G. J. Britovsek, B. Dorer, V. C. Gibson, B. S. Kimberley and G. A. Solan, WO9912981, 1999 (BP Chemicals Ltd.).

Hence new oligomerization catalysts are of great interest in the industry because they offer many new opportunities for providing new processes and products to the markets in a cheaper and more efficient manner. The following invention relates to new oligomerization technology based upon new late transition metal catalyst compounds.

SUMMARY OF THE INVENTION

The present invention is directed toward Group 7, 8, 9, 10, or 11 transition metal compounds containing neutral tridentate or tetradentate nitrogen based ligands and an activator that are useful to oligomerize or polymerize olefins, particularly α-olefins, or other unsaturated monomers. For purposes of this disclosure, "α-olefins" includes ethylene.

The oligomerization or polymerization catalysts of this invention comprise transition metal compounds (also referred to as precatalysts or catalyst precursors) represented by the formula: $LMX_2$ or $(LMX_2)_2$ wherein each M is independently a Group 7 to 11 metal, preferably a Group 7, 8, 9, or 10 metal; each L is, independently, a tridentate or tetradentate neutrally charged ligand that is bonded to M by three or four nitrogen atoms, (where at least one of the nitrogen atoms is a central nitrogen atom and at least two of the nitrogen atoms are terminal nitrogen atoms), and at least two terminal nitrogen atoms are substituted with one $C_3$–$C_{50}$ hydrocarbyl and one hydrogen atom or two hydrocarbyls wherein at least one hydrocarbyl is a $C_3$–$C_{50}$ hydrocarbyl, and the central nitrogen atom is bonded to three different carbon atoms or two different carbon atoms and one hydrogen atom; X is independently a monoanionic ligand, or two X may join together to form a bidentate dianionic ligand.

This invention further relates to compositions or transition metal compounds represented by formula 1:

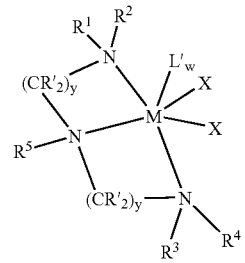

or formula 2:

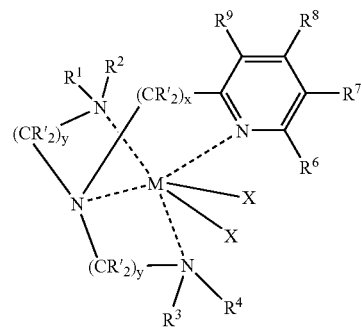

or formula 3:

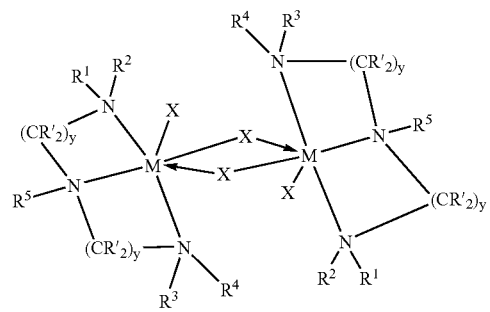

-continued
or formula 4:

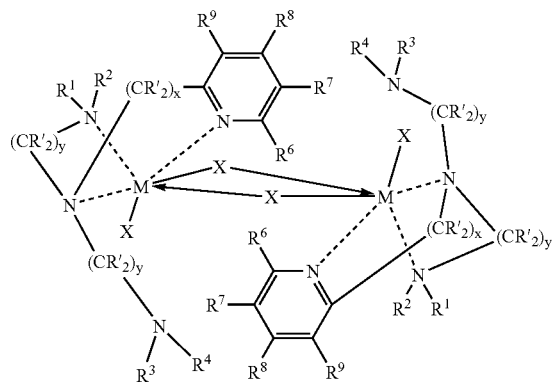

wherein
each M is, independently, a group 7, 8, 9, 10, or 11 transition metal;
N is nitrogen;
C is carbon;
each X is, independently, an anionic monodentate ligand, or both X groups together may form a bidentate dianionic ligand;
each R' is, independently, a hydrogen, a hydrocarbyl, a substituted hydrocarbyl, a halocarbyl, or a substituted halocarbyl; independently, two R' groups on the same carbon may join to form a cyclic or polycyclic ring structure; when x is 2, 3, or 4, and or when y is 2, 3, or 4, two or more R' groups on adjacent carbon atoms may join to form a cyclic or polycyclic ring structure;
each x is, independently, 1, 2, 3 or 4;
each y is, independently, 1, 2, 3 or 4;
each $R^1$ or $R^3$ is, independently, a hydrogen, hydrocarbyl or halocarbyl;
each $R^2$ or $R^4$ is, independently, a $C_3$ to $C_{50}$ hydrocarbyl or a $C_3$ to $C_{50}$ halocarbyl;
each $R^5$ is, independently, hydrogen, a hydrocarbyl, a substituted hydrocarbyl, a halocarbyl, or a substituted halocarbyl; optionally $R^5$ may be bonded to M through the heteroatom of a substituted hydrocarbyl, or a substituted halocarbyl;
each $R^6$, $R^7$, $R^8$, or $R^9$ is, independently, a hydrogen, a hydrocarbyl, a substituted a hydrocarbyl, a halocarbyl, or a substituted halocarbyl, or independently, two adjacent $R^6$, $R^7$, $R^8$, or $R^9$ may join together to form a cyclic or polycyclic ring structure;
L' is a neutral ligand bonded to M;
and w is 0 or 1.

This invention further relates to a process to oligomerize or polymerize an unsaturated monomer using the compositions (compounds) of formulae 1–4 described herein.

BRIEF DESCRIPTION OF THE DRAWINGS

FIG. 1 represents the molecular structure of 3a.
FIG. 2 represents the molecular structure of 3b.
FIG. 3 represents the molecular structure of 3c.
FIG. 4 represents the molecular structure of 4b.
FIG. 5 is a plot of carbon number vs. In mol % and represents the Schulz-Flory distribution for runs 1 and 3 using pre-catalysts, 3a and 3c, respectively.

FIG. 6 show the oligomer distribution of oligomer fractions versus carbon number for runs 2 and 4 using pre-catalysts 3b and 3d, respectively.

DEFINITIONS

As used herein, the new numbering scheme for the Periodic Table Groups are used as in CHEMICAL AND ENGINEERING NEWS, 63(5), 27 (1985).

For the purposes of this invention and the claims thereto and for ease of reference when a polymer is referred to as comprising an olefin, the olefin present in the polymer is the polymerized form of the olefin. Likewise when catalyst components are described as comprising neutral stable forms of the components, it is well understood by one of ordinary skill in the art, that the ionic form of the component is the form that reacts with the monomers to produce polymers. In the description herein the transition metal catalyst compound may be described as a catalyst precursor, a pre-catalyst compound or a catalyst compound, and these terms are used interchangeably. A catalyst system is a combination of a transition metal catalyst compound and an activator. An activator is also interchangeably referred to as a cocatalyst.

The term "hydrocarbyl radical" is sometimes used interchangeably with "hydrocarbyl" throughout this document. For purposes of this disclosure, "hydrocarbyl radical" encompasses $C_1$–$C_{50}$ radicals. These radicals can be linear, branched, or cyclic including polycyclic. These radicals can be saturated, partially unsaturated or fully unsaturated, and when cyclic, may be aromatic or non-aromatic.

In describing a ligand, a terminal nitrogen atom, is a nitrogen atom that is indirectly bonded to only one other nitrogen atom. A central nitrogen atom is a nitrogen atom that is indirectly bonded to two or more other nitrogen atoms. An example is illustrated below:

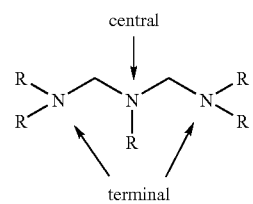

Substituted hydrocarbyl radicals are radicals in which at least one hydrogen atom has been replaced with a heteroatom or with at least one functional group such as $NR''_2$, $OR''$, $PR''_2$, $SR''$, $BR''_2$, $SiR''_3$, $GeR''_3$ and the like or where at least one non-hydrocarbon atom or group has been inserted within the hydrocarbyl radical, such as O, S, $NR''$, $PR''$, $BR''$, $SiR''_2$, $GeR''_2$, and the like, where $R''$ is independently a hydrocarbyl or halocarbyl radical. The functional group can be an organometalloid radical.

Halocarbyl radicals are radicals in which one or more hydrocarbyl hydrogen atoms have been substituted with at least one halogen or halogen-containing group (e.g. F, Cl, Br, I).

Substituted halocarbyl radicals are radicals in which at least one hydrocarbyl hydrogen or halogen atom has been substituted with at least one functional group such as $NR''_2$, $OR''$, $PR''_2$, $SR''$, $BR''_2$, $SiR''_3$, $GeR''_3$ and the like or where at least one non-carbon atom or group has been inserted within the halocarbyl radical such as O, S, $NR''$, $PR''$, $BR''$, $SiR''_2$, $GeR''_2$, and the like where $R''$ is independently a hydrocarbyl or halocarbyl radical provided that at least one halogen atom remains on the original halocarbyl radical. The functional group can be an organometalloid radical.

In some embodiments, the hydrocarbyl radical is independently selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, or triacontynyl isomers. For this disclosure, when a radical is listed it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

For purposes of this disclosure, the term oligomer refers to compositions having 2–75 mer units and the term polymer refers to compositions having 76 or more mer units. A mer is defined as a unit of an oligomer or polymer that originally corresponded to the olefin(s) used in the oligomerization or polymerization reaction. For example, the mer of polyethylene would be ethylene.

Anionic monodentate ligands, also called abstractable ligands, are ligands that are removed from the catalyst precursor to activate it. They are sometimes assigned the label X in this disclosure. X are independently hydride radicals, hydrocarbyl radicals, or hydrocarbyl-substituted organometalloid radicals; or two X's are connected and form a 3-to-50-atom metallacycle ring. Specifically, this metallacycle ring could take the form of a bidentate dianionic ligand.

When Lewis-acid activators such as methylalumoxane, aluminum alkyls, alkylaluminum alkoxides or alkylaluminum halides that are capable of donating an X ligand, as described above, to the transition metal component are used, or when the ionic activator is capable of extracting X, one or more X, which may optionally be bridged to one another, may additionally be independently selected from a halogen, alkoxide, aryloxide, amide, phosphide or other anionic ligand, provided that the resulting activated catalyst contains as least one M-H or M-C connection in which an olefin can insert.

When the pre-catalysts of this invention are drawn as dimeric species, two X may be independently a monoanionic bridging ligand that is bonded to each M (e.g. μ-X).

In some structures throughout this specification the ligand-metal connection is drawn with an arrow indicating that the electrons originally came from the ligand. At other times, the connection is shown by drawing a solid or dashed line. One of ordinary skill in the art recognizes that these depictions are interchangeable.

Alicyclic rings are aliphatic radicals that have a ring or cyclic structure in which the ring portion may be saturated or unsaturated, but in which the ring portion may not be aromatic. One of ordinary skill in the art recognizes that alicyclic, as defined in this document, is a subset of hydrocarbyl, as defined in this document.

DETAILED DESCRIPTION OF THE INVENTION

This invention further relates to compositions or transition metal compounds represented by formula 1:

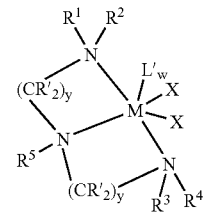

or formula 2:

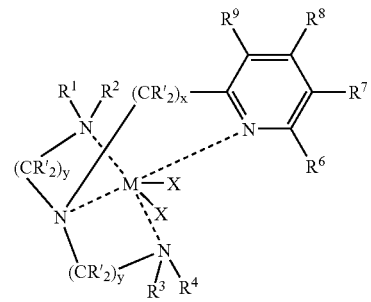

or formula 3:

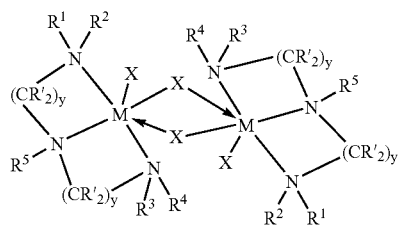

or formula 4:

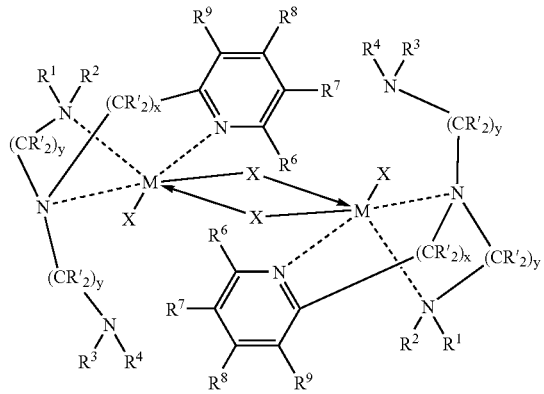

wherein
each M is, independently, a group 7, 8, 9, 10, or 11 transition metal, preferably a group 7, 8, 9 or 10 transition metal, preferably nickel, cobalt, iron or manganese;

N is nitrogen;

C is carbon;

each X is, independently, a hydride, hydrocarbyl, substituted hydrocarbyl, halocarbyl, substituted halocarbyl or both X groups together are a hydrocarbdiyl, halocarbdiyl, substituted hydrocarbdiyl, or substituted halocarbdiyl;

additionally, X may independently be selected from halogen, alkoxide, aryloxide, amide, phosphide, or other anionic ligand when Lewis-acid activators (such as methylalumoxane, aluminum alkyls, alkylaluminum alkoxides) or alkylaluminum halides (capable of donating a hydride, hydrocarbyl, substituted hydrocarbyl, halocarbyl or substituted halocarbyl X ligand to the transition metal component) are used, or when an ionic activator is capable of extracting X, provided that the resulting activated catalyst contains as least one M-H or M-C bond into which an olefin can insert (Note that one or more X may optionally bridge to one another, as well), preferably X is selected from the group consisting of chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, methoxy, ethoxy, propoxy, butoxy, dimethylamido, diethylamido, methylethylamido, phenoxy, benzoxy, and allyl, even more preferably two X groups are joined and are selected from the group consisting of methylidene, ethylidene, propylidene, tetramethylene, pentamethylene, hexamethylene, butadiene, methylbutadiene, dimethylbutadiene, pentadiene, methylpentadiene, dimethylpentadiene, hexadiene, methylhexadiene, and dimethylhexadiene;

each R' is, independently, a hydrogen, or a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl, independently, two R' groups on the same carbon may join to form a $C_3$ to $C_{61}$ cyclic or polycyclic ring structure; when x is 2, 3, or 4, and or when y is 2, 3, or 4, two or more R' groups on adjacent carbon atoms may join to form a $C_4$ to $C_{62}$ cyclic or polycyclic ring structure;

x is, independently, 1, 2, 3 or 4, preferably, x is 1;

y is, independently, 1, 2, 3 or 4, preferably, y is 2;

each $R^1$ or $R^3$ are, independently, a hydrogen, or a hydrocarbyl, or a halocarbyl, preferably a $C_1$ to $C_{30}$ hydrocarbyl, or a $C_1$ to $C_{30}$ halocarbyl, more preferably a $C_1$ to $C_{10}$ hydrocarbyl, or a $C_1$ to $C_{10}$ halocarbyl;

each $R^2$ or $R^4$ are, independently, a $C_3$ to $C_{50}$ hydrocarbyl, or a $C_3$ to $C_{50}$ halocarbyl, preferably a $C_3$ to $C_{30}$ hydrocarbyl, or a $C_3$ to $C_{30}$ halocarbyl, more preferably a $C_3$ to $C_{20}$ hydrocarbyl, or a $C_3$ to $C_{20}$ halocarbyl;

each $R^5$ is, independently, a hydrogen, or a hydrocarbyl, a substituted hydrocarbyl, a halocarbyl, or a substituted halocarbyl, preferably a $C_1$ to $C_{30}$ hydrocarbyl, a $C_1$ to $C_{30}$ substituted hydrocarbyl, a $C_1$ to $C_{30}$ halocarbyl or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl or a $C_1$ to $C_{10}$ substituted halocarbyl; optionally $R^5$ may be bound to M through the heteroatom of a substituted hydrocarbyl, or a substituted halocarbyl;

each $R^6$, $R^7$, $R^8$, or $R^9$ is, independently, a hydrogen, or a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl, or independently, one or more adjacent $R^6$, $R^7$, $R^8$, or $R^9$ may join to form a cyclic or polycyclic ring structure; $R^6$ is preferably selected from the group consisting of methyl, ethyl, and all linear and cyclic isomers of propyl, butyl, pentyl, hexyl, heptyl, octyl, nonyl, decyl, undecyl, dodecyl, phenyl, dimethylphenyl, diethylphenyl, dipropylphenyl, naphthyl, anthracenyl, and other substituents; $R^6$ is even more preferably, methyl, ethyl, isopropyl, tert-butyl, neopentyl, cyclohexyl, phenyl, 2,6-dimethylphenyl, 2,6-diisopropylphenyl, 2,5-di-tert-butylphenyl, naphthyl, anthracenyl, adamantyl, and norbornyl;

L' is a neutral ligand bonded to M and includes molecules such as but not limited to diethyl ether, tetrahydrofuran, dimethylaniline, trimethylamine, tributylamine, trimethylphosphine, triphenylphosphine lithium chloride, ethylene, propylene, butene, octene, styrene, and the like;

w is 0 or 1 and indicates the absence or presence of L';

and where preferred halocarbyls are fluorocarbyls.

In another preferred embodiment, this invention further relates to compositions represented by the formula 5:

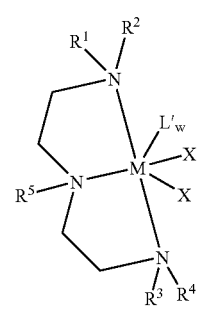

or formula 6:

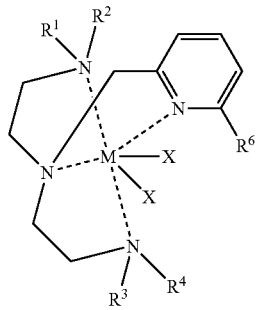

or formula 7:

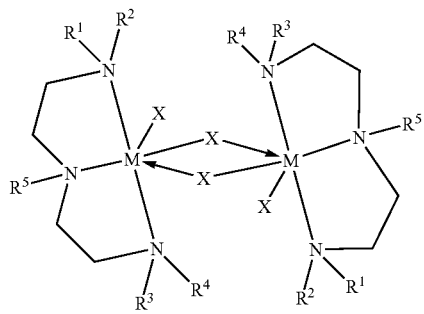

or formula 8:

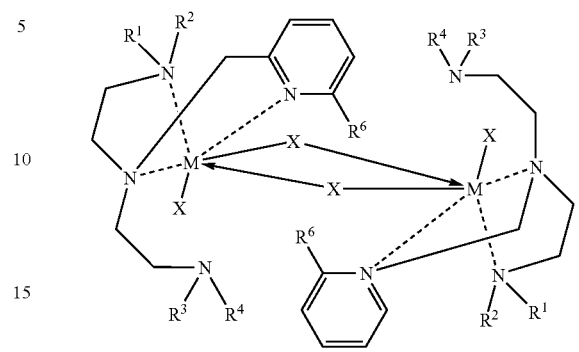

wherein

M, N, $R^1$, $R^2$, $R^3$, $R^4$, $R^5$, $R^6$, X, L' and w are as previously defined.

To illustrate members of the transition metal catalyst compounds useful in this invention, select any combination of the species listed in Table 1.

| $R^2$, $R^4$ | $R^1$, $R^3$, $R^5$, R', $R^6$, $R^7$, $R^8$, $R^9$ | X | M | L' |
|---|---|---|---|---|
| propyl | hydrogen | chloride | cobalt | diethyl ether |
| butyl | methyl | bromide | manganese | tetrahydrofuran |
| pentyl | ethyl | iodide | iron | furan |
| hexyl | propyl | methyl | nickel | thiofuran |
| heptyl | butyl | ethyl | copper | chromane |
| octyl | pentyl | propyl | technetium | isochromane |
| nonyl | hexyl | butyl | rhenium | thiochromane |
| decyl | heptyl | pentyl | ruthenium | thioisochromane |
| undecyl | octyl | hexyl | osmium | quinuclidine |
| dodecyl | nonyl | heptyl | rhodium | benzofuran |
| tridecyl | decyl | octyl | iridium | chromene |
| tetradecyl | undecyl | nonyl | palladium | isobenzofuran |
| octacosyl | dodecyl | decyl | platinum | isoquinoline |
| nonacosyl | tridecyl | undecyl | silver | oxazole |
| triacontyl | tetradecyl | dodecyl | gold | phenanthridine |
| cyclohexyl | octacosyl | tridecyl | | pyran |
| cyclopentyl | nonacosyl | tetradecyl | | pyridine |
| cycloheptyl | triacontyl | pentadecyl | | quinoline |
| cyclooctyl | cyclohexyl | hexadecyl | | selenophene |
| cyclodecyl | cyclopentyl | heptadecyl | | thiophene |
| cyclododecyl | cycloheptyl | octadecyl | | trimethylamine |
| naphthyl | cyclooctyl | nonadecyl | | triethylamine |
| phenyl | cyclodecyl | eicosyl | | tributylamine |
| tolyl | cyclododecyl | heneicosyl | | dimethylaniline |
| benzyl | naphthyl | docosyl | | trimethylphosphine |
| phenethyl | phenyl | tricosyl | | triphenylphosphine |
| dimethylphenyl | tolyl | tetracosyl | | ethylene |
| trimethylphenyl | benzyl | pentacosyl | | propylene |
| methylphenyl | phenethyl | hexacosyl | | butene |
| ethylphenyl | anthracenyl | heptacosyl | | hexene |
| diethylphenyl | dimethylphenyl | octacosyl | | octene |
| triethylphenyl | diethylphenyl | nonacosyl | | cyclohexene |
| propylphenyl | dipropylphenyl | triacontyl | | vinylcyclohexene |
| dipropylphenyl | dibutylphenyl | hydride | | benzene |

-continued

| .R², R⁴ | R¹, R³, R⁵, R', R⁶, R⁷, R⁸, R⁹ | | M | L' |
|---|---|---|---|---|
| tripropylphenyl | norbornyl | phenyl | | styrene |
| methylethylphenyl | adamantyl | benzyl | | methylstyrene |
| dibutylphenyl | | phenethyl | | lithium chloride |
| butylphenyl | | tolyl | | ammonium chloride |
| | | methoxy | | |
| | | ethoxy | | |
| | | propoxy | | |
| | | butoxy | | |
| | | dimethylamido | | |
| | | diethylamido | | |
| | | methylethylamido | | |
| | | phenoxy | | |
| | | benzoxy | | |
| | | allyl | | |
| | | <u>Both X joined</u> | | |
| | | methylidene | | |
| | | ethylidene | | |
| | | propylidene | | |
| | | tetramethylene | | |
| | | pentamethylene | | |
| | | hexamethylene | | |
| | | butadiene | | |
| | | methylbutadiene | | |
| | | dimethylbutadiene | | |
| | | pentadiene | | |
| | | methylpentadiene | | |
| | | dimethylpentadiene | | |
| | | hexadiene | | |
| | | methylhexadiene | | |
| | | dimethylhexadiene | | |

Preferred transition metal catalyst compounds include:
[bis(N-2,6-dimethylphenyl-2-aminoethyl)amine]cobalt dichloride,
[bis(N-2,4,6-trimethylphenyl-2-aminoethyl)amine]cobalt dichloride,
[bis(N-2,6-diisopropylphenyl-2-aminoethyl)amine]cobalt dichloride,
[bis(N-2,4,6-triisopropylphenyl-2-aminoethyl)amine]cobalt dichloride,
[bis(N-2,6-diisopropyl-4-methylphenyl-2-aminoethyl)amine]cobalt dichloride,
[bis(N-2,6-diethylphenyl-2-aminoethyl)amine]cobalt dichloride,
[bis(N-2,4,6-triethylphenyl-2-aminoethyl)amine]cobalt dichloride,
[bis(N-2,6-dimethylphenyl-2-aminomethyl)amine]cobalt dichloride,
[bis(N-2,4,6-trimethylphenyl-2-aminomethyl)amine]cobalt dichloride,
[bis(N-2,6-diisopropylphenyl-2-aminomethyl)amine]cobalt dichloride,
[bis(N-2,4,6-triisopropylphenyl-2-aminomethyl)amine]cobalt dichloride,
[bis(N-2,6-diisopropyl-4-methylphenyl-2-aminomethyl)amine]cobalt dichloride,
[bis(N-2,6-diethylphenyl-2-aminomethyl)amine]cobalt dichloride,
[bis(N-2,4,6-triethylphenyl-2-aminomethyl)amine]cobalt dichloride,
[bis(N-2,6-dimethylphenyl-2-aminopropyl)amine]cobalt dichloride,
[bis(N-2,4,6-trimethylphenyl-2-aminopropyl)amine]cobalt dichloride,
[bis(N-2,6-diisopropylphenyl-2-aminopropyl)amine]cobalt dichloride,
[bis(N-2,4,6-triisopropylphenyl-2-aminopropyl)amine]cobalt dichloride,
[bis(N-2,6-diisopropyl-4-methylphenyl-2-aminopropyl)amine]cobalt dichloride,
[bis(N-2,6-diethylphenyl-2-aminopropyl)amine]cobalt dichloride,
[bis(N-2,4,6-triethylphenyl-2-aminopropyl)amine]cobalt dichloride,
[bis(N-2,6-dimethylphenyl-3-aminopropyl)amine]cobalt dichloride,
[bis(N-2,4,6-trimethylphenyl-3-aminopropyl)amine]cobalt dichloride,
[bis(N-2,6-diisopropylphenyl-3-aminopropyl)amine]cobalt dichloride,
[bis(N-2,4,6-triisopropylphenyl-3-aminopropyl)amine]cobalt dichloride,
[bis(N-2,6-diisopropyl-4-methylphenyl-3-aminopropyl)amine]cobalt dichloride,
[bis(N-2,6-diethylphenyl-3-aminopropyl)amine]cobalt dichloride,
[bis(N-2,4,6-triethylphenyl-3-aminopropyl)amine]cobalt dichloride,
[(N-2,6-dimethylphenyl-2-aminoethyl)(N-2,6-dimethylphenyl-3-aminopropyl)amine]cobalt dichloride,
[(N-2,4,6-trimethylphenyl-2-aminoethyl)(N-2,4,6-trimethylphenyl-3-aminopropyl)amine]cobalt dichloride,
[(N-2,6-diisopropylphenyl-2-aminoethyl)(N-2,6-diisopropylphenyl-3-aminopropyl)amine]cobalt dichloride,
[(N-2,4,6-triisopropylphenyl-2-aminoethyl)(N-2,4,6-triisopropylphenyl-3-aminopropyl)amine]cobalt dichloride,

[(N-2,6-diisopropyl-4-methylphenyl-2-aminoethyl)(N-2,6-diisopropyl-4-methylphenyl-3-aminopropyl)amine]cobalt dichloride,
[(N-2,6-diethylphenyl-2-aminoethyl)(N-2,6-diethylphenyl-3-aminopropyl)amine]cobalt dichloride,
[(N-2,4,6-triethylphenyl-2-aminoethyl)(N-2,4,6-triethylphenyl-3-aminopropyl)amine]cobalt dichloride,
[(N-2,6-dimethylphenyl-2-aminoethyl)(N-2,6-dimethylphenyl-3-aminomethyl)amine]cobalt dichloride,
[(N-2,4,6-trimethylphenyl-2-aminoethyl)(N-2,4,6-trimethylphenyl-3-aminomethyl)amine]cobalt dichloride,
[(N-2,6-diisopropylphenyl-2-aminoethyl)(N-2,6-diisopropylphenyl-3-aminomethyl)amine]cobalt dichloride,
[(N-2,4,6-triisopropylphenyl-2-aminoethyl)(N-2,4,6-triisopropylphenyl-3-aminomethyl)amine]cobalt dichloride,
[(N-2,6-diisopropyl-4-methylphenyl-2-aminoethyl)(N-2,6-diisopropyl-4-methylphenyl-3-aminomethyl)amine]cobalt dichloride,
[(N-2,6-diethylphenyl-2-aminoethyl)(N-2,6-diethylphenyl-3-aminomethyl)amine]cobalt dichloride,
[(N-2,4,6-triethylphenyl-2-aminoethyl)(N-2,4,6-triethylphenyl-3-aminomethyl)amine]cobalt dichloride,
[(N-2,6-dimethylphenyl-2-aminoethyl)(N-2,4,6-trimethylphenyl-2-aminoethyl)amine]cobalt dichloride,
[(N-2,6-dimethylphenyl-2-aminoethyl)(N-2,6-diisopropylphenyl-2-aminoethyl)amine]cobalt dichloride,
[(N-2,6-dimethylphenyl-2-aminoethyl)(N-2,4,6-triisopropylphenyl-2-aminoethyl)amine]cobalt dichloride,
[(N-2,6-dimethylphenyl-2-aminoethyl)(N-2,6-diisopropyl-4-methylphenyl-2-aminoethyl)amine]cobalt dichloride,
[(N-2,6-dimethylphenyl-2-aminoethyl)(N-2,6-diethylphenyl-2-aminoethyl)amine]cobalt dichloride,
[(N-2,6-dimethylphenyl-2-aminoethyl)(N-2,4,6-triethylphenyl-2-aminoethyl)amine]cobalt dichloride,
[(N-2,4,6-trimethylphenyl-2-aminoethyl)(N-2,6-diisopropylphenyl-2-aminoethyl)amine]cobalt dichloride,
[(N-2,4,6-trimethylphenyl-2-aminoethyl)(N-2,4,6-triisopropylphenyl-2-aminoethyl)amine]cobalt dichloride,
[(N-2,4,6-trimethylphenyl-2-aminoethyl)(N-2,6-diisopropyl-4-methylphenyl-2-aminoethyl)amine]cobalt dichloride,
[(N-2,4,6-trimethylphenyl-2-aminoethyl)(N-2,6-diethylphenyl-2-aminoethyl)amine]cobalt dichloride,
[(N-2,4,6-trimethylphenyl-2-aminoethyl)(N-2,4,6-triethylphenyl-2-aminoethyl)amine]cobalt dichloride,
[bis(N-2,6-dimethylphenyl-2-aminoethyl)(2-picolyl)amine]cobalt dichloride,
[bis(N-2,4,6-trimethylphenyl-2-aminoethyl)(2-picolyl)amine]cobalt dichloride,
[bis(N-2,6-diisopropylphenyl-2-aminoethyl)(2-picolyl)amine]cobalt dichloride,
[bis(N-2,4,6-triisopropylphenyl-2-aminoethyl)(2-picolyl)amine]cobalt dichloride,
[bis(N-2,6-diisopropyl-4-methylphenyl-2-aminoethyl)(2-picolyl)amine]cobalt dichloride,
[bis(N-2,6-diethylphenyl-2-aminoethyl)(2-picolyl)amine]cobalt dichloride,
[bis(N-2,4,6-triethylphenyl-2-aminoethyl)(2-picolyl)amine]cobalt dichloride,
[bis(N-2,6-dimethylphenyl-2-aminomethyl)(2-picolyl)amine]cobalt dichloride,
[bis(N-2,4,6-trimethylphenyl-2-aminomethyl)(2-picolyl)amine]cobalt dichloride,
[bis(N-2,6-diisopropylphenyl-2-aminomethyl)(2-picolyl)amine]cobalt dichloride,
[bis(N-2,4,6-triisopropylphenyl-2-aminomethyl)(2-picolyl)amine]cobalt dichloride,
[bis(N-2,6-diisopropyl-4-methylphenyl-2-aminomethyl)(2-picolyl)amine]cobalt dichloride,
[bis(N-2,6-diethylphenyl-2-aminomethyl)(2-picolyl)amine]cobalt dichloride,
[bis(N-2,4,6-triethylphenyl-2-aminomethyl)(2-picolyl)amine]cobalt dichloride,
[bis(N-2,6-dimethylphenyl-2-aminopropyl)(2-picolyl)amine]cobalt dichloride,
[bis(N-2,4,6-trimethylphenyl-2-aminopropyl)(2-picolyl)amine]cobalt dichloride,
[bis(N-2,6-diisopropylphenyl-2-aminopropyl)(2-picolyl)amine]cobalt dichloride,
[bis(N-2,4,6-triisopropylphenyl-2-aminopropyl)(2-picolyl)amine]cobalt dichloride,
[bis(N-2,6-diisopropyl-4-methylphenyl-2-aminopropyl)(2-picolyl)amine]cobalt dichloride,
[bis(N-2,6-diethylphenyl-2-aminopropyl)(2-picolyl)amine]cobalt dichloride,
[bis(N-2,4,6-triethylphenyl-2-aminopropyl)(2-picolyl)amine]cobalt dichloride,
[bis(N-2,6-dimethylphenyl-3-aminopropyl)(2-picolyl)amine]cobalt dichloride,
[bis(N-2,4,6-trimethylphenyl-3-aminopropyl)(2-picolyl)amine]cobalt dichloride,
[bis(N-2,6-diisopropylphenyl-3-aminopropyl)(2-picolyl)amine]cobalt dichloride,
[bis(N-2,4,6-triisopropylphenyl-3-aminopropyl)(2-picolyl)amine]cobalt dichloride,
[bis(N-2,6-diisopropyl-4-methylphenyl-3-aminopropyl)(2-picolyl)amine]cobalt dichloride,
[bis(N-2,6-diethylphenyl-3-aminopropyl)(2-picolyl)amine]cobalt dichloride,
[bis(N-2,4,6-triethylphenyl-3-aminopropyl)(2-picolyl)amine]cobalt dichloride,
[(N-2,6-dimethylphenyl-2-aminoethyl)(N-2,6-dimethylphenyl-3-aminopropyl)(2-picolyl)amine]cobalt dichloride,
[(N-2,4,6-trimethylphenyl-2-aminoethyl)(N-2,4,6-trimethylphenyl-3-aminopropyl)(2-picolyl)amine]cobalt dichloride,
[(N-2,6-diisopropylphenyl-2-aminoethyl)(N-2,6-diisopropylphenyl-3-aminopropyl)(2-picolyl)amine]cobalt dichloride,
[(N-2,4,6-triisopropylphenyl-2-aminoethyl)(N-2,4,6-triisopropylphenyl-3-aminopropyl)(2-picolyl)amine]cobalt dichloride,
[(N-2,6-diisopropyl-4-methylphenyl-2-aminoethyl)(N-2,6-diisopropyl-4-methylphenyl-3-aminopropyl)(2-picolyl)amine]cobalt dichloride,
[(N-2,6-diethylphenyl-2-aminoethyl)(N-2,6-diethylphenyl-3-aminopropyl)(2-picolyl)amine]cobalt dichloride,
[(N-2,4,6-triethylphenyl-2-aminoethyl)(N-2,4,6-triethylphenyl-3-aminopropyl)(2-picolyl)amine]cobalt dichloride,
[(N-2,6-dimethylphenyl-2-aminoethyl)(N-2,6-dimethylphenyl-3-aminomethyl)(2-picolyl)amine]cobalt dichloride,
[(N-2,4,6-trimethylphenyl-2-aminoethyl)(N-2,4,6-trimethylphenyl-3-aminomethyl)(2-picolyl)amine]cobalt dichloride,
[(N-2,6-diisopropylphenyl-2-aminoethyl)(N-2,6-diisopropylphenyl-3-aminomethyl)(2-picolyl)amine]cobalt dichloride,
[(N-2,4,6-triisopropylphenyl-2-aminoethyl)(N-2,4,6-triisopropylphenyl-3-aminomethyl)(2-picolyl)amine]cobalt dichloride,
[(N-2,6-diisopropyl-4-methylphenyl-2-aminoethyl)(N-2,6-diisopropyl-4-methylphenyl-3-aminomethyl)(2-picolyl)amine]cobalt dichloride,

[(N-2,6-diethylphenyl-2-aminoethyl)(N-2,6-diethylphenyl-3-aminomethyl)(2-picolyl)amine]cobalt dichloride,
[(N-2,4,6-triethylphenyl-2-aminoethyl)(N-2,4,6-triethylphenyl-3-aminomethyl)(2-picolyl)amine]cobalt dichloride,
[(N-2,6-dimethylphenyl-2-amino ethyl) (N-2,4,6-trimethylphenyl-2-amino ethyl)(2-picolyl)amine]cobalt dichloride,
[(N-2,6-dimethylphenyl-2-aminoethyl)(N-2,6-diisopropylphenyl-2-aminoethyl)(2-picolyl)amine]cobalt dichloride,
[(N-2,6-dimethylphenyl-2-aminoethyl)(N-2,4,6-triisopropylphenyl-2-aminoethyl)(2-picolyl)amine]cobalt dichloride,
[(N-2,6-dimethylphenyl-2-aminoethyl)(N-2,6-diisopropyl-4-methylphenyl-2-aminoethyl)(2-picolyl)amine]cobalt dichloride,
[(N-2,6-dimethylphenyl-2-aminoethyl)(N-2,6-diethylphenyl-2-aminoethyl)(2-picolyl)amine]cobalt dichloride,
[[(N-2,6-dimethylphenyl-2-aminoethyl)((N-2,4,6-triethylphenyl-2-aminoethyl)(2-picolyl)amine]cobalt dichloride,
[(N-2,4,6-trimethylphenyl-2-aminoethyl)(N-2,6-diisopropylphenyl-2-aminoethyl)(2-picolyl)amine]cobalt dichloride,
[(N-2,4,6-trimethylphenyl-2-aminoethyl)(N-2,4,6-triisopropylphenyl-2-aminoethyl)(2-picolyl)amine]cobalt dichloride,
[(N-2,4,6-trimethylphenyl-2-aminoethyl)(N-2,6-diisopropyl-4-methylphenyl-2-aminoethyl)(2-picolyl)amine]cobalt dichloride,
[(N-2,4,6-trimethylphenyl-2-aminoethyl)(N-2,6-diethylphenyl-2-aminoethyl)(2-picolyl)amine]cobalt dichloride,
[(N-2,4,6-trimethylphenyl-2-aminoethyl)(N-2,4,6-triethylphenyl-2-aminoethyl)(2-picolyl)amine]cobalt dichloride,
[bis(N-2,6-dimethylphenyl-2-aminoethyl)methylamine]cobalt dichloride,
[bis(N-2,4,6-trimethylphenyl-2-aminoethyl)methylamine]cobalt dichloride,
[bis(N-2,6-diisopropylphenyl-2-aminoethyl)methylamine]cobalt dichloride,
[bis(N-2,4,6-triisopropylphenyl-2-aminoethyl)methylamine]cobalt dichloride,
[bis(N-2,6-diisopropyl-4-methylphenyl-2-aminoethyl)methylamine]cobalt dichloride,
[bis(N-2,6-diethylphenyl-2-aminoethyl)methylamine]cobalt dichloride,
[bis(N-2,4,6-triethylphenyl-2-aminoethyl)methylamine]cobalt dichloride,
[bis(N-2,6-dimethylphenyl-2-aminomethyl)methylamine]cobalt dichloride,
[bis(N-2,4,6-trimethylphenyl-2-aminomethyl)methylamine]cobalt dichloride,
[bis(N-2,6-diisopropylphenyl-2-aminomethyl)methylamine]cobalt dichloride,
[bis(N-2,4,6-triisopropylphenyl-2-aminomethyl)methylamine]cobalt dichloride,
[bis(N-2,6-diisopropyl-4-methylphenyl-2-aminomethyl)methylamine]cobalt dichloride,
[bis(N-2,6-diethylphenyl-2-aminomethyl)methylamine]cobalt dichloride,
[bis(N-2,4,6-triethylphenyl-2-aminomethyl)methylamine]cobalt dichloride, bis(N-2,6-dimethylphenyl-2-aminopropyl)methylamine]cobalt dichloride,
[bis(N-2,4,6-trimethylphenyl-2-aminopropyl)methylamine]cobalt dichloride,
[bis(N-2,6-diisopropylphenyl-2-aminopropyl)methylamine]cobalt dichloride,
[bis(N-2,4,6-triisopropylphenyl-2-aminopropyl)methylamine]cobalt dichloride,
[bis(N-2,6-diisopropyl-4-methylphenyl-2-aminopropyl)methylamine]cobalt dichloride,
[bis(N-2,6-diethylphenyl-2-aminopropyl)methylamine]cobalt dichloride,
[bis(N-2,4,6-triethylphenyl-2-aminopropyl)methylamine]cobalt dichloride,
[bis(N-2,6-dimethylphenyl-3-aminopropyl)methylamine]cobalt dichloride,
[bis(N-2,4,6-trimethylphenyl-3-aminopropyl)methylamine]cobalt dichloride,
[bis(N-2,6-diisopropylphenyl-3-aminopropyl)methylamine]cobalt dichloride,
[bis(N-2,4,6-triisopropylphenyl-3-aminopropyl)methylamine]cobalt dichloride,
[bis(N-2,6-diisopropyl-4-methylphenyl-3-aminopropyl)methylamine]cobalt dichloride,
[bis(N-2,6-diethylphenyl-3-aminopropyl)methylamine]cobalt dichloride,
[bis(N-2,4,6-triethylphenyl-3-aminopropyl)methylamine]cobalt dichloride,
[(N-2,6-dimethylphenyl-2-aminoethyl)(N-2,6-dimethylphenyl-3-aminopropyl)methylamine]cobalt dichloride,
[(N-2,4,6-trimethylphenyl-2-aminoethyl)(N-2,4,6-trimethylphenyl-3-aminopropyl)methylamine]cobalt dichloride,
[(N-2,6-diisopropylphenyl-2-aminoethyl)(N-2,6-diisopropylphenyl-3-aminopropyl)methylamine]cobalt dichloride,
[(N-2,4,6-triisopropylphenyl-2-aminoethyl)(N-2,4,6-triisopropylphenyl-3-aminopropyl)methylamine]cobalt dichloride,
[(N-2,6-diisopropyl-4-methylphenyl-2-aminoethyl)(N-2,6-diisopropyl-4-methylphenyl-3-aminopropyl)methylamine]cobalt dichloride,
[(N-2,6-diethylphenyl-2-aminoethyl)(N-2,6-diethylphenyl-3-aminopropyl)methylamine]cobalt dichloride,
[(N-2,4,6-triethylphenyl-2-aminoethyl)(N-2,4,6-triethylphenyl-3-aminopropyl)methylamine]cobalt dichloride,
[(N-2,6-dimethylphenyl-2-aminoethyl)(N-2,6-dimethylphenyl-3-aminomethyl)methylamine]cobalt dichloride,
[(N-2,4,6-trimethylphenyl-2-aminoethyl)(N-2,4,6-trimethylphenyl-3-aminomethyl)methylamine]cobalt dichloride,
[(N-2,6-diisopropylphenyl-2-aminoethyl)(N-2,6-diisopropylphenyl-3-aminomethyl)methylamine]cobalt dichloride,
[(N-2,4,6-triisopropylphenyl-2-aminoethyl)(N-2,4,6-triisopropylphenyl-3-aminomethyl)methylamine]cobalt dichloride,
[(N-2,6-diisopropyl-4-methylphenyl-2-aminoethyl)(N-2,6-diisopropyl-4-methylphenyl-3-aminomethyl)methylamine]cobalt dichloride,
[(N-2,6-diethylphenyl-2-aminoethyl)(N-2,6-diethylphenyl-3-aminomethyl)methylamine]cobalt dichloride,
[(N-2,4,6-triethylphenyl-2-aminoethyl)(N-2,4,6-triethylphenyl-3-aminomethyl)methylamine]cobalt dichloride,
[(N-2,6-dimethylphenyl-2-aminoethyl)(N-2,4,6-trimethylphenyl-2-aminoethyl)methylamine]cobalt dichloride,
[(N-2,6-dimethylphenyl-2-aminoethyl)(N-2,6-diisopropylphenyl-2-aminoethyl)methylamine]cobalt dichloride,
[(N-2,6-dimethylphenyl-2-aminoethyl)(N-2,4,6-triisopropylphenyl-2-aminoethyl)methylamine]cobalt dichloride,
[(N-2,6-dimethylphenyl-2-aminoethyl)(N-2,6-diisopropyl-4-methylphenyl-2-aminoethyl)methylamine]cobalt dichloride,

[(N-2,6-dimethylphenyl-2-aminoethyl)(N-2,6-diethylphenyl-2-aminoethyl)methylamine]cobalt dichloride,
[(N-2,6-dimethylphenyl-2-aminoethyl)(N-2,4,6-triethylphenyl-2-aminoethyl)methylamine]cobalt dichloride,
[(N-2,4,6-trimethylphenyl-2-aminoethyl)(N-2,6-diisopropylphenyl-2-aminoethyl)methylamine]cobalt dichloride,
[(N-2,4,6-trimethylphenyl-2-aminoethyl)(N-2,4,6-triisopropylphenyl-2-aminoethyl)methylamine]cobalt dichloride,
[(N-2,4,6-trimethylphenyl-2-aminoethyl)(N-2,6-diisopropyl-4-methylphenyl-2-aminoethyl)methylamine]cobalt dichloride,
[(N-2,4,6-trimethylphenyl-2-aminoethyl)(N-2,6-diethylphenyl-2-aminoethyl)methylamine]cobalt dichloride,
[(N-2,4,6-trimethylphenyl-2-aminoethyl)(N-2,4,6-triethylphenyl-2-aminoethyl)methylamine]cobalt dichloride,
[bis(N-2,6-dimethylphenyl-2-aminoethyl)amine]cobalt dibromide,
[bis(N-2,4,6-trimethylphenyl-2-aminoethyl)amine]cobalt dibromide,
[bis(N-2,6-diisopropylphenyl-2-aminoethyl)amine]cobalt dibromide,
[bis(N-2,4,6-triisopropylphenyl-2-aminoethyl)amine]cobalt dibromide,
[bis(N-2,6-diisopropyl-4-methylphenyl-2-aminoethyl)amine]cobalt dibromide,
[bis(N-2,6-diethylphenyl-2-aminoethyl)amine]cobalt dibromide,
[bis(N-2,4,6-triethylphenyl-2-aminoethyl)amine]cobalt dibromide,
[bis(N-2,6-dimethylphenyl-2-aminomethyl)amine]cobalt dibromide,
[bis(N-2,4,6-trimethylphenyl-2-aminomethyl)amine]cobalt dibromide,
[bis(N-2,6-diisopropylphenyl-2-aminomethyl)amine]cobalt dibromide,
[bis(N-2,4,6-triisopropylphenyl-2-aminomethyl)amine]cobalt dibromide,
[bis(N-2,6-diisopropyl-4-methylphenyl-2-aminomethyl)amine]cobalt dibromide,
[bis(N-2,6-diethylphenyl-2-aminomethyl)amine]cobalt dibromide,
[bis(N-2,4,6-triethylphenyl-2-aminomethyl)amine]cobalt dibromide,
[bis(N-2,6-dimethylphenyl-2-aminopropyl)amine]cobalt dibromide,
[bis(N-2,4,6-trimethylphenyl-2-aminopropyl)amine]cobalt dibromide,
[bis(N-2,6-diisopropylphenyl-2-aminopropyl)amine]cobalt dibromide,
[bis(N-2,4,6-triisopropylphenyl-2-aminopropyl)amine]cobalt dibromide,
[bis(N-2,6-diisopropyl-4-methylphenyl-2-aminopropyl)amine]cobalt dibromide,
[bis(N-2,6-diethylphenyl-2-aminopropyl)amine]cobalt dibromide,
[bis(N-2,4,6-triethylphenyl-2-aminopropyl)amine]cobalt dibromide,
[bis(N-2,6-dimethylphenyl-3-aminopropyl)amine]cobalt dibromide,
[bis(N-2,4,6-trimethylphenyl-3-aminopropyl)amine]cobalt dibromide,
[bis(N-2,6-diisopropylphenyl-3-aminopropyl)amine]cobalt dibromide,
[bis(N-2,4,6-triisopropylphenyl-3-aminopropyl)amine]cobalt dibromide,
[bis(N-2,6-diisopropyl-4-methylphenyl-3-aminopropyl)amine]cobalt dibromide,
[bis(N-2,6-diethylphenyl-3-aminopropyl)amine]cobalt dibromide,
[bis(N-2,4,6-triethylphenyl-3-aminopropyl)amine]cobalt dibromide,
[(N-2,6-dimethylphenyl-2-aminoethyl)(N-2,6-dimethylphenyl-3-aminopropyl)amine]cobalt dibromide,
[(N-2,4,6-trimethylphenyl-2-aminoethyl)(N-2,4,6-trimethylphenyl-3-aminopropyl)amine]cobalt dibromide,
[(N-2,6-diisopropylphenyl-2-aminoethyl)(N-2,6-diisopropylphenyl-3-aminopropyl)amine]cobalt dibromide,
[(N-2,4,6-triisopropylphenyl-2-aminoethyl)(N-2,4,6-triisopropylphenyl-3-aminopropyl)amine]cobalt dibromide,
[(N-2,6-diisopropyl-4-methylphenyl-2-aminoethyl)(N-2,6-diisopropyl-4-methylphenyl-3-aminopropyl)amine]cobalt dibromide,
[(N-2,6-diethylphenyl-2-aminoethyl)(N-2,6-diethylphenyl-3-aminopropyl)amine]cobalt dibromide,
[(N-2,4,6-triethylphenyl-2-aminoethyl)(N-2,4,6-triethylphenyl-3-aminopropyl)amine]cobalt dibromide,
[(N-2,6-dimethylphenyl-2-aminoethyl)(N-2,6-dimethylphenyl-3-aminomethyl)amine]cobalt dibromide,
[(N-2,4,6-trimethylphenyl-2-aminoethyl)(N-2,4,6-trimethylphenyl-3-aminomethyl)amine]cobalt dibromide,
[(N-2,6-diisopropylphenyl-2-aminoethyl)(N-2,6-diisopropylphenyl-3-aminomethyl)amine]cobalt dibromide,
[(N-2,4,6-triisopropylphenyl-2-aminoethyl)(N-2,4,6-triisopropylphenyl-3-aminomethyl)amine]cobalt dibromide,
[(N-2,6-diisopropyl-4-methylphenyl)(N-2,6-diisopropyl-4-methylphenyl-3-aminomethyl)amine]cobalt dibromide,
[(N-2,6-diethylphenyl-2-aminoethyl)(N-2,6-diethylphenyl-3-aminomethyl)amine]cobalt dibromide,
[(N-2,4,6-triethylphenyl-2-aminoethyl)(N-2,4,6-triethylphenyl-3-aminomethyl)amine]cobalt dibromide,
[(N-2,6-dimethylphenyl-2-aminoethyl)(N-2,4,6-trimethylphenyl-2-aminoethyl)amine]cobalt dibromide,
[(N-2,6-dimethylphenyl-2-aminoethyl)(N-2,6-diisopropylphenyl-2-aminoethyl)amine]cobalt dibromide,
[(N-2,6-dimethylphenyl-2-aminoethyl)(N-2,4,6-triisopropylphenyl-2-aminoethyl)amine]cobalt dibromide,
[(N-2,6-dimethylphenyl-2-aminoethyl)(N-2,6-diisopropyl-4-methylphenyl-2-aminoethyl)amine]cobalt dibromide,
[(N-2,6-dimethylphenyl-2-aminoethyl)(N-2,6-diethylphenyl-2-aminoethyl)amine]cobalt dibromide,
[(N-2,6-dimethylphenyl-2-aminoethyl)(N-2,4,6-triethylphenyl-2-aminoethyl)amine]cobalt dibromide,
[(N-2,4,6-trimethylphenyl-2-aminoethyl)(N-2,6-diisopropylphenyl-2-aminoethyl)amine]cobalt dibromide,
[(N-2,4,6-trimethylphenyl-2-aminoethyl)(N-2,4,6-triisopropylphenyl-2-aminoethyl)amine]cobalt dibromide,
[(N-2,4,6-trimethylphenyl-2-aminoethyl)(N-2,6-diisopropyl-4-methylphenyl-2-aminoethyl)amine]cobalt dibromide,
[(N-2,4,6-trimethylphenyl-2-aminoethyl)(N-2,6-diethylphenyl-2-aminoethyl)amine]cobalt dibromide,
[(N-2,4,6-trimethylphenyl-2-aminoethyl)(N-2,4,6-triethylphenyl-2-aminoethyl)amine]cobalt dibromide,
[bis(N-2,6-dimethylphenyl-2-aminoethyl)(2-picolyl)amine]cobalt dibromide,
[bis(N-2,4,6-trimethylphenyl-2-aminoethyl)(2-picolyl)amine]cobalt dibromide,
[bis(N-2,6-diisopropylphenyl-2-aminoethyl)(2-picolyl)amine]cobalt dibromide,
[bis(N-2,4,6-triisopropylphenyl-2-aminoethyl)(2-picolyl)amine]cobalt dibromide,
[bis(N-2,6-diisopropyl-4-methylphenyl-2-aminoethyl)(2-picolyl)amine]cobalt dibromide,

[bis(N-2,6-diethylphenyl-2-aminoethyl)(2-picolyl)amine]cobalt dibromide,
[bis(N-2,4,6-triethylphenyl-2-aminoethyl)(2-picolyl)amine]cobalt dibromide,
[bis(N-2,6-dimethylphenyl-2-aminomethyl)(2-picolyl)amine]cobalt dibromide,
[bis(N-2,4,6-trimethylphenyl-2-aminomethyl)(2-picolyl)amine]cobalt dibromide,
[bis(N-2,6-diisopropylphenyl-2-aminomethyl)(2-picolyl)amine]cobalt dibromide,
[bis(N-2,4,6-triisopropylphenyl-2-aminomethyl)(2-picolyl)amine]cobalt dibromide,
[bis(N-2,6-diisopropyl-4-methylphenyl-2-aminomethyl)(2-picolyl)amine]cobalt dibromide,
[bis(N-2,6-diethylphenyl-2-aminomethyl)(2-picolyl)amine]cobalt dibromide,
[bis(N-2,4,6-triethylphenyl-2-aminomethyl)(2-picolyl)amine]cobalt dibromide,
[bis(N-2,6-dimethylphenyl-2-aminopropyl)(2-picolyl)amine]cobalt dibromide,
[bis(N-2,4,6-trimethylphenyl-2-aminopropyl)(2-picolyl)amine]cobalt dibromide,
[bis(N-2,6-diisopropylphenyl-2-aminopropyl)(2-picolyl)amine]cobalt dibromide,
[bis(N-2,4,6-triisopropylphenyl-2-aminopropyl)(2-picolyl)amine]cobalt dibromide,
[bis(N-2,6-diisopropyl-4-methylphenyl-2-aminopropyl)(2-picolyl)amine]cobalt dibromide,
[bis(N-2,6-diethylphenyl-2-aminopropyl)(2-picolyl)amine]cobalt dibromide,
[bis(N-2,4,6-triethylphenyl-2-aminopropyl)(2-picolyl)amine]cobalt dibromide,
[bis(N-2,6-dimethylphenyl-3-aminopropyl)(2-picolyl)amine]cobalt dibromide,
[bis(N-2,4,6-trimethylphenyl-3-aminopropyl)(2-picolyl)amine]cobalt dibromide,
[bis(N-2,6-diisopropylphenyl-3-aminopropyl)(2-picolyl)amine]cobalt dibromide,
[bis(N-2,4,6-triisopropylphenyl-3-aminopropyl)(2-picolyl)amine]cobalt dibromide,
[bis(N-2,6-diisopropyl-4-methylphenyl-3-aminopropyl)(2-picolyl)amine]cobalt dibromide,
[bis(N-2,6-diethylphenyl-3-aminopropyl)(2-picolyl)amine]cobalt dibromide,
[bis(N-2,4,6-triethylphenyl-3-aminopropyl)(2-picolyl)amine]cobalt dibromide,
[(N-2,6-dimethylphenyl-2-aminoethyl)(N-2,6-dimethylphenyl-3-aminopropyl)(2-picolyl)amine]cobalt dibromide,
[(N-2,4,6-trimethylphenyl-2-aminoethyl)(N-2,4,6-trimethylphenyl-3-aminopropyl)(2-picolyl)amine]cobalt dibromide,
[(N-2,6-diisopropylphenyl-2-aminoethyl)(N-2,6-diisopropylphenyl-3-aminopropyl)(2-picolyl)amine]cobalt dibromide,
[(N-2,4,6-triisopropylphenyl-2-aminoethyl)(N-2,4,6-triisopropylphenyl-3-aminopropyl)(2-picolyl)amine]cobalt dibromide,
[(N-2,6-diisopropyl-4-methylphenyl-2-aminoethyl)(N-2,6-diisopropyl-4-methylphenyl-3-aminopropyl)(2-picolyl)amine]cobalt dibromide,
[(N-2,6-diethylphenyl-2-aminoethyl)(N-2,6-diethylphenyl-3-aminopropyl)(2-picolyl)amine]cobalt dibromide,
[(N-2,4,6-triethylphenyl-2-aminoethyl)(N-2,4,6-triethylphenyl-3-aminopropyl)(2-picolyl)amine]cobalt dibromide,
[(N-2,6-dimethylphenyl-2-aminoethyl)(N-2,6-dimethylphenyl-3-aminomethyl)(2-picolyl)amine]cobalt dibromide,
[(N-2,4,6-trimethylphenyl-2-aminoethyl)(N-2,4,6-trimethylphenyl-3-aminomethyl)(2-picolyl)amine]cobalt dibromide,
[(N-2,6-diisopropylphenyl-2-aminoethyl)(N-2,6-diisopropylphenyl-3-aminomethyl)(2-picolyl)amine]cobalt dibromide,
[(N-2,4,6-triisopropylphenyl-2-aminoethyl)(N-2,4,6-triisopropylphenyl-3-aminomethyl)(2-picolyl)amine]cobalt dibromide,
[(N-2,6-diisopropyl-4-methylphenyl-2-aminoethyl)(N-2,6-diisopropyl-4-methylphenyl-3-aminomethyl)(2-picolyl)amine]cobalt dibromide,
[(N-2,6-diethylphenyl-2-aminoethyl)(N-2,6-diethylphenyl-3-aminomethyl)(2-picolyl)amine]cobalt dibromide,
[(N-2,4,6-triethylphenyl-2-aminoethyl)(N-2,4,6-triethylphenyl-3-aminomethyl)(2-picolyl)amine]cobalt dibromide,
[(N-2,6-dimethylphenyl-2-aminoethyl)(N-2,4,6-trimethylphenyl-2-aminoethyl)(2-picolyl)amine]cobalt dibromide,
[(N-2,6-dimethylphenyl-2-aminoethyl)(N-2,6-diisopropylphenyl-2-aminoethyl)(2-picolyl)amine]cobalt dibromide,
[(N-2,6-dimethylphenyl-2-aminoethyl)(N-2,4,6-triisopropylphenyl-2-aminoethyl)(2-picolyl)amine]cobalt dibromide,
[(N-2,6-dimethylphenyl-2-aminoethyl)(N-2,6-diisopropyl-4-methylphenyl-2-aminoethyl)(2-picolyl)amine]cobalt dibromide,
[(N-2,6-dimethylphenyl-2-aminoethyl)(N-2,6-diethylphenyl-2-aminoethyl)(2-picolyl)amine]cobalt dibromide,
[[(N-2,6-dimethylphenyl-2-aminoethyl)((N-2,4,6-triethylphenyl-2-aminoethyl)(2-picolyl)amine]cobalt dibromide,
[(N-2,4,6-trimethylphenyl-2-aminoethyl)(N-2,6-diisopropylphenyl-2-aminoethyl)(2-picolyl)amine]cobalt dibromide,
[(N-2,4,6-trimethylphenyl-2-aminoethyl)(N-2,4,6-triisopropylphenyl-2-aminoethyl)(2-picolyl)amine]cobalt dibromide,
[(N-2,4,6-trimethylphenyl-2-aminoethyl)(N-2,6-diisopropyl-4-methylphenyl-2-aminoethyl)(2-picolyl)amine]cobalt dibromide,
[(N-2,4,6-trimethylphenyl-2-aminoethyl)(N-2,6-diethylphenyl-2-aminoethyl)(2-picolyl)amine]cobalt dibromide,
[(N-2,4,6-trimethylphenyl-2-aminoethyl)(N-2,4,6-triethylphenyl-2-aminoethyl)(2-picolyl)amine]cobalt dibromide,
[bis(N-2,6-dimethylphenyl-2-aminoethyl)methylamine]cobalt dibromide,
[bis(N-2,4,6-trimethylphenyl-2-aminoethyl)methylamine]cobalt dibromide,
[bis(N-2,6-diisopropylphenyl-2-aminoethyl)methylamine]cobalt dibromide,
[bis(N-2,4,6-triisopropylphenyl-2-aminoethyl)methylamine]cobalt dibromide,
[bis(N-2,6-diisopropyl-4-methylphenyl-2-aminoethyl)methylamine]cobalt dibromide,
[bis(N-2,6-diethylphenyl-2-aminoethyl)methylamine]cobalt dibromide,
[bis(N-2,4,6-triethylphenyl-2-aminoethyl)methylamine]cobalt dibromide,
[bis(N-2,6-dimethylphenyl-2-aminomethyl)methylamine]cobalt dibromide,
[bis(N-2,4,6-trimethylphenyl-2-aminomethyl)methylamine]cobalt dibromide,

[bis(N-2,6-diisopropylphenyl-2-aminomethyl)methylamine]cobalt dibromide,
[bis(N-2,4,6-triisopropylphenyl-2-aminomethyl)methylamine]cobalt dibromide,
[bis(N-2,6-diisopropyl-4-methylphenyl-2-aminomethyl)methylamine]cobalt dibromide,
[bis(N-2,6-diethylphenyl-2-aminomethyl)methylamine]cobalt dibromide,
[bis(N-2,4,6-triethylphenyl-2-aminomethyl)methylamine]cobalt dibromide,
[bis(N-2,6-dimethylphenyl-2-aminopropyl)methylamine]cobalt dibromide,
[bis(N-2,4,6-trimethylphenyl-2-aminopropyl)methylamine]cobalt dibromide,
[bis(N-2,6-diisopropylphenyl-2-aminopropyl)methylamine]cobalt dibromide,
[bis(N-2,4,6-triisopropylphenyl-2-aminopropyl)methylamine]cobalt dibromide,
[bis(N-2,6-diisopropyl-4-methylphenyl-2-aminopropyl)methylamine]cobalt dibromide,
[bis(N-2,6-diethylphenyl-2-aminopropyl)methylamine]cobalt dibromide,
[bis(N-2,4,6-triethylphenyl-2-aminopropyl)methylamine]cobalt dibromide,
[bis(N-2,6-dimethylphenyl-3-aminopropyl)methylamine]cobalt dibromide,
[bis(N-2,4,6-trimethylphenyl-3-aminopropyl)methylamine]cobalt dibromide,
[bis(N-2,6-diisopropylphenyl-3-aminopropyl)methylamine]cobalt dibromide,
[bis(N-2,4,6-triisopropylphenyl-3-aminopropyl)methylamine]cobalt dibromide,
[bis(N-2,6-diisopropyl-4-methylphenyl-3-aminopropyl)methylamine]cobalt dibromide,
[bis(N-2,6-diethylphenyl-3-aminopropyl)methylamine]cobalt dibromide,
[bis(N-2,4,6-triethylphenyl-3-aminopropyl)methylamine]cobalt dibromide,
[(N-2,6-dimethylphenyl-2-aminoethyl)(N-2,6-dimethylphenyl-3-aminopropyl)methylamine]cobalt dibromide,
[(N-2,4,6-trimethylphenyl-2-aminoethyl)(N-2,4,6-trimethylphenyl-3-aminopropyl)methylamine]cobalt dibromide,
[(N-2,6-diisopropylphenyl-2-aminoethyl)(N-2,6-diisopropylphenyl-3-aminopropyl)methylamine]cobalt dibromide,
[(N-2,4,6-triisopropylphenyl-2-aminoethyl)(N-2,4,6-triisopropylphenyl-3-aminopropyl)methylamine]cobalt dibromide,
[(N-2,6-diisopropyl-4-methylphenyl-2-aminoethyl)(N-2,6-diisopropyl-4-methylphenyl-3-aminopropyl)methylamine]cobalt dibromide,
[(N-2,6-diethylphenyl-2-aminoethyl)(N-2,6-diethylphenyl-3-aminopropyl)methylamine]cobalt dibromide,
[(N-2,4,6-triethylphenyl-2-aminoethyl)(N-2,4,6-triethylphenyl-3-aminopropyl)methylamine]cobalt dibromide,
[(N-2,6-dimethylphenyl-2-aminoethyl)(N-2,6-dimethylphenyl-3-aminomethyl)methylamine]cobalt dibromide,
[(N-2,4,6-trimethylphenyl-2-aminoethyl)(N-2,4,6-trimethylphenyl-3-aminomethyl)methylamine]cobalt dibromide,
[(N-2,6-diisopropylphenyl-2-aminoethyl)(N-2,6-diisopropylphenyl-3-aminomethyl)methylamine]cobalt dibromide,
[(N-2,4,6-triisopropylphenyl-2-aminoethyl)(N-2,4,6-triisopropylphenyl-3-aminomethyl)methylamine]cobalt dibromide,
[(N-2,6-diisopropyl-4-methylphenyl-2-aminoethyl)(N-2,6-diisopropyl-4-methylphenyl-3-aminomethyl)methylamine]cobalt dibromide,
[(N-2,6-diethylphenyl-2-aminoethyl)(N-2,6-diethylphenyl-3-aminomethyl)methylamine]cobalt dibromide,
[(N-2,4,6-triethylphenyl-2-aminoethyl)(N-2,4,6-triethylphenyl-3-aminomethyl)methylamine]cobalt dibromide,
[(N-2,6-dimethylphenyl-2-aminoethyl)(N-2,4,6-trimethylphenyl-2-aminoethyl)methylamine]cobalt dibromide,
[(N-2,6-dimethylphenyl-2-aminoethyl)(N-2,6-diisopropylphenyl-2-aminoethyl)methylamine]cobalt dibromide,
[(N-2,6-dimethylphenyl-2-aminoethyl)(N-2,4,6-triisopropylphenyl-2-aminoethyl)methylamine]cobalt dibromide,
[(N-2,6-dimethylphenyl-2-aminoethyl)(N-2,6-diisopropyl-4-methylphenyl-2-aminoethyl)methylamine]cobalt dibromide,
[(N-2,6-dimethylphenyl-2-aminoethyl)(N-2,6-diethylphenyl-2-aminoethyl)methylamine]cobalt dibromide,
[(N-2,6-dimethylphenyl-2-aminoethyl)(N-2,4,6-triethylphenyl-2-aminoethyl)methylamine]cobalt dibromide,
[(N-2,4,6-trimethylphenyl-2-aminoethyl)(N-2,6-diisopropylphenyl-2-aminoethyl)methylamine]cobalt dibromide,
[(N-2,4,6-trimethylphenyl-2-aminoethyl)(N-2,4,6-triisopropylphenyl-2-aminoethyl)methylamine]cobalt dibromide,
[(N-2,4,6-trimethylphenyl-2-aminoethyl)(N-2,6-diisopropyl-4-methylphenyl-2-aminoethyl)methylamine]cobalt dibromide,
[(N-2,4,6-trimethylphenyl-2-aminoethyl)(N-2,6-diethylphenyl-2-aminoethyl)methylamine]cobalt dibromide,
[(N-2,4,6-trimethylphenyl-2-aminoethyl)(N-2,4,6-triethylphenyl-2-aminoethyl)methylamine]cobalt dibromide,
[bis(N-2,6-dimethylphenyl-2-aminoethyl)amine]cobalt dimethyl,
[bis(N-2,4,6-trimethylphenyl-2-aminoethyl)amine]cobalt dimethyl,
[bis(N-2,6-diisopropylphenyl-2-aminoethyl)amine]cobalt dimethyl,
[bis(N-2,4,6-triisopropylphenyl-2-aminoethyl)amine]cobalt dimethyl,
[bis(N-2,6-diisopropyl-4-methylphenyl-2-aminoethyl)amine]cobalt dimethyl,
[bis(N-2,6-diethylphenyl-2-aminoethyl)amine]cobalt dimethyl,
[bis(N-2,6-dimethylphenyl-2-aminoethyl)methylamine]cobalt dimethyl,
[bis(N-2,4,6-trimethylphenyl-2-aminoethyl)methylamine]cobalt dimethyl,
[bis(N-2,6-diisopropylphenyl-2-aminoethyl)methylamine]cobalt dimethyl,
[bis(N-2,4,6-triisopropylphenyl-2-aminoethyl)methylamine]cobalt dimethyl,
[bis(N-2,6-diisopropyl-4-methylphenyl-2-aminoethyl)methylamine]cobalt dimethyl,
[bis(N-2,6-diethylphenyl-2-aminoethyl)methylamine]cobalt dimethyl,
[bis(N-2,6-dimethylphenyl-2-aminoethyl)(2-picolyl)amine]cobalt dimethyl,
[bis(N-2,4,6-trimethylphenyl-2-aminoethyl)(2-picolyl)amine]cobalt dimethyl,
[bis(N-2,6-diisopropylphenyl-2-aminoethyl)(2-picolyl)amine]cobalt dimethyl,
[bis(N-2,4,6-triisopropylphenyl-2-aminoethyl)(2-picolyl)amine]cobalt dimethyl,
[bis(N-2,6-diisopropyl-4-methylphenyl-2-aminoethyl)(2-picolyl)amine]cobalt dimethyl,
[bis(N-2,6-diethylphenyl-2-aminoethyl)(2-picolyl)amine]cobalt dimethyl,

[bis(N-2,6-dimethylphenyl-2-aminoethyl)amine]iron dichloride,
[bis(N-2,4,6-trimethylphenyl-2-aminoethyl)amine]iron dichloride,
[bis(N-2,6-diisopropylphenyl-2-aminoethyl)amine]iron dichloride,
[bis(N-2,4,6-triisopropylphenyl-2-aminoethyl)amine]iron dichloride,
[bis(N-2,6-diisopropyl-4-methylphenyl-2-aminoethyl)amine]iron dichloride,
[bis(N-2,6-diethylphenyl-2-aminoethyl)amine]iron dichloride,
[bis(N-2,4,6-triethylphenyl-2-aminoethyl)amine]iron dichloride,
[bis(N-2,6-dimethylphenyl-2-aminoethyl)methylamine]iron dichloride,
[bis(N-2,4,6-trimethylphenyl-2-aminoethyl)methylamine]iron dichloride,
[bis(N-2,6-diisopropylphenyl-2-aminoethyl)methylamine]iron dichloride,
[bis(N-2,4,6-triisopropylphenyl-2-aminoethyl)methylamine]iron dichloride,
[bis(N-2,6-diisopropyl-4-methylphenyl-2-aminoethyl)methylamine] iron dichloride,
[bis(N-2,6-diethylphenyl-2-aminoethyl)methylamine]iron dichloride,
[bis(N-2,4,6-triethylphenyl-2-aminoethyl)methylamine]iron dichloride,
[bis(N-2,6-dimethylphenyl-2-aminoethyl)(2-picolyl)amine]iron dichloride,
[bis(N-2,4,6-trimethylphenyl-2-aminoethyl)(2-picolyl)amine]iron dichloride,
[bis(N-2,6-diisopropylphenyl-2-aminoethyl)(2-picolyl)amine]iron dichloride,
[bis(N-2,4,6-triisopropylphenyl-2-aminoethyl)(2-picolyl)amine]iron dichloride,
[bis(N-2,6-diisopropyl-4-methylphenyl-2-aminoethyl)(2-picolyl)amine]iron dichloride,
[bis(N-2,6-diethylphenyl-2-aminoethyl)(2-picolyl)amine]iron dichloride,
[bis(N-2,4,6-triethylphenyl-2-aminoethyl)(2-picolyl)amine]iron dichloride,
[bis(N-2,6-dimethylphenyl-2-aminoethyl)amine]manganese dichloride,
[bis(N-2,4,6-trimethylphenyl-2-aminoethyl)amine]manganese dichloride,
[bis(N-2,6-diisopropylphenyl-2-aminoethyl)amine]manganese dichloride,
[bis(N-2,4,6-triisopropylphenyl-2-aminoethyl)amine]manganese dichloride,
[bis(N-2,6-diisopropyl-4-methylphenyl-2-aminoethyl)amine]manganese dichloride,
[bis(N-2,6-diethylphenyl-2-aminoethyl)methylamine]manganese dichloride,
[bis(N-2,4,6-triethylphenyl-2-aminoethyl)methylamine] manganese dichloride,
[bis(N-2,6-dimethylphenyl-2-aminoethyl)methylamine] manganese dichloride,
[bis(N-2,4,6-trimethylphenyl-2-aminoethyl)methylamine] manganese dichloride,
[bis(N-2,6-diisopropylphenyl-2-aminoethyl)methylamine] manganese dichloride,
[bis(N-2,4,6-triisopropylphenyl-2-aminoethyl)methylamine]manganese dichloride,
[bis(N-2,6-diisopropyl-4-methylphenyl-2-aminoethyl)methylamine]manganese dichloride,
[bis(N-2,6-diethylphenyl-2-aminoethyl)methylamine]manganese dichloride,
[bis(N-2,4,6-triethylphenyl-2-aminoethyl)methylamine] manganese dichloride,
[bis(N-2,6-diethylphenyl-2-aminoethyl)(2-picolyl)amine] manganese dichloride,
[bis(N-2,4,6-triethylphenyl-2-aminoethyl)(2-picolyl)amine] manganese dichloride,
[bis(N-2,6-dimethylphenyl-2-aminoethyl)(2-picolyl)amine] manganese dichloride,
[bis(N-2,4,6-trimethylphenyl-2-aminoethyl)(2-picolyl)amine]manganese dichloride,
[bis(N-2,6-diisopropylphenyl-2-aminoethyl)(2-picolyl)amine]manganese dichloride,
[bis(N-2,4,6-triisopropylphenyl-2-aminoethyl)(2-picolyl)amine]manganese dichloride,
[bis(N-2,6-diisopropyl-4-methylphenyl-2-aminoethyl)(2-picolyl)amine]manganese dichloride,
[bis(N-2,6-diethylphenyl-2-aminoethyl)(2-picolyl)amine] manganese dichloride,
[bis(N-2,4,6-triethylphenyl-2-aminoethyl)(2-picolyl)amine] manganese dichloride,
[bis(N-2,6-dimethylphenyl-2-aminoethyl)amine]technetium dichloride,
[bis(N-2,4,6-trimethylphenyl-2-aminoethyl)amine]technetium dichloride,
[bis(N-2,6-diisopropylphenyl-2-aminoethyl)amine]technetium dichloride,
[bis(N-2,6-dimethylphenyl-2-aminoethyl)methylamine] technetium dichloride,
[bis(N-2,4,6-trimethylphenyl-2-aminoethyl)methylamine] technetium dichloride,
[bis(N-2,6-diisopropylphenyl-2-aminoethyl)methylamine] technetium dichloride,
[bis(N-2,6-dimethylphenyl-2-aminoethyl)(2-picolyl)amine] technetium dichloride,
[bis(N-2,4,6-trimethylphenyl-2-aminoethyl)(2-picolyl)amine]technetium dichloride,
[bis(N-2,6-diisopropylphenyl-2-aminoethyl)(2-picolyl)amine]technetium dichloride,
[bis(N-2,6-dimethylphenyl-2-aminoethyl)amine]rhenium dichloride,
[bis(N-2,4,6-trimethylphenyl-2-aminoethyl)amine]rhenium dichloride,
[bis(N-2,6-diisopropylphenyl-2-aminoethyl)amine]rhenium dichloride,
[bis(N-2,6-dimethylphenyl-2-aminoethyl)methylamine]rhenium dichloride,
[bis(N-2,4,6-trimethylphenyl-2-aminoethyl)methylamine] rhenium dichloride,
[bis(N-2,6-diisopropylphenyl-2-aminoethyl)methylamine] rhenium dichloride,
[bis(N-2,6-dimethylphenyl-2-aminoethyl)(2-picolyl)amine] rhenium dichloride,
[bis(N-2,4,6-trimethylphenyl-2-aminoethyl)(2-picolyl)amine]rhenium dichloride,
[bis(N-2,6-diisopropylphenyl-2-aminoethyl)(2-picolyl)amine]rhenium dichloride,
[bis(N-2,6-dimethylphenyl-2-aminoethyl)amine]ruthenium dichloride,
[bis(N-2,4,6-trimethylphenyl-2-aminoethyl)amine]ruthenium dichloride,
[bis(N-2,6-diisopropylphenyl-2-aminoethyl)amine]ruthenium dichloride,
[bis(N-2,6-dimethylphenyl-2-aminoethyl)methylamine]ruthenium dichloride,

[bis(N-2,4,6-trimethylphenyl-2-aminoethyl)methylamine] ruthenium dichloride,
[bis(N-2,6-diisopropylphenyl-2-aminoethyl)methylamine] ruthenium dichloride,
[bis(N-2,6-dimethylphenyl-2-aminoethyl)(2-picolyl)amine] ruthenium dichloride,
[bis(N-2,4,6-trimethylphenyl-2-aminoethyl)(2-picolyl) amine]ruthenium dichloride,
[bis(N-2,6-diisopropylphenyl-2-aminoethyl)(2-picolyl) amine]ruthenium dichloride,
[bis(N-2,6-dimethylphenyl-2-aminoethyl)amine]osmium dichloride,
[bis(N-2,4,6-trimethylphenyl-2-aminoethyl)amine]osmium dichloride,
[bis(N-2,6-diisopropylphenyl-2-aminoethyl)amine]osmium dichloride,
[bis(N-2,6-dimethylphenyl-2-aminoethyl)methylamine]osmium dichloride,
[bis(N-2,4,6-trimethylphenyl-2-aminoethyl)methylamine] osmium dichloride,
[bis(N-2,6-diisopropylphenyl-2-aminoethyl)methylamine] osmium dichloride,
[bis(N-2,6-dimethylphenyl-2-aminoethyl)(2-picolyl)amine] osmium dichloride,
[bis(N-2,4,6-trimethylphenyl-2-aminoethyl)(2-picolyl) amine]osmium dichloride,
[bis(N-2,6-diisopropylphenyl-2-aminoethyl)(2-picolyl) amine]osmium dichloride,
[bis(N-2,6-dimethylphenyl-2-aminoethyl)amine]rhodium dichloride,
[bis(N-2,4,6-trimethylphenyl-2-aminoethyl)amine]rhodium dichloride,
[bis(N-2,6-diisopropylphenyl-2-aminoethyl)amine]rhodium dichloride,
[bis(N-2,6-dimethylphenyl-2-aminoethyl)methylamine] rhodium dichloride,
[bis(N-2,4,6-trimethylphenyl-2-aminoethyl)methylamine] rhodium dichloride,
[bis(N-2,6-diisopropylphenyl-2-aminoethyl)methylamine] rhodium dichloride,
[bis(N-2,6-dimethylphenyl-2-aminoethyl)(2-picolyl)amine] rhodium dichloride,
[bis(N-2,4,6-trimethylphenyl-2-aminoethyl)(2-picolyl) amine]rhodium dichloride,
[bis(N-2,4,6-triethylphenyl-2-aminoethyl)(2-picolyl)amine] rhodium dichloride,
[bis(N-2,6-dimethylphenyl-2-aminoethyl)amine]iridium dichloride,
[bis(N-2,4,6-trimethylphenyl-2-aminoethyl)amine]iridium dichloride,
[bis(N-2,6-diisopropylphenyl-2-aminoethyl)amine]iridium dichloride,
[bis(N-2,6-dimethylphenyl-2-aminoethyl)methylamine]iridium dichloride,
[bis(N-2,4,6-trimethylphenyl-2-aminoethyl)methylamine] iridium dichloride,
[bis(N-2,6-diisopropylphenyl-2-aminoethyl)methylamine] iridium dichloride,
[bis(N-2,6-dimethylphenyl-2-aminoethyl)(2-picolyl)amine] iridium dichloride,
[bis(N-2,4,6-trimethylphenyl-2-aminoethyl)(2-picolyl) amine]iridium dichloride,
[bis(N-2,6-diisopropylphenyl-2-aminoethyl)(2-picolyl) amine]iridium dichloride,
[bis(N-2,4,6-triethylphenyl-2-aminoethyl)methylamine] nickel dichloride,
[bis(N-2,6-dimethylphenyl-2-aminoethyl)(2-picolyl)amine] nickel dichloride,
[bis(N-2,4,6-trimethylphenyl-2-aminoethyl)(2-picolyl) amine]nickel dichloride,
[bis(N-2,6-diisopropylphenyl-2-aminoethyl)(2-picolyl) amine]nickel dichloride,
[bis(N-2,4,6-triisopropylphenyl-2-aminoethyl)(2-picolyl) amine]nickel dichloride,
[bis(N-2,6-diisopropyl-4-methylphenyl-2-aminoethyl)(2-picolyl)amine]nickel dichloride,
[bis(N-2,6-diethylphenyl-2-aminoethyl)(2-picolyl)amine] nickel dichloride,
[bis(N-2,4,6-triethylphenyl-2-aminoethyl)(2-picolyl)amine] nickel dichloride,
[bis(N-2,6-dimethylphenyl-2-aminoethyl)amine]palladium dichloride,
[bis(N-2,4,6-trimethylphenyl-2-aminoethyl)amine]palladium dichloride,
[bis(N-2,6-diisopropylphenyl-2-aminoethyl)amine]palladium dichloride,
[bis(N-2,6-dimethylphenyl-2-aminoethyl)methylamine]palladium dichloride,
[bis(N-2,4,6-trimethylphenyl-2-aminoethyl)methylamine] palladium dichloride,
[bis(N-2,6-diisopropylphenyl-2-aminoethyl)methylamine] palladium dichloride,
[bis(N-2,6-dimethylphenyl-2-aminoethyl)(2-picolyl)amine] palladium dichloride,
[bis(N-2,4,6-trimethylphenyl-2-aminoethyl)(2-picolyl) amine]palladium dichloride,
[bis(N-2,6-diisopropylphenyl-2-aminoethyl)(2-picolyl) amine]palladium dichloride,
[bis(N-2,6-dimethylphenyl-2-aminoethyl)amine]platinum dichloride,
[bis(N-2,4,6-trimethylphenyl-2-aminoethyl)amine]platinum dichloride,
[bis(N-2,6-diisopropylphenyl-2-aminoethyl)amine]platinum dichloride,
[bis(N-2,6-dimethylphenyl-2-aminoethyl)methylamine] platinum dichloride,
[bis(N-2,4,6-trimethylphenyl-2-aminoethyl)methylamine] platinum dichloride,
[bis(N-2,6-diisopropylphenyl-2-aminoethyl)methylamine] platinum dichloride,
[bis(N-2,6-dimethylphenyl-2-aminoethyl)(2-picolyl)amine] platinum dichloride,
[bis(N-2,4,6-trimethylphenyl-2-aminoethyl)(2-picolyl) amine]platinum dichloride,
[bis(N-2,6-diisopropylphenyl-2-aminoethyl)(2-picolyl) amine]platinum dichloride,
[bis(N-2,6-dimethylphenyl-2-aminoethyl)amine]copper dichloride,
[bis(N-2,4,6-trimethylphenyl-2-aminoethyl)amine]copper dichloride,
[bis(N-2,6-diisopropylphenyl-2-aminoethyl)amine]copper dichloride,
[bis(N-2,4,6-triisopropylphenyl-2-aminoethyl)amine]copper dichloride,
[bis(N-2,6-diisopropyl-4-methylphenyl-2-aminoethyl) amine]copper dichloride,
[bis(N-2,6-diethylphenyl-2-aminoethyl)amine]copper dichloride,
[bis(N-2,4,6-triethylphenyl-2-aminoethyl)amine]copper dichloride,
[bis(N-2,6-dimethylphenyl-2-aminoethyl)methylamine] copper dichloride,

[bis(N-2,4,6-trimethylphenyl-2-aminoethyl)methylamine] copper dichloride,
[bis(N-2,6-diisopropylphenyl-2-aminoethyl)methylamine] copper dichloride,
[bis(N-2,4,6-triisopropylphenyl-2-aminoethyl)methylamine]copper dichloride,
[bis(N-2,6-diisopropyl-4-methylphenyl-2-aminoethyl)methylamine]copper dichloride,
[bis(N-2,6-diethylphenyl-2-aminoethyl)methylamine]copper dichloride,
[bis(N-2,4,6-triethylphenyl-2-aminoethyl)methylamine] copper dichloride,
[bis(N-2,6-dimethylphenyl-2-aminoethyl)(2-picolyl)amine] copper dichloride,
[bis(N-2,4,6-trimethylphenyl-2-aminoethyl)(2-picolyl) amine]copper dichloride,
[bis(N-2,6-diisopropylphenyl-2-aminoethyl)(2-picolyl) amine]copper dichloride,
[bis(N-2,4,6-triisopropylphenyl-2-aminoethyl)(2-picolyl) amine]copper dichloride,
[bis(N-2,6-diisopropyl-4-methylphenyl-2-aminoethyl)(2-picolyl)amine]copper dichloride,
[bis(N-2,6-diethylphenyl-2-aminoethyl)(2-picolyl)amine] copper dichloride,
[bis(N-2,4,6-triethylphenyl-2-aminoethyl)(2-picolyl)amine] copper dichloride,
[bis(N-2,6-dimethylphenyl-2-aminoethyl)amine]silver dichloride,
[bis(N-2,4,6-trimethylphenyl-2-aminoethyl)amine]silver dichloride,
[bis(N-2,6-diisopropylphenyl-2-aminoethyl)amine]silver dichloride,
[bis(N-2,6-dimethylphenyl-2-aminoethyl)methylamine]silver dichloride,
[bis(N-2,4,6-trimethylphenyl-2-aminoethyl)methylamine] silver dichloride,
[bis(N-2,6-diisopropylphenyl-2-aminoethyl)methylamine] silver dichloride,
[bis(N-2,6-dimethylphenyl-2-aminoethyl)(2-picolyl)amine] silver dichloride,
[bis(N-2,4,6-trimethylphenyl-2-aminoethyl)(2-picolyl) amine]silver dichloride,
[bis(N-2,6-diisopropylphenyl-2-aminoethyl)(2-picolyl) amine]silver dichloride,
[bis(N-2,6-dimethylphenyl-2-aminoethyl)amine]gold dichloride,
[bis(N-2,4,6-trimethylphenyl-2-aminoethyl)amine]gold dichloride,
[bis(N-2,6-diisopropylphenyl-2-aminoethyl)amine]gold dichloride,
[bis(N-2,6-dimethylphenyl-2-aminoethyl)methylamine] gold dichloride,
[bis(N-2,4,6-trimethylphenyl-2-aminoethyl)methylamine] gold dichloride,
[bis(N-2,6-diisopropylphenyl-2-aminoethyl)methylamine] gold dichloride,
[bis(N-2,6-dimethylphenyl-2-aminoethyl)(2-picolyl)amine] gold dichloride,
[bis(N-2,4,6-trimethylphenyl-2-aminoethyl)(2-picolyl) amine]gold dichloride, and
[bis(N-2,6-diisopropylphenyl-2-aminoethyl)(2-picolyl) amine]gold dichloride, Most preferred transition metal complexes include:
[bis(N-2,6-dimethylphenyl-2-aminoethyl)amine]cobalt dichloride,
[bis(N-2,4,6-trimethylphenyl-2-aminoethyl)amine]cobalt dichloride,
[bis(N-2,6-diisopropylphenyl-2-aminoethyl)amine]cobalt dichloride,
[bis(N-2,4,6-triisopropylphenyl-2-aminoethyl)amine]cobalt dichloride,
[bis(N-2,6-diisopropyl-4-methylphenyl-2-aminoethyl) amine]cobalt dichloride,
[bis(N-2,6-diethylphenyl-2-aminoethyl)amine]cobalt dichloride,
[bis(N-2,6-dimethylphenyl-2-aminoethyl)(2-picolyl)amine] cobalt dichloride,
[bis(N-2,4,6-trimethylphenyl-2-aminoethyl)(2-picolyl) amine]cobalt dichloride,
[bis(N-2,6-diisopropylphenyl-2-aminoethyl)(2-picolyl) amine]cobalt dichloride,
[bis(N-2,4,6-triisopropylphenyl-2-aminoethyl)(2-picolyl) amine]cobalt dichloride,
[bis(N-2,6-diisopropyl-4-methylphenyl-2-aminoethyl)(2-picolyl)amine]cobalt dichloride,
[bis(N-2,6-diethylphenyl-2-aminoethyl)(2-picolyl)amine] cobalt dichloride,
[bis(N-2,6-dimethylphenyl-2-aminoethyl)methylamine]cobalt dichloride,
[bis(N-2,4,6-trimethylphenyl-2-aminoethyl)methylamine] cobalt dichloride,
[bis(N-2,6-diisopropylphenyl-2-aminoethyl)methylamine] cobalt dichloride,
[bis(N-2,4,6-triisopropylphenyl-2-aminoethyl)methylamine]cobalt dichloride,
[bis(N-2,6-diisopropyl-4-methylphenyl-2-aminoethyl)methylamine]cobalt dichloride,
[bis(N-2,6-diethylphenyl-2-aminoethyl)methylamine]cobalt dichloride,
[bis(N-2,6-dimethylphenyl-2-aminoethyl)amine]cobalt dibromide,
[bis(N-2,4,6-trimethylphenyl-2-aminoethyl)amine]cobalt dibromide,
[bis(N-2,6-diisopropylphenyl-2-aminoethyl)amine]cobalt dibromide,
[bis(N-2,4,6-triisopropylphenyl-2-aminoethyl)amine]cobalt dibromide,
[bis(N-2,6-diisopropyl-4-methylphenyl-2-aminoethyl) amine]cobalt dibromide,
[bis(N-2,6-diethylphenyl-2-aminoethyl)amine]cobalt dibromide,
[bis(N-2,6-dimethylphenyl-2-aminoethyl)(2-picolyl)amine] cobalt dibromide,
[bis(N-2,4,6-trimethylphenyl-2-aminoethyl)(2-picolyl) amine]cobalt dibromide,
[bis(N-2,6-diisopropylphenyl-2-aminoethyl)(2-picolyl) amine]cobalt dibromide,
[bis(N-2,4,6-triisopropylphenyl-2-aminoethyl)(2-picolyl) amine]cobalt dibromide,
[bis(N-2,6-diisopropyl-4-methylphenyl-2-aminoethyl)(2-picolyl)amine]cobalt dibromide,
[bis(N-2,6-diethylphenyl-2-aminoethyl)(2-picolyl)amine] cobalt dibromide,
[bis(N-2,6-dimethylphenyl-2-aminoethyl)methylamine]cobalt dibromide,
[bis(N-2,4,6-trimethylphenyl-2-aminoethyl)methylamine] cobalt dibromide,
[bis(N-2,6-diisopropylphenyl-2-aminoethyl)methylamine] cobalt dibromide,
[bis(N-2,4,6-triisopropylphenyl-2-aminoethyl)methylamine]cobalt dibromide,
[bis(N-2,6-diisopropyl-4-methylphenyl-2-aminoethyl)methylamine]cobalt dibromide,

[bis(N-2,6-diethylphenyl-2-aminoethyl)methylamine]cobalt dibromide,
[bis(N-2,6-dimethylphenyl-2-aminoethyl)amine]cobalt dimethyl,
[bis(N-2,4,6-trimethylphenyl-2-aminoethyl)amine]cobalt dimethyl,
[bis(N-2,6-diisopropylphenyl-2-aminoethyl)amine]cobalt dimethyl,
[bis(N-2,4,6-triisopropylphenyl-2-aminoethyl)amine]cobalt dimethyl,
[bis(N-2,6-diisopropyl-4-methylphenyl-2-aminoethyl) amine]cobalt dimethyl,
[bis(N-2,6-diethylphenyl-2-aminoethyl)amine]cobalt dimethyl,
[bis(N-2,6-dimethylphenyl-2-aminoethyl)methylamine]cobalt dimethyl,
[bis(N-2,4,6-trimethylphenyl-2-aminoethyl)methylamine] cobalt dimethyl,
[bis(N-2,6-diisopropylphenyl-2-aminoethyl)methylamine] cobalt dimethyl,
[bis(N-2,4,6-triisopropylphenyl-2-aminoethyl)methylamine]cobalt dimethyl,
[bis(N-2,6-diisopropyl-4-methylphenyl-2-aminoethyl)methylamine]cobalt dimethyl,
[bis(N-2,6-diethylphenyl-2-aminoethyl)methylamine]cobalt dimethyl,
[bis(N-2,6-dimethylphenyl-2-aminoethyl)(2-picolyl)amine] cobalt dimethyl,
[bis(N-2,4,6-trimethylphenyl-2-aminoethyl)(2-picolyl) amine]cobalt dimethyl,
[bis(N-2,6-diisopropylphenyl-2-aminoethyl)(2-picolyl) amine]cobalt dimethyl,
[bis(N-2,4,6-triisopropylphenyl-2-aminoethyl)(2-picolyl) amine]cobalt dimethyl,
[bis(N-2,6-diisopropyl-4-methylphenyl-2-aminoethyl)(2-picolyl)amine]cobalt dimethyl,
[bis(N-2,6-diethylphenyl-2-aminoethyl)(2-picolyl)amine] cobalt dimethyl,
[bis(N-2,6-dimethylphenyl-2-aminoethyl)amine]iron dichloride,
[bis(N-2,4,6-trimethylphenyl-2-aminoethyl)amine]iron dichloride,
[bis(N-2,6-diisopropylphenyl-2-aminoethyl)amine]iron dichloride,
[bis(N-2,4,6-triisopropylphenyl-2-aminoethyl)amine]iron dichloride,
[bis(N-2,6-diisopropyl-4-methylphenyl-2-aminoethyl) amine]iron dichloride,
[bis(N-2,6-diethylphenyl-2-aminoethyl)amine]iron dichloride,
[bis(N-2,6-dimethylphenyl-2-aminoethyl)methylamine]iron dichloride,
[bis(N-2,4,6-trimethylphenyl-2-aminoethyl)methylamine] iron dichloride,
[bis(N-2,6-diisopropylphenyl-2-aminoethyl)methylamine] iron dichloride,
[bis(N-2,4,6-triisopropylphenyl-2-aminoethyl)methylamine]iron dichloride,
[bis(N-2,6-diisopropyl-4-methylphenyl-2-aminoethyl)methylamine]iron dichloride,
[bis(N-2,6-diethylphenyl-2-aminoethyl)methylamine]iron dichloride,
[bis(N-2,6-dimethylphenyl-2-aminoethyl)(2-picolyl)amine] iron dichloride,
[bis(N-2,4,6-trimethylphenyl-2-aminoethyl)(2-picolyl) amine]iron dichloride,
[bis(N-2,6-diisopropylphenyl-2-aminoethyl)(2-picolyl) amine]iron dichloride,
[bis(N-2,4,6-triisopropylphenyl-2-aminoethyl)(2-picolyl) amine]iron dichloride,
[bis(N-2,6-diisopropyl-4-methylphenyl-2-aminoethyl)(2-picolyl)amine]iron dichloride,
[bis(N-2,6-diethylphenyl-2-aminoethyl)(2-picolyl)amine] iron dichloride,
[bis(N-2,6-dimethylphenyl-2-aminoethyl)amine]manganese dichloride,
[bis(N-2,4,6-trimethylphenyl-2-aminoethyl)amine]manganese dichloride,
[bis(N-2,6-diisopropylphenyl-2-aminoethyl)amine]manganese dichloride,
[bis(N-2,4,6-triisopropylphenyl-2-aminoethyl)amine]manganese dichloride,
[bis(N-2,6-diisopropyl-4-methylphenyl-2-aminoethyl) amine]manganese dichloride,
[bis(N-2,6-diethylphenyl-2-aminoethyl)methylamine]manganese dichloride,
[bis(N-2,6-dimethylphenyl-2-aminoethyl)methylamine] manganese dichloride,
[bis(N-2,4,6-trimethylphenyl-2-aminoethyl)methylamine] manganese dichloride,
[bis(N-2,6-diisopropylphenyl-2-aminoethyl)methylamine] manganese dichloride,
[bis(N-2,4,6-triisopropylphenyl-2-aminoethyl)methylamine]manganese dichloride,
[bis(N-2,6-diisopropyl-4-methylphenyl-2-aminoethyl)methylamine]manganese dichloride,
[bis(N-2,6-diethylphenyl-2-aminoethyl)methylamine]manganese dichloride,
[bis(N-2,6-diethylphenyl-2-aminoethyl)(2-picolyl)amine] manganese dichloride,
[bis(N-2,4,6-triethylphenyl-2-aminoethyl)(2-picolyl)amine] manganese dichloride,
[bis(N-2,6-dimethylphenyl-2-aminoethyl)(2-picolyl)amine] manganese dichloride,
[bis(N-2,4,6-trimethylphenyl-2-aminoethyl)(2-picolyl) amine]manganese dichloride,
[bis(N-2,6-diisopropylphenyl-2-aminoethyl)(2-picolyl) amine]manganese dichloride,
[bis(N-2,4,6-triisopropylphenyl-2-aminoethyl)(2-picolyl) amine]manganese dichloride,
[bis(N-2,6-diisopropyl-4-methylphenyl-2-aminoethyl)(2-picolyl)amine]manganese dichloride,
[bis(N-2,6-diethylphenyl-2-aminoethyl)(2-picolyl)amine] manganese dichloride,
[bis(N-2,6-dimethylphenyl-2-aminoethyl)amine]nickel dichloride,
[bis(N-2,4,6-trimethylphenyl-2-aminoethyl)amine]nickel dichloride,
[bis(N-2,6-diisopropylphenyl-2-aminoethyl)amine]nickel dichloride,
[bis(N-2,4,6-triisopropylphenyl-2-aminoethyl)amine]nickel dichloride,
[bis(N-2,6-diisopropyl-4-methylphenyl-2-aminoethyl) amine]nickel dichloride,
[bis(N-2,6-diethylphenyl-2-aminoethyl)amine]nickel dichloride,
[bis(N-2,6-dimethylphenyl-2-aminoethyl)methylamine] nickel dichloride,
[bis(N-2,4,6-trimethylphenyl-2-aminoethyl)methylamine] nickel dichloride,
[bis(N-2,6-diisopropylphenyl-2-aminoethyl)methylamine] nickel dichloride,

[bis(N-2,4,6-triisopropylphenyl-2-aminoethyl)methylamine]nickel dichloride,
[bis(N-2,6-diisopropyl-4-methylphenyl-2-aminoethyl)methylamine]nickel dichloride,
[bis(N-2,6-diethylphenyl-2-aminoethyl)methylamine]nickel dichloride,
[bis(N-2,6-dimethylphenyl-2-aminoethyl)(2-picolyl)amine]nickel dichloride,
[bis(N-2,4,6-trimethylphenyl-2-aminoethyl)(2-picolyl)amine]nickel dichloride,
[bis(N-2,6-diisopropylphenyl-2-aminoethyl)(2-picolyl)amine]nickel dichloride,
[bis(N-2,4,6-triisopropylphenyl-2-aminoethyl)(2-picolyl)amine]nickel dichloride,
[bis(N-2,6-diisopropyl-4-methylphenyl-2-aminoethyl)(2-picolyl)amine]nickel dichloride,
[bis(N-2,6-diethylphenyl-2-aminoethyl)(2-picolyl)amine] nickel dichloride,
[bis(N-2,6-dimethylphenyl-2-aminoethyl)amine]copper dichloride,
[bis(N-2,4,6-trimethylphenyl-2-aminoethyl)amine]copper dichloride,
[bis(N-2,6-diisopropylphenyl-2-aminoethyl)amine]copper dichloride,
[bis(N-2,6-dimethylphenyl-2-aminoethyl)methylamine] copper dichloride,
[bis(N-2,4,6-trimethylphenyl-2-aminoethyl)methylamine] copper dichloride,
[bis(N-2,6-diisopropylphenyl-2-aminoethyl)methylamine] copper dichloride,
[bis(N-2,6-dimethylphenyl-2-aminoethyl)(2-picolyl)amine] copper dichloride,
[bis(N-2,4,6-trimethylphenyl-2-aminoethyl)(2-picolyl) amine]copper dichloride, and
[bis(N-2,6-diisopropylphenyl-2-aminoethyl)(2-picolyl) amine]copper dichloride.

Transition metal complexes of this invention are typically prepared by reacting the tridentate or tetradentate ligand, L, with the desired metal halide, preferably a metal dihalide, in an appropriate solvent, preferably n-butanol, and heating the reaction mixture.

Invention catalyst systems can additionally be prepared by combining, in any order, the ligand, with a Group 7, 8, 9, 10 or 11 metal halide salt, which may optionally be coordinated by solvent, in an activator solution (for example, methylalumoxane dissolved in toluene). All reactants may be added in any order, or even essentially simultaneously.

Common activators that are useful with this invention include:
1. Alumoxanes including alkyl alumoxanes and modified alkylalumoxanes, such as methylalumoxane, modified methylalumoxane, ethylalumoxane and the like;
2. Aluminum alkyls such as trimethyl aluminum, triethyl aluminum, triisopropyl aluminum and the like, and alkyl aluminum halides such as diethyl aluminum chloride, and including alkylaluminum alkoxides; and
3. Ionizing or stoichiometric activators.

The alumoxane component useful as an activator typically is an oligomeric aluminum compound represented by the general formula (R"—Al—O)$_n$, which is a cyclic compound, or R"(R"—Al—O)$_n$AlR"$_2$, which is a linear compound. In the general alumoxane formula, each R" is independently a C$_1$–C$_{20}$ alkyl radical, for example, methyl, ethyl, propyl, butyl, pentyl, isomers thereof, and the like, and "n" is an integer from 1–50. Most preferably, R" is methyl and "n" is at least 4. Methylalumoxane and/or modified methylalumoxanes are most preferred. Another preferred alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584). For further descriptions see, EP 279586, EP 561476, WO94/10180 and U.S. Pat. Nos. 4,665,208, 4,908,463, 4,924,018, 4,952,540, 4,968,827, 5,041,584, 5,103,031, 5,157,137, 5,235,081, 5,248,801, 5,329,032, 5,391,793, and 5,416,229.

Aluminum alkyl components useful as an activators are represented by the general formula:

$$R_m'''AlZ_p$$

where each R''' is, independently, a C$_1$–C$_{20}$ alkyl radical, for example, methyl, ethyl, propyl, butyl, pentyl, hexyl, heptyl, octyl, nonyl, decyl, undecyl, dodecyl, and isomers thereof, preferably methyl, ethyl, propyl, butyl, isobutyl, hexyl, octyl, more preferably methyl, ethyl, isobutyl, n-hexyl or n-octyl;

m is 1, 2 or 3;

each Z is, independently, a C$_1$–C$_{20}$ alkyl radical, for example, methyl, ethyl, propyl, butyl, pentyl, hexyl, heptyl, octyl, nonyl, decyl, undecyl, dodecyl, and isomers thereof, preferably methyl, ethyl, propyl, butyl, isobutyl, hexyl, octyl, or n-octyl, each Z may also be a different univalent anionic ligand such as a halogen (preferably Cl, Br, I), or an alkoxide (OR*), where R* is a C$_1$–C$_{20}$ alkyl radical, for example, methyl, ethyl, propyl, butyl, pentyl, hexyl, heptyl, octyl, nonyl, decyl, undecyl, dodecyl, and isomers thereof, preferably methyl, ethyl, propyl, butyl, isobutyl, hexyl, octyl, or n-octyl, preferably R* is preferably methyl, ethyl, propyl, butyl, isobutyl, hexyl, octyl, n-octyl, chloro, methoxide, ethoxide, propoxide, isopropoxide, butoxide, or t-butoxide; and p is 0, 1 or 2. Preferred aluminum alkyl compounds which may be utilized as activators (or scavengers) include triethylaluminum, diethylaluminum chloride, triisobutylaluminum, tri-n-octylaluminum, trimethylaluminum, and tri-n-hexylaluminum.

When alumoxane, or aluminum alkyl activators are used, the catalyst-precursor-to-activator molar ratio is from about 1:2000 to 10:1; alternatively, 1:1200 to 1:1; alternatively, 1:1000 to 1:1; alternatively 1:500 to 1:1; alternatively 1:400 to 1:10, or alternatively 1:300 to 1:10.

Ionizing activators may be used in the practice of this invention. Preferably, discrete ionizing activators (sometimes also referred to as ionic activators) such as [Me$_2$PhNH][B(C$_6$F$_5$)$_4$], [Bu$_3$NH][BF$_4$], [NH$_4$][PF$_6$], [NH$_4$][SbF$_6$], [NH$_4$][AsF$_6$], [NH$_4$][B(C$_6$H$_5$)$_4$] or Lewis acidic activators such as B(C$_6$F$_5$)$_3$ or B(C$_6$H$_5$)$_3$ can be used if they are used in conjunction with a compound capable of alkylating the metal such as an alumoxane or aluminum alkyl, or if in the pre-catalyst, X is a hydride, hydrocarbyl, substituted hydrocarbyl, halocarbyl, substituted halocarbyl. For purposes of this invention and the claims thereto, Ph is phenyl, Bu is butyl, C$_6$H$_5$ is phenyl; C$_6$F$_5$ is perfluorophenyl or pentafluorophenyl.

It is within the scope of this invention to use an ionizing or stoichiometric activator, neutral or ionic, such as tri(n-butyl)ammonium tetrakis(pentafluorophenyl)boron, a tris (perfluorophenyl)boron metalloid precursor or a tris(perfluoronaphthyl)boron metalloid precursor, polyhalogenated heteroborane anions (WO 98/43983), boric acid (U.S. Pat. No. 5,942,459) or combination thereof. It is also within the scope of this invention to use neutral or ionizing activators alone or in combination with alumoxane or modified alumoxane activators.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated aryl groups, preferably fluorinated aryl groups. Most preferably, the neutral stoichiometric activator is tris(perfluorophenyl)boron or tris(perfluoronaphthyl)boron.

Ionizing stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be prepared by reacting a transition metal compound with one or more neutral Lewis acids, such as $B(C_6F_6)_3$, which upon reaction with the hydrolyzable ligand (X) of the transition metal compound forms an anion, such as $([B(C_6F_5)_3(X)]^-)$, which stabilizes the cationic transition metal species generated by the reaction. The catalysts can be, and preferably are, prepared with activator components which are ionic compounds or compositions. However preparation of activators utilizing neutral compounds is also contemplated by this invention.

Compounds useful as an activator component in the preparation of the ionic catalyst systems used in the process of this invention comprise a cation, which is preferably a Bronsted acid capable of donating a proton, and a compatible non-coordinating anion which anion is relatively large (sterically bulky), capable of stabilizing the active catalyst species (the Group 4 cation) which is formed when the two compounds are combined and said anion will be sufficiently labile to be displaced by olefinic diolefinic and acetylenically unsaturated substrates or other neutral Lewis bases such as ethers, nitrites and the like. Two classes of compatible non-coordinating anions have been disclosed in EPA 277,003 and EPA 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes.

In a preferred embodiment, the stoichiometric activators include a cation and an anion component, and may be represented by the following formula:

$$(L^*\text{-}H)_d^+(A^{d-}) \tag{14}$$

wherein L* is an neutral Lewis base;
H is hydrogen;
$(L^*\text{-}H)^+$ is a Bronsted acid
$A^{d-}$ is a non-coordinating anion having the charge d−
d is an integer from 1 to 3.

The cation component, $(L^*\text{-}H)_d^+$ may include Bronsted acids such as protons or protonated Lewis bases or reducible Lewis acids capable of protonating or abstracting a moiety, such as an alkyl or aryl, from the transition metal catalyst compound, resulting in a cationic transition metal species.

The activating cation $(L^*\text{-}H)_d^-$ may be a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether diethyl ether, tetrahydrofuran and dioxane, sulfoniums from thioethers, such as diethyl thioethers and tetrahydrothiophene, and mixtures thereof. The activating cation $(L\text{-}H)_d^+$ may also be a moiety such as silver, tropylium, carbeniums, ferroceniums and mixtures, preferably carboniums and ferroceniums. Most preferably $(L^*\text{-}H)_d^+$ is triphenyl carbonium.

The anion component $A^{d-}$ include those having the formula $[M^{k+}Q_n]^{d-}$ wherein k is an integer from 1 to 3; n is an integer from 2–6; n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that not more than one Q group is a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst (activator) in the preparation of the improved catalysts of this invention include:

trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, tropillium tetraphenylborate, triphenylcarbenium tetraphenylborate, triphenylphosphonium tetraphenylborate triethylsilylium tetraphenylborate, benzene(diazonium) tetraphenylborate, di(isopropyl)ammonium tetraphenylborate, dicyclohexylammonium tetraphenylborate; tri(o-tolyl)phosphonium tetraphenylborate, tri(2,6-dimethylphenyl)phosphonium tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium)tetrakis(pentafluorophenyl)borate, di(isopropyl)ammonium tetrakis(pentafluorophenyl)borate, dicyclohexylammonium tetrakis(pentafluorophenyl)borate; tri(o-tolyl)phosphonium tetrakis(pentafluorophenyl)borate, tri(2,6-dimethylphenyl)phosphonium tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl) borate, tropillium tetrakis-(2,3,4,6-tetrafluorophenyl) borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, di(isopropyl)ammonium tetrakis(2,3,4,6-tetrafluorophenyl)borate, dicyclohexylammonium tetrakis(2,3,4,6-tetrafluorophenyl)borate; tri(o-tolyl)phosphonium tetrakis(2,3,4,6-tetrafluorophenyl)borate, tri(2,6-dimethylphenyl)phosphonium tetrakis(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, di(isopropyl)ammonium tetrakis(pentafluoronaphthyl)borate, dicyclohexylammonium tetrakis(pentafluoronaphthyl)borate; tri(o-tolyl)phosphonium tetrakis(pentafluoronaphthyl)borate, tri(2,6-dimethylphenyl)phosphonium tetrakis(pentafluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri (n-butyl)ammonium tetrakis(perfluorobiphenyl)borate, tri (t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis (perfluorobiphenyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium)tetrakis (perfluorobiphenyl)borate, di(isopropyl)ammonium tetrakis(pentafluorobiphenyl)borate, dicyclohexylammonium tetrakis(pentafluorobiphenyl)borate; tri(o-tolyl) phosphonium tetrakis(pentafluorobiphenyl)borate, tri(2,6-dimethylphenyl)phosphonium tetrakis (pentafluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl) phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl) borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl) phenyl)borate, tropillium tetrakis(3,5-bis(trifluoromethyl) phenyl)borate, triphenylcarbenium tetrakis(3,5-bis (trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, di(isopropyl)ammonium tetrakis(3,5-bis(trifluoromethyl)phenyl)borate, dicyclohexylammonium tetrakis(3,5-bis(trifluoromethyl)phenyl)borate; tri(o-tolyl) phosphonium tetrakis(3,5-bis(trifluoromethyl)phenyl) borate, and tri(2,6-dimethylphenyl)phosphonium tetrakis (3,5-bis(trifluoromethyl)phenyl)borate.

Most preferably, the ionic stoichiometric activator $(L^*-H)_d^+(A^{d-})$ comprises one or more of:

N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis (perfluorobiphenyl)borate, triphenylcarbenium tetrakis(3,5-bis(trifluoromethyl)phenyl)borate, or triphenylcarbenium tetra(perfluorophenyl)borate.

In one embodiment, an activation method using ionizing ionic compounds not containing an active proton but capable of producing a ligand metallocene catalyst cation and their non-coordinating anion are also contemplated, and are described in EP-A-0 426 637, EP-A-0 573 403 and U.S. Pat. No. 5,387,568, which are all herein incorporated by reference.

Invention catalyst precursors can also be activated with cocatalysts or activators that comprise non-coordinating anions containing metalloid-free cyclopentadienide ions. These are described in U.S. Patent Publication 2002/0058765 A1, published on 16 May 2002.

The term "non-coordinating anion" (NCA) means an anion which either does not coordinate to said cation or which is only weakly coordinated to said cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral four coordinate metallocene compound and a neutral by-product from the anion. Non-coordinating anions useful in accordance with this invention are those that are compatible, stabilize the metallocene cation in the sense of balancing its ionic charge at +1, yet retain sufficient lability to permit displacement by an ethylenically or acetylenically unsaturated monomer during polymerization. These types of cocatalysts sometimes use triisobutyl aluminum or tri-octyl aluminum as a scavenger.

Invention process also can employ cocatalyst compounds or activator compounds that are initially neutral Lewis acids but form a cationic metal complex and a noncoordinating anion, or a zwitterionic complex upon reaction with the invention compounds. For example, tris(pentafluorophenyl) boron or aluminum act to abstract a hydrocarbyl or hydride ligand to yield an invention cationic metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation. For example, tris(perfluorophenyl) boron can be used with methylalumoxane.

When an ionic activator is used, the catalyst-precursor-to-activator molar ratio is from 1:10 to 1.2:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1.2:1; 1:5 to 10:1; 1:5 to 2:1; 1:5 to 3:1; 1:5 to 5:1.

The catalyst-precursor-to-alkylating-agent molar ratio is from 1:100 to 100:1; 1:50 to 50:1; 1:10 to 10:1; 1:10 to 2:1; 1:10 to 25:1; 1:10 to 3:1; 1:10 to 5:1; 1:2 to 10:1; 1:2 to 2:1; 1:2 to 25:1; 1:2 to 3:1; 1:2 to 5:1; 1:25 to 10:1; 1:25 to 2:1; 1:25 to 25:1; 1:25 to 3:1; 1:25 to 5:1; 1:3 to 10:1; 1:3 to 2:1; 1:3 to 25:1; 1:3 to 3:1; 1:3 to 5:1; 1:5 to 10:1; 1:5 to 2:1; 1:5 to 25:1; 1:5 to 3:1; 1:5 to 5:1.

Preferred activators include methylalumoxane, modified methylalumoxane, and mixtures of methylalumoxane with dimethylanilinium tetrakis(pentafluorophenyl)borate or tris(pentafluorophenyl)boron.

Preferred catalyst compound/activator combinations include:

[bis(N-2,6-dimethylphenyl-2-aminoethyl)amine]cobalt dichloride/methylalumoxane,
[bis(N-2,4,6-trimethylphenyl-2-aminoethyl)amine]cobalt dichloride/methylalumoxane,
[bis(N-2,6-diisopropylphenyl-2-aminoethyl)amine]cobalt dichloride/methylalumoxane,
[bis(N-2,4,6-triisopropylphenyl-2-aminoethyl)amine]cobalt dichloride/methylalumoxane,
[bis(N-2,6-diisopropyl-4-methylphenyl-2-aminoethyl)amine]cobalt dichloride/methylalumoxane,
[bis(N-2,6-diethylphenyl-2-aminoethyl)amine]cobalt dichloride/methylalumoxane,
[bis(N-2,6-dimethylphenyl-2-aminoethyl)(2-picolyl)amine]cobalt dichloride/methylalumoxane,
[bis(N-2,4,6-trimethylphenyl-2-aminoethyl)(2-picolyl)amine]cobalt dichloride/methylalumoxane,
[bis(N-2,6-diisopropylphenyl-2-aminoethyl)(2-picolyl)amine]cobalt dichloride/methylalumoxane,
[bis(N-2,4,6-triisopropylphenyl-2-aminoethyl)(2-picolyl)amine]cobalt dichloride/methylalumoxane,
[bis(N-2,6-diisopropyl-4-methylphenyl-2-aminoethyl)(2-picolyl)amine]cobalt dichloride/methylalumoxane,
[bis(N-2,6-diethylphenyl-2-aminoethyl)(2-picolyl)amine]cobalt dichloride/methylalumoxane,
[bis(N-2,6-dimethylphenyl-2-aminoethyl)methylamine]cobalt dichloride/methylalumoxane,
[bis(N-2,4,6-trimethylphenyl-2-aminoethyl)methylamine]cobalt dichloride/methylalumoxane,
[bis(N-2,6-diisopropylphenyl-2-aminoethyl)methylamine]cobalt dichloride/methylalumoxane,
[bis(N-2,4,6-triisopropylphenyl-2-aminoethyl)methylamine]cobalt dichloride/methylalumoxane,
[bis(N-2,6-diisopropyl-4-methylphenyl-2-aminoethyl)methylamine]cobalt dichloride/methylalumoxane,
[bis(N-2,6-diethylphenyl-2-aminoethyl)methylamine]cobalt dichloride/methylalumoxane,
[bis(N-2,6-dimethylphenyl-2-aminoethyl)amine]cobalt dibromide/methylalumoxane,
[bis(N-2,4,6-trimethylphenyl-2-aminoethyl)amine]cobalt dibromide/methylalumoxane,
[bis(N-2,6-dimethylphenyl-2-aminoethyl)(2-picolyl)amine]cobalt dibromide/methylalumoxane,
[bis(N-2,4,6-trimethylphenyl-2-aminoethyl)(2-picolyl)amine]cobalt dibromide/methylalumoxane,
[bis(N-2,6-dimethylphenyl-2-aminoethyl)methylamine]cobalt dibromide/methylalumoxane,
[bis(N-2,4,6-trimethylphenyl-2-aminoethyl)methylamine]cobalt dibromide/methylalumoxane,
[bis(N-2,6-dimethylphenyl-2-aminoethyl)amine]cobalt dimethyl/methylalumoxane,
[bis(N-2,4,6-trimethylphenyl-2-aminoethyl)amine]cobalt dimethyl/methylalumoxane,
[bis(N-2,6-dimethylphenyl-2-aminoethyl)methylamine]cobalt dimethyl/methylalumoxane,
[bis(N-2,4,6-trimethylphenyl-2-aminoethyl)methylamine]cobalt dimethyl/methylalumoxane,
[bis(N-2,6-dimethylphenyl-2-aminoethyl)(2-picolyl)amine]cobalt dimethyl/methylalumoxane,
[bis(N-2,4,6-trimethylphenyl-2-aminoethyl)(2-picolyl)amine]cobalt dimethyl/methylalumoxane,
[bis(N-2,6-dimethylphenyl-2-aminoethyl)amine]iron dichloride/methylalumoxane,
[bis(N-2,4,6-trimethylphenyl-2-aminoethyl)amine]iron dichloride/methylalumoxane,
[bis(N-2,6-diisopropylphenyl-2-aminoethyl)amine] iron dichloride/methylalumoxane,
[bis(N-2,4,6-triisopropylphenyl-2-aminoethyl)amine]iron dichloride/methylalumoxane,
[bis(N-2,6-diisopropyl-4-methylphenyl-2-aminoethyl)amine]iron dichloride/methylalumoxane,
[bis(N-2,6-diethylphenyl-2-aminoethyl)amine]iron dichloride/methylalumoxane,
[bis(N-2,6-dimethylphenyl-2-aminoethyl)methylamine]iron dichloride/methylalumoxane,
[bis(N-2,4,6-trimethylphenyl-2-aminoethyl)methylamine] iron dichloride/methylalumoxane,
[bis(N-2,6-diisopropylphenyl-2-aminoethyl)methylamine] iron dichloride/methylalumoxane,
[bis(N-2,4,6-triisopropylphenyl-2-aminoethyl)methylamine]iron dichloride/methylalumoxane,
[bis(N-2,6-diisopropyl-4-methylphenyl-2-aminoethyl)methylamine]iron dichloride/methylalumoxane,
[bis(N-2,6-diethylphenyl-2-aminoethyl)methylamine]iron dichloride/methylalumoxane,
[bis(N-2,6-dimethylphenyl-2-aminoethyl)(2-picolyl)amine] iron dichloride/methylalumoxane,
[bis(N-2,4,6-trimethylphenyl-2-aminoethyl)(2-picolyl)amine]iron dichloride/methylalumoxane,
[bis(N-2,6-diisopropylphenyl-2-aminoethyl)(2-picolyl)amine]iron dichloride/methylalumoxane,
[bis(N-2,4,6-triisopropylphenyl-2-aminoethyl)(2-picolyl)amine]iron dichloride/methylalumoxane,
[bis(N-2,6-diisopropyl-4-methylphenyl-2-aminoethyl)(2-picolyl)amine]iron dichloride/methylalumoxane,
[bis(N-2,6-diethylphenyl-2-aminoethyl)(2-picolyl)amine] iron dichloride/methylalumoxane,
[bis(N-2,6-dimethylphenyl-2-aminoethyl)amine]manganese dichloride/methylalumoxane,

[bis(N-2,4,6-trimethylphenyl-2-aminoethyl)amine]manganese dichloride/methylalumoxane,
[bis(N-2,6-diisopropylphenyl-2-aminoethyl)amine]manganese dichloride/methylalumoxane,
[bis(N-2,4,6-triisopropylphenyl-2-aminoethyl)amine]manganese dichloride/methylalumoxane,
[bis(N-2,6-diisopropyl-4-methylphenyl-2-aminoethyl)amine]manganese dichloride/methylalumoxane,
[bis(N-2,6-diethylphenyl-2-aminoethyl)methylamine]manganese dichloride/methylalumoxane,
[bis(N-2,6-dimethylphenyl-2-aminoethyl)methylamine]manganese dichloride/methylalumoxane,
[bis(N-2,4,6-trimethylphenyl-2-aminoethyl)methylamine]manganese dichloride/methylalumoxane,
[bis(N-2,6-diisopropylphenyl-2-aminoethyl)methylamine]manganese dichloride/methylalumoxane,
[bis(N-2,4,6-triisopropylphenyl-2-aminoethyl)methylamine]manganese dichloride/methylalumoxane,
[bis(N-2,6-diisopropyl-4-methylphenyl-2-aminoethyl)methylamine]manganese dichloride/methylalumoxane,
[bis(N-2,6-diethylphenyl-2-aminoethyl)methylamine]manganese dichloride/methylalumoxane,
[bis(N-2,6-diethylphenyl-2-aminoethyl)(2-picolyl)amine]manganese dichloride/methylalumoxane,
[bis(N-2,4,6-triethylphenyl-2-aminoethyl)(2-picolyl)amine]manganese dichloride/methylalumoxane,
[bis(N-2,6-dimethylphenyl-2-aminoethyl)(2-picolyl)amine]manganese dichloride/methylalumoxane,
[bis(N-2,4,6-trimethylphenyl-2-aminoethyl)(2-picolyl)amine]manganese dichloride/methylalumoxane,
[bis(N-2,6-diisopropylphenyl-2-aminoethyl)(2-picolyl)amine]manganese dichloride/methylalumoxane,
[bis(N-2,4,6-triisopropylphenyl-2-aminoethyl)(2-picolyl)amine]manganese dichloride/methylalumoxane,
[bis(N-2,6-diisopropyl-4-methylphenyl-2-aminoethyl)(2-picolyl)amine]manganese dichloride/methylalumoxane,
[bis(N-2,6-diethylphenyl-2-aminoethyl)(2-picolyl)amine]manganese dichloride/methylalumoxane,
[bis(N-2,6-dimethylphenyl-2-aminoethyl)amine]nickel dichloride/methylalumoxane,
[bis(N-2,4,6-trimethylphenyl-2-aminoethyl)amine]nickel dichloride/methylalumoxane,
[bis(N-2,6-diisopropylphenyl-2-aminoethyl)amine]nickel dichloride/methylalumoxane,
[bis(N-2,4,6-triisopropylphenyl-2-aminoethyl)amine]nickel dichloride/methylalumoxane,
[bis(N-2,6-diisopropyl-4-methylphenyl-2-aminoethyl)amine]nickel dichloride/methylalumoxane,
[bis(N-2,6-diethylphenyl-2-aminoethyl)amine]nickel dichloride/methylalumoxane,
[bis(N-2,6-dimethylphenyl-2-aminoethyl)methylamine]nickel dichloride/methylalumoxane,
[bis(N-2,4,6-trimethylphenyl-2-aminoethyl)methylamine]nickel dichloride/methylalumoxane,
[bis(N-2,6-diisopropylphenyl-2-aminoethyl)methylamine]nickel dichloride/methylalumoxane,
[bis(N-2,4,6-triisopropylphenyl-2-aminoethyl)methylamine]nickel dichloride/methylalumoxane,
[bis(N-2,6-diisopropyl-4-methylphenyl-2-aminoethyl)methylamine]nickel dichloride/methylalumoxane,
[bis(N-2,6-diethylphenyl-2-aminoethyl)methylamine]nickel dichloride/methylalumoxane,
[bis(N-2,6-dimethylphenyl-2-aminoethyl)(2-picolyl)amine]nickel dichloride/methylalumoxane,
[bis(N-2,4,6-trimethylphenyl-2-aminoethyl)(2-picolyl)amine]nickel dichloride/methylalumoxane,
[bis(N-2,6-diisopropylphenyl-2-aminoethyl)(2-picolyl)amine]nickel dichloride/methylalumoxane,
[bis(N-2,4,6-triisopropylphenyl-2-aminoethyl)(2-picolyl)amine]nickel dichloride/methylalumoxane,
[bis(N-2,6-diisopropyl-4-methylphenyl-2-aminoethyl)(2-picolyl)amine]nickel dichloride/methylalumoxane,
[bis(N-2,6-diethylphenyl-2-aminoethyl)(2-picolyl)amine]nickel dichloride/methylalumoxane,
[bis(N-2,6-dimethylphenyl-2-aminoethyl)amine]copper dichloride/methylalumoxane,
[bis(N-2,4,6-trimethylphenyl-2-aminoethyl)amine]copper dichloride/methylalumoxane,
[bis(N-2,6-diisopropylphenyl-2-aminoethyl)amine]copper dichloride/methylalumoxane,
[bis(N-2,6-dimethylphenyl-2-aminoethyl)methylamine]copper dichloride/methylalumoxane,
[bis(N-2,4,6-trimethylphenyl-2-aminoethyl)methylamine]copper dichloride/methylalumoxane,
[bis(N-2,6-diisopropylphenyl-2-aminoethyl)methylamine]copper dichloride/methylalumoxane,
[bis(N-2,6-dimethylphenyl-2-aminoethyl)(2-picolyl)amine]copper dichloride/methylalumoxane,
[bis(N-2,4,6-trimethylphenyl-2-aminoethyl)(2-picolyl)amine]copper dichloride/methylalumoxane,
[bis(N-2,6-diisopropylphenyl-2-aminoethyl)(2-picolyl)amine]copper dichloride/methylalumoxane,
[bis(N-2,6-dimethylphenyl-2-aminoethyl)amine]cobalt dichloride/modified methylalumoxane,
[bis(N-2,4,6-trimethylphenyl-2-aminoethyl)amine]cobalt dichloride/modified methylalumoxane,
[bis(N-2,6-diisopropylphenyl-2-aminoethyl)amine]cobalt dichloride/modified methylalumoxane,
[bis(N-2,4,6-triisopropylphenyl-2-aminoethyl)amine]cobalt dichloride/modified methylalumoxane,
[bis(N-2,6-diisopropyl-4-methylphenyl-2-aminoethyl)amine]cobalt dichloride/modified methylalumoxane,
[bis(N-2,6-diethylphenyl-2-aminoethyl)amine]cobalt dichloride/modified methylalumoxane,
[bis(N-2,6-dimethylphenyl-2-aminoethyl)(2-picolyl)amine]cobalt dichloride/modified methylalumoxane,
[bis(N-2,4,6-trimethylphenyl-2-aminoethyl)(2-picolyl)amine]cobalt dichloride/modified methylalumoxane,
[bis(N-2,6-diisopropylphenyl-2-aminoethyl)(2-picolyl)amine]cobalt dichloride/modified methylalumoxane,
[bis(N-2,4,6-triisopropylphenyl-2-aminoethyl)(2-picolyl)amine]cobalt dichloride/modified methylalumoxane,
[bis(N-2,6-diisopropyl-4-methylphenyl-2-aminoethyl)(2-picolyl)amine]cobalt dichloride/modified methylalumoxane,
[bis(N-2,6-diethylphenyl-2-aminoethyl)(2-picolyl)amine]cobalt dichloride/modified methylalumoxane,
[bis(N-2,6-dimethylphenyl-2-aminoethyl)methylamine]cobalt dichloride/modified methylalumoxane,
[bis(N-2,4,6-trimethylphenyl-2-aminoethyl)methylamine]cobalt dichloride/modified methylalumoxane,
[bis(N-2,6-diisopropylphenyl-2-aminoethyl)methylamine]cobalt dichloride/modified methylalumoxane,
[bis(N-2,4,6-triisopropylphenyl-2-aminoethyl)methylamine]cobalt dichloride/modified methylalumoxane,
[bis(N-2,6-diisopropyl-4-methylphenyl-2-aminoethyl)methylamine]cobalt dichloride/modified methylalumoxane,
[bis(N-2,6-diethylphenyl-2-aminoethyl)methylamine]cobalt dichloride/modified methylalumoxane,
[bis(N-2,6-dimethylphenyl-2-aminoethyl)amine]cobalt dibromide/modified methylalumoxane,
[bis(N-2,4,6-trimethylphenyl-2-aminoethyl)amine]cobalt dibromide/modified methylalumoxane,

[bis(N-2,6-dimethylphenyl-2-aminoethyl)(2-picolyl)amine] cobalt dibromide/modified methylalumoxane,
[bis(N-2,4,6-trimethylphenyl-2-aminoethyl)(2-picolyl) amine]cobalt dibromide/modified methylalumoxane,
[bis(N-2,6-dimethylphenyl-2-aminoethyl)methylamine]cobalt dibromide/modified methylalumoxane,
[bis(N-2,4,6-trimethylphenyl-2-aminoethyl)methylamine] cobalt dibromide/modified methylalumoxane,
[bis(N-2,6-dimethylphenyl-2-aminoethyl)amine]cobalt dimethyl/modified methylalumoxane,
[bis(N-2,4,6-trimethylphenyl-2-aminoethyl)amine]cobalt dimethyl/modified methylalumoxane,
[bis(N-2,6-dimethylphenyl-2-aminoethyl)methylamine]cobalt dimethyl/modified methylalumoxane,
[bis(N-2,4,6-trimethylphenyl-2-aminoethyl)methylamine] cobalt dimethyl/modified methylalumoxane,
[bis(N-2,6-dimethylphenyl-2-aminoethyl)(2-picolyl)amine] cobalt dimethyl/modified methylalumoxane,
[bis(N-2,4,6-trimethylphenyl-2-aminoethyl)(2-picolyl) amine]cobalt dimethyl/modified methylalumoxane,
[bis(N-2,6-dimethylphenyl-2-aminoethyl)amine]iron dichloride/modified methylalumoxane,
[bis(N-2,4,6-trimethylphenyl-2-aminoethyl)amine]iron dichloride/modified methylalumoxane,
[bis(N-2,6-diisopropylphenyl-2-aminoethyl)amine]iron dichloride/modified methylalumoxane,
[bis(N-2,4,6-triisopropylphenyl-2-aminoethyl)amine]iron dichloride/modified methylalumoxane,
[bis(N-2,6-diisopropyl-4-methylphenyl-2-aminoethyl) amine]iron dichloride/modified methylalumoxane,
[bis(N-2,6-diethylphenyl-2-aminoethyl)amine]iron dichloride/modified methylalumoxane,
[bis(N-2,6-dimethylphenyl-2-aminoethyl)methylamine]iron dichloride/modified methylalumoxane,
[bis(N-2,4,6-trimethylphenyl-2-aminoethyl)methylamine] iron dichloride/modified methylalumoxane,
[bis(N-2,6-diisopropylphenyl-2-aminoethyl)methylamine] iron dichloride/modified methylalumoxane,
[bis(N-2,4,6-triisopropylphenyl-2-aminoethyl)methylamine]iron dichloride/modified methylalumoxane,
[bis(N-2,6-diisopropyl-4-methylphenyl-2-aminoethyl)methylamine]iron dichloride/modified methylalumoxane,
[bis(N-2,6-diethylphenyl-2-aminoethyl)methylamine]iron dichloride/modified methylalumoxane,
[bis(N-2,6-dimethylphenyl-2-aminoethyl)(2-picolyl)amine] iron dichloride/modified methylalumoxane,
[bis(N-2,4,6-trimethylphenyl-2-aminoethyl)(2-picolyl) amine]iron dichloride/modified methylalumoxane,
[bis(N-2,6-diisopropylphenyl-2-aminoethyl)(2-picolyl) amine]iron dichloride/modified methylalumoxane,
[bis(N-2,4,6-triisopropylphenyl-2-aminoethyl)(2-picolyl) amine]iron dichloride/modified methylalumoxane,
[bis(N-2,6-diisopropyl-4-methylphenyl-2-aminoethyl)(2-picolyl)amine]iron dichloride/modified methylalumoxane,
[bis(N-2,6-diethylphenyl-2-aminoethyl)(2-picolyl)amine] iron dichloride/modified methylalumoxane,
[bis(N-2,6-dimethylphenyl-2-aminoethyl)amine]manganese dichloride/modified methylalumoxane,
[bis(N-2,4,6-trimethylphenyl-2-aminoethyl)amine]manganese dichloride/modified methylalumoxane,
[bis(N-2,6-diisopropylphenyl-2-aminoethyl)amine]manganese dichloride/modified methylalumoxane,
[bis(N-2,4,6-triisopropylphenyl-2-aminoethyl)amine]manganese dichloride/modified methylalumoxane,
[bis(N-2,6-diisopropyl-4-methylphenyl-2-aminoethyl) amine]manganese dichloride/modified methylalumoxane,
[bis(N-2,6-diethylphenyl-2-aminoethyl)methylamine]manganese dichloride/modified methylalumoxane,
[bis(N-2,6-dimethylphenyl-2-aminoethyl)methylamine] manganese dichloride/modified methylalumoxane,
[bis(N-2,4,6-trimethylphenyl-2-aminoethyl)methylamine] manganese dichloride/modified methylalumoxane,
[bis(N-2,6-diisopropylphenyl-2-aminoethyl)methylamine] manganese dichloride/modified methylalumoxane,
[bis(N-2,4,6-triisopropylphenyl-2-aminoethyl)methylamine]manganese dichloride/modified methylalumoxane,
[bis(N-2,6-diisopropyl-4-methylphenyl-2-aminoethyl)methylamine]manganese dichloride/modified methylalumoxane,
[bis(N-2,6-diethylphenyl-2-aminoethyl)methylamine]manganese dichloride/modified methylalumoxane,
[bis(N-2,6-diethylphenyl-2-aminoethyl)(2-picolyl)amine] manganese dichloride/modified methylalumoxane,
[bis(N-2,4,6-triethylphenyl-2-aminoethyl)(2-picolyl)amine] manganese dichloride/modified methylalumoxane,
[bis(N-2,6-dimethylphenyl-2-aminoethyl)(2-picolyl)amine] manganese dichloride/modified methylalumoxane,
[bis(N-2,4,6-trimethylphenyl-2-aminoethyl)(2-picolyl) amine]manganese dichloride/modified methylalumoxane,
[bis(N-2,6-diisopropylphenyl-2-aminoethyl)(2-picolyl) amine]manganese dichloride/modified methylalumoxane,
[bis(N-2,4,6-triisopropylphenyl-2-aminoethyl)(2-picolyl) amine]manganese dichloride/modified methylalumoxane,
[bis(N-2,6-diisopropyl-4-methylphenyl-2-aminoethyl)(2-picolyl)amine]manganese dichloride/modified methylalumoxane,
[bis(N-2,6-diethylphenyl-2-aminoethyl)(2-picolyl)amine] manganese dichloride/modified methylalumoxane,
[bis(N-2,6-dimethylphenyl-2-aminoethyl)amine]nickel dichloride/modified methylalumoxane,
[bis(N-2,4,6-trimethylphenyl-2-aminoethyl)amine]nickel dichloride/modified methylalumoxane,
[bis(N-2,6-diisopropylphenyl-2-aminoethyl)amine]nickel dichloride/modified methylalumoxane,
[bis(N-2,4,6-triisopropylphenyl-2-aminoethyl)amine]nickel dichloride/modified methylalumoxane,
[bis(N-2,6-diisopropyl-4-methylphenyl-2-aminoethyl) amine]nickel dichloride/modified methylalumoxane,
[bis(N-2,6-diethylphenyl-2-aminoethyl)amine]nickel dichloride/modified methylalumoxane,
[bis(N-2,6-dimethylphenyl-2-aminoethyl)methylamine] nickel dichloride/modified methylalumoxane,
[bis(N-2,4,6-trimethylphenyl-2-aminoethyl)methylamine] nickel dichloride/modified methylalumoxane,
[bis(N-2,6-diisopropylphenyl-2-aminoethyl)methylamine] nickel dichloride/modified methylalumoxane,
[bis(N-2,4,6-triisopropylphenyl-2-aminoethyl)methylamine]nickel dichloride/modified methylalumoxane,
[bis(N-2,6-diisopropyl-4-methylphenyl-2-aminoethyl)methylamine]nickel dichloride/modified methylalumoxane,
[bis(N-2,6-diethylphenyl-2-aminoethyl)methylamine]nickel dichloride/modified methylalumoxane,
[bis(N-2,6-dimethylphenyl-2-aminoethyl)(2-picolyl)amine] nickel dichloride/modified methylalumoxane,
[bis(N-2,4,6-trimethylphenyl-2-aminoethyl)(2-picolyl) amine]nickel dichloride/modified methylalumoxane,
[bis(N-2,6-diisopropylphenyl-2-aminoethyl)(2-picolyl) amine]nickel dichloride/modified methylalumoxane,
[bis(N-2,4,6-triisopropylphenyl-2-aminoethyl)(2-picolyl) amine]nickel dichloride/modified methylalumoxane,

[bis(N-2,6-diisopropyl-4-methylphenyl-2-aminoethyl)(2-picolyl)amine]nickel dichloride/modified methylalumoxane,
[bis(N-2,6-diethylphenyl-2-aminoethyl)(2-picolyl)amine] nickel dichloride/modified methylalumoxane,
[bis(N-2,6-dimethylphenyl-2-aminoethyl)amine]copper dichloride/modified methylalumoxane,
[bis(N-2,4,6-trimethylphenyl-2-aminoethyl)amine]copper dichloride/modified methylalumoxane,
[bis(N-2,6-diisopropylphenyl-2-aminoethyl)amine]copper dichloride/modified methylalumoxane,
[bis(N-2,6-dimethylphenyl-2-aminoethyl)methylamine] copper dichloride/modified methylalumoxane,
[bis(N-2,4,6-trimethylphenyl-2-aminoethyl)methylamine] copper dichloride/modified methylalumoxane,
[bis(N-2,6-diisopropylphenyl-2-aminoethyl)methylamine] copper dichloride/modified methylalumoxane,
[bis(N-2,6-dimethylphenyl-2-aminoethyl)(2-picolyl)amine] copper dichloride/modified methylalumoxane,
[bis(N-2,4,6-trimethylphenyl-2-aminoethyl)(2-picolyl) amine]copper dichloride/modified methylalumoxane, and
[bis(N-2,6-diisopropylphenyl-2-aminoethyl)(2-picolyl) amine]copper dichloride/modified methylalumoxane.

Mixed Catalysts:

Mixed catalyst systems can also be used, for example, the invention catalyst can be used in conjunction with a second catalyst in the same reactor or in a series of reactors where the invention catalyst produces ethylene oligomers and the second catalyst incorporates these oligomers into a polymer backbone as a copolymer with ethylene.

Invention polymerization catalyst systems can comprise additional olefin polymerization catalysts. These additional olefin polymerization catalysts are any of those well known in the art to catalyze the olefin to polyolefin reaction. Some invention catalysts systems include Group-4–6 metallocenes as additional olefin polymerization catalysts. Metallocenes include (un)bridged compounds containing one (mono(cyclopentadienyl) metallocenes) or two (bis(cyclopentadienyl) metallocenes) (un)substituted cyclopentadienyl ligand(s). In bridged metallocenes, a single, cyclopentadienyl ligand connects to a heteroatom ligand with both coordinating to the metal center, or two cyclopentadienyl ligands connect together with both cyclopentadienyl ligands coordinating to the metal center. Typical catalysts and their precursors are well known in the art. Suitable description appears in the patent literature, for example U.S. Pat. Nos. 4,871,705, 4,937,299, 5,324,800, EP-A-0418044, EP-A-0591756, WO-A-92/00333 and WO-A-94/01471. Some embodiments select the metallocene compounds from mono- or bis-cyclopentadienyl-substituted, Group-4, -5, and -6 metals in which cyclopentadienyls are (un)substituted with one or more groups or are bridged to each other or to a metal-coordinated heteroatom. Some embodiments select similar metallocene compounds except they are not necessarily bridged to each other or to a metal-coordinated heteroatom. See U.S. Pat. Nos. 5,278,264 and 5,304,614.

Some invention catalysts systems include the following additional olefin polymerization catalysts. Metallocene compounds suitable for linear polyethylene or ethylene-containing copolymer production (where copolymer means comprising at least two different monomers) are essentially those disclosed in WO-A-92/00333, WO 97/44370 and U.S. Pat. Nos. 5,001,205, 5,057,475, 5,198,401, 5,304,614, 5,308,816 and 5,324,800. Selection of metallocene compounds for isotactic or syndiotactic polypropylene blend production, and their syntheses, are well-known in the patent and academic literature, e.g. *Journal of Organometallic Chemistry* 369, 359–370 (1989). Typically, those catalysts are stereorigid, asymmetric, chiral, or bridged-chiral metallocenes. Invention activators are suited for activating these types of catalyst precursors.

Likewise, some invention catalysts systems include the following additional olefin polymerization catalysts: mono-cyclopentadienyl metallocenes with Group-15 or -16 heteroatoms connected, through a bridging group, to a cyclopentadienyl-ligand ring carbon. Both the cyclopentadienyl Cp-ligand and the heteroatom connect to a transition metal. Some embodiments select a Group-4 transition metal. Additionally, unbridged monocyclopentadienyl, heteroatom-containing Group-4 components of WO 97/22639 will function with this invention. Moreover, transition metal systems with high-oxidation-state, Group-5–10 transition-metal centers are known and can serve as the additional olefin polymerization catalysts with invention catalyst systems.

Invention catalyst systems can use non-cyclopentadienyl, Group-4–5 precursor compounds as the additional olefin polymerization catalysts. Non-cyclopentadienyl, Group-4–5 precursor compounds are activable to stable, discrete cationic complexes include those containing, chelating, diamide ligands, such as described in U.S. Pat. No. 5,318,935 and "Conformationally Rigid Diamide Complexes: Synthesis and Structure of Tantalum (III) Alkyne Derivatives", D. H. McConville, et al, *Organometallics* 1995, 14, 3154–3156. U.S. Pat. No. 5,318,935 describes bridged and unbridged, bis-amido catalyst compounds of Group-4 metals capable of α-olefins polymerization. Bridged bis(arylamido) Group-4 compounds for olefin polymerization are described by D. H. McConville, et al., in *Organometallics* 1995, 14, 5478–5480. Synthetic methods and compound characterization are presented. Further work appearing in D. H. McConville, et al, *Macromolecules* 1996, 29, 5241–5243, describes bridged bis(arylamido) Group-4 compounds that are polymerization catalysts for 1-hexene. Additional invention-suitable transition-metal compounds include those described in WO 96/40805. Cationic Group-3- or Lanthanide olefin polymerization complexes are disclosed in copending U.S. application Ser. No. 09/408,050, filed 29 Sep. 1999, and its equivalent PCT/US99/22690. A monoanionic bidentate ligand and two monoanionic ligands stabilize those catalyst precursors; they are activable with this invention" ionic cocatalysts. Other suitable Group-4–5 non-metallocene catalysts are bimetallocyclic catalyst compounds comprising two independently selected Group-4–5 metal atoms directly linked through two bridging groups to form cyclic compounds.

Invention catalyst systems can use other transition metal catalyst precursors that have a 2+ oxidation state as the additional olefin polymerization catalyst. Typical $Ni^{2+}$ and $Pd^{2+}$ complexes are diimines, see "New Pd(II)- and Ni(II)-Based Catalysts for Polymerization of Ethylene and α-Olefins", M. Brookhart, et al, *J. Am. Chem. Soc.,* 1995, 117, 6414–6415, WO 96/23010 and WO 97/02298. See additionally the related bis(imino) Group-8 and -9 organometallic compounds described by V. C. Gibson and others in "Novel olefin polymerization catalysts based on iron and cobalt", *Chem. Commun.,* 849–850, 1998.

For a review of other potential catalysts used in combination or series with the invention catalysts, see S. D. Ittel and L. K. Johnson, Chem. Rev. 2000, 1000, 1169 and V. C. Gibson and S. K. Spitzmesser, Chem. Rev. 2003, 103, 283.

Supports:

The transition metal catalyst components described herein may be supported. For example, one or more transition metal catalyst components and/or one or more activators may be deposited on, contacted with, vaporized with, bonded to, or incorporated within, adsorbed or absorbed in, or on, one or more supports or carriers.

The support material may be any of the conventional support materials. Preferably the support material is a porous support material, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

Preferred support materials are inorganic oxides that include those Group 2, 3, 4, 5, 13 or 14 metal oxides. Preferred supports include silica, which may or may not be dehydrated, fumed silica, alumina (WO 99/60033), silica-alumina and mixtures thereof. Other useful supports include magnesia, titania, zirconia, magnesium chloride (U.S. Pat. No. 5,965,477), montmorillonite (European Patent EP-B1 0 511 665), phyllosilicate, zeolites, talc, clays (U.S. Pat. No. 6,034,187) and the like. Also, combinations of these support materials may be used, for example, silica-chromium, silica-alumina, silica-titania and the like. Additional support materials may include those porous acrylic polymers described in EP 0 767 184 B1, which is incorporated herein by reference. Other support materials include nanocomposites as described in PCT WO 99/47598, aerogels as described in WO 99/48605, spherulites as described in U.S. Pat. No. 5,972,510 and polymeric beads as described in WO 99/50311, which are all herein incorporated by reference. Lewis acidic materials such as montmorillonite and similar clays may also serve as a support. In this case, the support can optionally double as the activator component. But additional activator may also be used.

It is preferred that the support material, most preferably an inorganic oxide, has a surface area in the range of from about 10 to about 700 $m^2/g$, pore volume in the range of from about 0.1 to about 4.0 cc/g and average particle size in the range of from about 5 to about 500 μm. More preferably, the surface area of the support material is in the range of from about 50 to about 500 $m^2/g$, pore volume of from about 0.5 to about 3.5 cc/g and average particle size of from about 10 to about 200 μm. Most preferably the surface area of the support material is in the range is from about 100 to about 400 $m^2/g$, pore volume from about 0.8 to about 3.0 cc/g and average particle size is from about 5 to about 100 μm. The average pore size of the carrier useful in the invention typically has pore size in the range of from 10 to 1000 Å, preferably 50 to about 500 Å, and most preferably 75 to about 350 Å.

As is known in the art, the catalysts may also be supported together on one inert support, or the catalysts may be independently placed on two inert supports and subsequently mixed. Of the two methods, the former is preferred.

In another embodiment the support may comprise one or more types of support material which may be treated differently. For example one could use two different silicas that had different pore volumes or had been calcined at different temperatures. Likewise one could use a silica that had been treated with a scavenger or other additive and a silica that had not.

Supported transition metal catalyst compounds, activators, or catalyst systems may be prepared by placing the support material (which may be pre-treated, such as calcined or functionalized) and one or more catalyst compounds, or one or more activators, or both activators and catalyst compounds in a diluent, typically a solvent, and them removing the diluent or solvent. The volume of the liquid may be from 0.5 to 20 time the pore volume of the support or more. Certain embodiments, however, use 1 to 3 times the pore volume of the support.

Typically the instant supported catalyst systems may be prepared by any method effective to support other coordination catalyst systems, effective meaning that the catalyst so prepared can be used for oligomerizing or polymerizing monomers in a heterogeneous process. The catalyst precursor, activator, suitable diluent, and support may be added in any order or simultaneously. In one invention embodiment, the activator, dissolved in an appropriate solvent such as toluene is stirred with the support material for 1 minute to 10 hours. The total volume of the activation solution may be greater than the pore volume of the support, but some embodiments limit the total solution volume below that needed to form a gel or slurry (about 100–200% of the pore volume). In some embodiments the volume of the solution is limited to between 1 and 5 times the pore volume of the support, typically between 1.5 and 3. The mixture is optionally heated to 30–200° C. during this time. The catalyst can be added to this mixture as a solid, if a suitable solvent is employed in the previous step, or as a solution. Or alternatively, this mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the catalyst is either filtered from the solution and vacuum dried, or vacuum or evaporation alone removes the solvent.

In another invention embodiment, the catalyst precursor and activator are combined in solvent to form a solution. The support is then added to this solution and the mixture is stirred for 1 minute to 10 hours. The total volume of this solution may be greater than the pore volume of the support, but some embodiments limit the total solution volume below that needed to form a gel or slurry (about 100–200% pore volume). In some embodiments the volume of the solution is limited to between 1 and 5 times the pore volume of the support, typically between 1.5 and 3. The residual solvent is then removed, typically under vacuum, typically at ambient temperature and over 10–16 hours. But greater or lesser times are possible.

The catalyst precursor may also be supported in the absence of the activator, in which case the activator is added to the liquid phase of a slurry process. For example, a solution of catalyst precursor is mixed with a support material for a period of up to 10 hours. The resulting catalyst precursor mixture is then filtered from the solution and dried under vacuum, or vacuum or evaporation alone removes the solvent. The total volume of the catalyst precursor solution may be greater than the pore volume of the support, but some embodiments limit the total solution volume below that needed to form a gel or slurry (about 100–200% of the pore volume). In some embodiments the volume of the solution is limited to between 1 and 5 times the pore volume of the support, typically between 1.5 and 3. Additionally, two or more different catalyst precursors may be placed on the same support using any of the support methods disclosed above. Likewise, two or more activators may be placed on the same support.

As well know in the art, the support material may be pretreated by any number of methods. For example, inorganic oxides may be calcined, and/or chemically treated with dehydroxylating agents such as aluminum alkyls and the like.

Some embodiments select the carrier of invention catalysts to have a surface area of 10–700 m$^2$/g, or pore volume of 0.1–4.0 cc/g, and average particle size from 10–500 microns. But greater or lesser values may also be used.

The transition metal catalyst compounds may generally be deposited on the support at a loading level of 10–100 micromoles of catalyst precursor per gram of solid support; alternately from 20–80 micromoles of catalyst precursor per gram of solid support; or from 40–60 micromoles of catalyst precursor per gram of support. But greater or lesser values may be used. Some embodiments select greater or lesser values, but require that the total amount of solid catalyst precursor does not exceed the support's pore volume.

Additionally, oxidizing agents may be added to the supported or unsupported catalyst as described in WO 01/68725.

In another embodiment the activator is bound to the support prior to combination with the transition metal catalyst compound. For more information on support bound activators, please see U.S. Pat. No. 5,643,847, U.S. Pat. No. 5,972,823, EP 0 775 164 B1, WO 00/4059 A1, WO 95/9578 A1.

Oligomerization or Polymerization Process

The catalyst compositions described above may be used to oligomerize or polymerize any unsaturated monomer, however they are preferably used to oligomerize olefins, typically alpha-olefins. In the instant oligomerization processes, the process temperature may be –100° C. to 300° C., –20° C. to 200° C., or 0° C. to 150° C. Some embodiments select oligomerization pressures (gauge) from 0 kPa–35 MPa or 500 kPa–15 MPa. A preferred feedstock for the oligomerization process is the alpha-olefin, ethylene. But other alpha-olefins, including but not limited to propylene and 1-butene, may also be used alone or combined with ethylene. Preferred alpha-olefins include any $C_2$ to $C_{40}$ alpha-olefin, preferably $C_2$ to $C_{20}$ alpha-olefin, preferably any $C_2$ to $C_{12}$ alpha-olefin, preferably ethylene, propylene, and butene, most preferably ethylene. Dienes may be used in the processes described herein, preferably alpha, omega-dienes are used alone or in combination with mono-alpha olefins.

Preferred oligomerization processes may be run in the presence of various liquids, particularly aprotic organic liquids. Preferably the homogeneous catalyst system, ethylene, alpha-olefins, and product are soluble in these liquids. A supported (heterogeneous) catalyst system may also be used, but will form a slurry rather than a solution. Suitable liquids for both homo- and heterogeneous catalyst systems, include alkanes, alkenes, cycloalkanes, selected halogenated hydrocarbons, aromatic hydrocarbons, and in some cases, hydrofluorocarbons. Useful solvents specifically include hexane, toluene, cyclohexane, and benzene.

The instant invention may also be used to obtain mixtures of olefins containing desirable numbers of carbon atoms. Factor K from the Schulz-Flory theory (see for instance B. Elvers, et al., Ed. Ullmann's Encyclopedia of Industrial Chemistry, Vol. A13, VCH Verlagsgesellschaft mbH, Weinheim, 1989, p. 243–247 and 275–276) serves as a measure of these olefins' molecular weights. From this theory, K=n ($C_{n+2}$ olefin)/n($C_n$ olefin), where n($C_n$ olefin) is the number of moles of olefin containing n carbon atoms, and n($C_{n+2}$ olefin) is the number of moles of olefin containing n+2 carbon atoms, or in other words the next higher oligomer of $C_n$ olefin. From this can be determined the weight (mass) fractions of the various olefins in the resulting product. The ability to vary this factor provides the ability to choose the then-desired olefins.

Invention-made olefins may be further polymerized with other olefins to form more oligomers or even form homopolymers and copolymers of the alpha olefins produced. These polymers may be made by a number of known methods, such as Ziegler-Natta-type polymerization, metallocene catalyzed polymerization, and other methods, see for instance WO 96/23010, see for instance Angew. Chem., Int. Ed. Engl., vol. 34, p. 1143–1170 (1995); European Patent Application, 416,815; and U.S. Pat. No. 5,198,401 for information about metallocene-type catalysts, and J. Boor Jr., Ziegler-Natta Catalysts and Polymerizations, Academic Press, New York, 1979 and G. Allen, et al., Ed., Comprehensive Polymer Science, Vol. 4, Pergamon Press, Oxford, 1989, pp. 1–108, 409–412 and 533–584, for information about Ziegler-Natta-type catalysts, and H. Mark, et al., Ed., Encyclopedia of Polymer Science and Engineering, Vol. 6, John Wiley & Sons, New York, 1992, p. 383–522, for information about polyethylene.

Preferred oligomerization processes include oligomerizing ethylene to $C_4$–$C_{26}$ linear alpha-olefins.

Oligomers produced herein may be used as polyolefin feed stocks. They may be used as a mixture of olefins alone, as a mixture of olefins added to other olefins, or they may be separated into fractions and then used alone or in combination with other olefins to form polyolefins. Additionally, alpha-olefins produced herein may be converted to alcohols by known processes, these alcohols being useful for a variety of applications such as intermediates for detergents or plasticizers. Typical processes for the conversion of alpha-olefins to alcohols include, but are not limited to the oxo process followed by hydrogenation, or by a modified, single-step oxo process (the modified Shell process), see for instance B. Elvers, et al., Ed., Ullmann's Encyclopedia of Chemical Technology, 5th Ed., Vol. A18, VCH Verlagsgesellschaft mbH, Weinheim, 1991, p. 321–327.

EXAMPLES

Preparation of Ligands

The electrospray (ES) mass spectra were recorded using a micromass Quattra LC mass spectrometer with methanol as the matrix [Masslynx software; open-access autosampler injection]. The infrared spectra were recorded as Nujol mulls between 0.5 mm NaCl plates on a Perkin Elmer 1600 series. $^1$H and $^{13}$C NMR spectra were recorded on a Bruker ARX spectrometer 250/300 Hz; chemical shifts (ppm) are referred to the residual protic solvent peaks. The reagents including sodium t-butoxide, potassium carbonate, the aryl bromides, 2-picolyl chloride hydrochloride and diethylenetriamine were purchased from Aldrich Chemical Co. and used without further purification. rac-BINAP (rac 2,2'-bis(diphenylphosphino)-1,1'binaphthyl) was purchased from Strem Chemical Co. The compounds, Pd$_2$(dba)$_3$ (tris(dibenzylideneacetone)dipalladium(0)) used as the chloroform solvate [1], (H$_2$NCH$_2$CH$_2$)$_2${(2-C$_5$H$_4$N)CH$_2$}N [bis(2-aminoethyl) (2-picolyl)amine] [2], (H$_2$NCH$_2$CH$_2$)$_2$NMe [N-methyldiethylenetriamine] [3] and {(2,4,6-Me$_3$C$_6$H$_2$) HNCH$_2$CH$_2$}$_2$NH [bis(N-2,4,6-trimethylphenyl-2-aminoethyl)amine] (1b) [4] were prepared according to previously reported procedures. Pd$_2$(dba)$_3$ can also be purchased from Strem Chemical Co. All other chemicals were obtained commercially and used without further purification.

[1] T. Ukai, H. Kawazura, Y. Ishii, J. Bonnet and J. A. Ibers, *J. Organomet. Chem.*, 1974, 65, 253. [2] M. E. G. Skinner, D. A. Cowhig and P. Mountford, *Chem. Commun.*, 2000, 1167. [3] G. Riggio, H. Wolfgang, A. A. Hofmann and P. G. Waser, *Helv. Chim. Acta*, 1980, 63, 488. [4] L.-C. Liang, R. R. Schrock, W. M. Davis and D. H. McConville, *J. Am. Chem. Soc.*, 1999, 121, 5797.

Examples 1–6

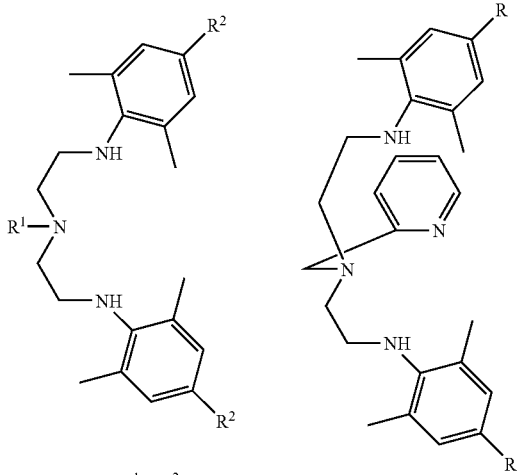

Example 1 (1a) $R^1 = R^2 = H$
Example 2 (1b) $R^1 = H, R^2 = Me$
Example 3 (1c) $R^1 = Me, R^2 = H$
Example 4 (1d) $R^1 = R^2 = Me$ Example 5 (2a) R = H
Example 6 (2b) R = Me Example 1

Preparation of bis(N-2,6-dimethylphenyl-2-aminoethyl)amine (1a)

A schlenk flask was charged with diethylenetriamine (1.06 g, 10.3 mmol), 2-bromo-m-xylene (2.74 cm$^3$, 3.81 g, 20.6 mmol), Pd$_2$(dba)$_3$ (0.047 g, 0.052 mmol, 0.005 eq.), rac-BINAP (0.096 g, 0.155 mmol, 0.015 eq.), NaOBu$^t$ (2.97 g, 30.9 mmol) and toluene (40 cm$^3$). The reaction mixture was heated to 100° C. and stirred for a period of four days. After cooling to room temperature, the solvent was removed under reduced pressure to afford an oily residue. The residue was dissolved in diethyl ether (30 cm$^3$) and washed with water (3×30 cm$^3$) and saturated sodium chloride solution (3×30 cm$^3$). The organic layer was separated and dried over magnesium sulfate. The solvent was removed under reduced pressure and the residue left under vacuum at 70° C. for 24 h to give {(2,6-Me$_2$C$_6$H$_3$)HNCH$_2$CH$_2$}$_2$NH (1a) as a viscous oil (2.40 g, 75%).

Compound 1a: ES mass spectrum, m/z 312 (M$^+$+H)$^+$; IR (nujol mull, cm$^{-1}$), 3358 (N—H, medium); NMR (CDCl$_3$, 293 K): $^1$H NMR, δ 6.91 (d, 4H, Ar—H$_m$), 6.76 (t, 2H, Ar—H$_p$), 3.05 (t, 4H, CH$_2$), 2.80 (t, 4H, CH$_2$) and 2.21 (s, 12H, Me$_o$); $^{13}$C ($^1$H composite pulse decoupled) NMR, δ 150.0 (s, Ar), 129.1 (s, Ar), 129.1 (s, Ar), 122.0 (s, Ar), 58.3 (s, CH$_2$), 46.3 (s, CH$_2$) and 19.3 (s, Me$_o$).

Example 2

Preparation of bis(N-2,4,6-trimethylphenyl-2-aminoethyl)amine (1b)

Compound {(2,4,6-Me$_3$C$_6$H$_2$)HNCH$_2$CH$_2$}$_2$NH (1b) was prepared using the procedure previously described in ref. 4 (JACS, 1999, 121, 5797) using diethylenetriamine (1.06 g, 10.3 mmol), 2-bromomesitylene (3.15 cm$^3$, 4.10 g, 20.6 mmol), Pd$_2$(dba)$_3$ (0.047 g, 0.052 mmol, 0.005 eq.), rac-BINAP (0.096 g, 0.155 mmol, 0.015 eq.), NaOBu$^t$ (2.97 g, 30.9 mmol) in toluene (40 cm$^3$). The spectroscopic and analytical data for a sample of 1b obtained in this work were consistent with the reported results.

Example 3

Preparation of bis(N-2,6-dimethylphenyl-2-aminoethyl)methylamine (1c)

Compound {(2,6-Me$_2$C$_6$H$_3$)HNCH$_2$CH$_2$}$_2$NMe (1c) was prepared using an analogous route to that outlined for 1a using N-methyldiethylenetriamine (1.21 g, 10.3 mmol), 2-bromo-m-xylene (2.74 cm$^3$, 3.81 g, 20.6 mmol), Pd$_2$(dba)$_3$ (0.047 g, 0.052 mmol, 0.005 eq.), rac-BINAP (0.096 g, 0.155 mmol, 0.015 eq.), NaOBu$^t$ (2.97 g, 30.9 mmol) in toluene (40 cm$^3$). Compound 1c was obtained as a red oil in good yield (2.72 g, 81%).

Compound 1c: ES mass spectrum, m/z 326 (M+H)$^+$; IR (nujol mull, cm$^{-1}$), 3357 (N—H, medium); NMR (CDCl$_3$, 293 K): $^1$H NMR, δ 6.90 (d, 4H, Ar—H$_m$), 6.74 (t, 2H, Ar—H$_p$), 3.03 (t, 4H, CH$_2$), 2.55 (t, 4H, CH$_2$), 2.21 (s, 12H, Me$_o$) and 2.19 (s, 3H, N-Me); $^{13}$C ($^1$H composite pulse decoupled) NMR, δ 146.9 (s, Ar), 129.3 (s, Ar), 129.2 (s, Ar), 121.8 (s, Ar), 58.7 (s, CH$_2$), 46.1 (s, CH$_2$), 41.7 (s, N-Me) and 19.1 (s, Me$_o$).

Example 4

Preparation of bis(N-2,4,6-trimethylphenyl-2-aminoethyl)methylamine (1d)

Compound {(2,4,6-Me$_3$C$_6$H$_2$)HNCH$_2$CH$_2$}$_2$NMe (1d) was prepared using an analogous route to that outlined for 1a using N-methyldiethylenetriamine (1.21 g, 10.3 mmol), 2-bromomesitylene (3.15 cm$^3$, 4.10 g, 20.6 mmol), Pd$_2$(dba)$_3$ (0.047 g, 0.052 mmol, 0.005 eq.), rac-BINAP (0.096 g, 0.155 mmol, 0.015 eq.), NaOBu$^t$ (2.97 g, 30.9 mmol) in toluene (40 cm$^3$). Compound 1d was obtained as a red oil in good yield (2.88 g, 79%).

Compound 1d: ES mass spectrum, m/z 354 (M+H)$^+$; IR (nujol mull, cm$^{-1}$), 3357 (N—H, medium); NMR (CDCl$_3$, 293 K): $^1$H NMR, δ 6.84 (s, 4H, Ar—H), 3.04 (t, 4H, CH$_2$), 2.61 (t, 4H, CH$_2$), 2.28 (s, 12H, Me$_o$), 2.21 (s, 6H, Me$_o$) and 2.17 (s, 3H, N-Me); $^{13}$C ($^1$H composite pulse decoupled) NMR, δ 146.7 (s, Ar), 129.1 (s, Ar), 128.9 (s, Ar), 121.9 (s, Ar), 58.4 (s, CH$_2$), 46.3 (s, CH$_2$), 41.7 (s, N-Me), 20.7 (s, Me$_p$) and 19.1 (s, Me$_o$).

Example 5

Preparation of bis(N-2,6-dimethylphenyl-2-aminoethyl)(2-picolyl)amine (2a)

Compound {(2,6-Me$_2$C$_6$H$_3$)HNCH$_2$CH$_2$}$_2${(2-C$_5$H$_4$N)CH$_2$}N (2a) was prepared by two alternative routes (1 and 2 outlined below).

Route 1: A schlenk flask was charged with bis(2-aminoethyl)(2-picolyl)amine (1.00 g, 5.15 mol), 2-bromo-m-xylene (1.37 cm$^3$, 1.91 g, 10.3 mmol), Pd$_2$(dba)$_3$ (0.024 g, 0.026 mmol, 0.0025 eq.), rac-BINAP (0.048 g, 0.078 mmol, 0.075 eq.), NaOBu$^t$ (1.49 g, 15.45 mmol) and toluene (20 cm$^3$). The reaction mixture was heated to 100° C. and stirred for a period of four days. After cooling to room temperature, the solvent was removed under reduced pressure to afford an oily residue. The residue was dissolved in diethyl ether (30 cm$^3$) and washed with water (3×30 cm$^3$) and saturated sodium chloride solution (3×30 cm$^3$). The organic layer was separated and dried over magnesium sulfate. The solvent was removed under reduced pressure and the residue left under vacuum at 70° C. for 24 h to give 2a as a viscous oil (1.43 g, 69%).

Route 2: A schlenk flask was charged with 1a (0.50 g, 1.61 mmol), 2-picolyl chloride hydrochloride (0.397 g, 2.42 mmol), K$_2$CO$_3$ (0.68 g, 4.83 mmol) and acetonitrile (40 cm$^3$). The reaction mixture was heated to 55° C. and stirred for a period of three days. After cooling to room temperature, the solution was filtered and the solvent removed under reduced pressure to afford an oily residue. The residue was dissolved in diethyl ether (30 cm$^3$) and washed with water (3×30 cm$^3$). The organic layer was separated and dried over magnesium sulfate. The solvent was removed under reduced pressure and the residue left under vacuum at 70° C. for 24 h to give 2a as a viscous oil (0.45 g, 69%).

Compound 2a: ES mass spectrum, m/z 403 [M+H]$^+$; IR (nujol mull, cm$^{-1}$), 3356 (N—H, medium); NMR (CDCl$_3$, 293 K): $^1$H NMR, δ 8.5–7.1 (m, 4H, Py-H), 6.91 (m, 4H, Ar—H$_m$), 6.71 (m, 2H, Ar—H$_p$), 3.86 (s, 2H, Py-CH$_2$), 3.03 (t, 4H, $^3J_{H-H}$ 5.7 Hz, CH$_2$), 2.77 (t, 4H, $^3J_{H-H}$ 5.7 Hz, CH$_2$) and 2.20 (s, 12H, Me$_o$); $^{13}$C ($^1$H composite pulse decoupled) NMR, δ 160.3 (s, Py), 149.7 (s, Py), 146.8 (s, Ar), 136.9 (s, Py), 129.7 (s, Ar), 129.2 (s, Ar), 122.6 (s, Ar), 122.4 (s, Py), 121.9 (s, Py), 55.4 (s, Py-CH$_2$), 50.1 (s, CH$_2$), 48.3 (s, CH$_2$) and 18.9 (s, Me$_o$).

Example 6

Preparation of bis(N-2,4,6-trimethylphenyl-2-aminoethyl)(2-picolyl)amine (2b)

As with 2a, compound {(2,4,6-Me$_3$C$_6$H$_2$)HNCH$_2$CH$_2$}$_2${(2-C$_5$H$_4$N)CH$_2$}N (2b) was prepared by two alternative routes.

Route 1: The procedure described for the preparation of 2a (route 1) was employed using bis(2-aminoethyl)(2-picolyl)amine (1.00 g, 5.15 mmol), 2-bromomesitylene (1.58 cm$^3$, 2.05 g, 10.3 mmol), Pd$_2$(dba)$_3$ (0.024 g, 0.026 mmol, 0.0025 eq.), rac-BINAP (0.048 g, 0.078 mmol, 0.075 eq.), NaOBu$^t$ (1.49 g, 15.45 mmol) in toluene (20 cm$^3$). Compound 2b was obtained as a red oil in good yield (1.61 g, 73%).

Route 2: The procedure described for the preparation of 2a (route 2) was employed using 1b (0.54 g, 1.61 mmol), 2-picolyl chloride hydrochloride (0.397 g, 2.42 mmol), K$_2$CO$_3$ (0.68 g, 4.83 mmol) in acetonitrile (40 cm$^3$). Compound 2b was obtained as a red oil in good yield (0.47 g, 69%).

Compound 2b: ES mass spectrum, m/z 431 [M+H]$^+$; IR (nujol mull, cm$^{-1}$), 3357 (N—H, medium); NMR (CDCl$_3$, 293 K): $^1$H NMR, δ 8.7–7.1 (m, 4H, Py-H), 6.83 (s, 4H, Ar—H), 3.98 (s, 2H, Py-CH$_2$, 2H), 3.10 (t, 4H, CH$_2$), 2.89 (t, 4H, CH$_2$), 2.28 (s, 12H, Me$_o$) and 2.20 (s, 6H, Me$_p$); $^{13}$C ($^1$H composite pulse decoupled) NMR, δ 159.9 (s, Py), 149.4 (s, Py), 143.8 (s, Ar), 136.5 (s, Py), 129.5 (s, Ar), 129.1 (s, Ar), 122.2 (s, Py), 122.1 (s, Py), 122.0 (s, Ar), 55.0 (s, CH$_2$), 49.8 (s, CH$_2$), 48.4 (s, CH$_2$), 20.6 (s, Me$_p$) and 18.5 (s, Me$_o$).

Preparation of Complexes

All complexes were prepared under an atmosphere of dry, oxygen-free nitrogen, using standard Schlenk techniques or in a nitrogen purged glove box. n-Butanol was dried and deoxygenated by distillation over sodium metal under nitrogen. The metal dichlorides were purchased from Aldrich Chemical Co. and used without any further purification. FAB mass spectra were recorded using a Kratos Concept spectrometer with NBA (nitrobenzyl alcohol) as the matrix [samples placed on the end of probe within matrix and bombarded with xenon atoms at ca. 7 kV; Mach3 software, probe temperature 50° C.]. Magnetic Susceptibility studies were performed using an Evans Balance (Johnson Matthey) at room temperature. Elemental analyses were performed by S. Boyer at the Department of Chemistry, University of North London (UK). Data for the crystal structure determinations were collected on a Bruker APEX 2000 CCD diffractometer and solved using SHELXTL version 6.10.

Examples 7–12

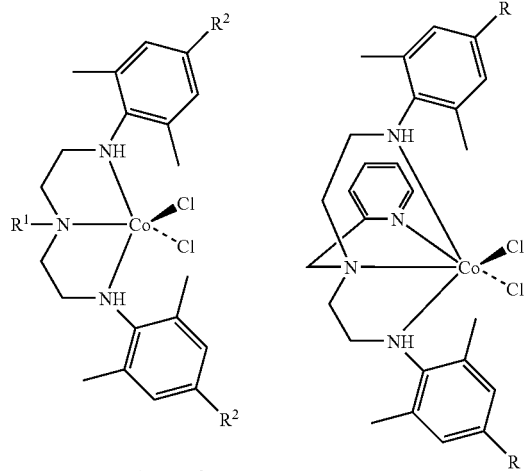

Example 7 (3a) R$^1$ = H, R$^2$ = H
Example 8 (3b) R$^1$ = H, R$^2$ = Me
Example 9 (3c) R$^1$ = Me, R$^2$ = H
Example 10 (3d) R$^1$ = R$^2$ = Me Example 11 (4a) R = H
Example 12 (4b) R = Me

Example 7

Preparation of [bis(N-2,6-dimethylphenyl-2-amino-ethyl)amine]cobalt dichloride (3a)

A solution of 1a (0.100 g, 0.32 mmol) in n-butanol (2 cm$^3$) was added dropwise to a solution of CoCl$_2$ (0.042 g, 0.32 mmol) in n-butanol (5 cm$^3$) at 90° C. to yield a green solution. After being stirred at 90° C. for 1 h, the reaction was allowed to cool to room temperature. The reaction mixture was concentrated and hexane added to induce precipitation of the product as a pale blue solid. The suspension was stirred overnight, filtered, washed with hexane (2×30 cm$^3$) and dried under reduced pressure to afford 3a as a pale blue solid (0.11 g, 80%).

Complex 3a: FAB mass spectrum, m/z 441 [M]$^+$, 406 [M-Cl]$^+$; IR (nujol mull, cm$^{-1}$), 3156 (N—H, weak); $\mu_{eff}$ (Evans Balance), 4.0 BM. C$_{20}$H$_{29}$N$_3$CoCl$_2$: calcd. C, 54.42; H, 6.58; N, 9.52. found C, 54.07; H, 6.53; N, 9.15%.

Layering of an acetonitrile solution of 3a with hexane gave crystals suitable for single crystal X-ray diffraction study (FIG. 1).

Example 8

Preparation of [bis(N-2,4,6-trimethylphenyl-2-aminoethyl)amine]cobalt dichloride (3b)

Complex 3b was prepared using an analogous route to that outlined for 3a using 1b (0.11 g, 0.32 mmol) and CoCl$_2$ (0.042 g, 0.32 mmol) in n-butanol. Compound 3b was obtained as a pale blue solid (0.12 g, 79%).

Complex 3b: FAB mass spectrum, m/z 469 [M]$^+$, 434 [M-Cl]$^+$; $\mu_{eff}$ (Evans Balance), 3.9 BM. C$_{22}$H$_{33}$N$_3$CoCl$_2$: calcd. C, 56.29; H, 7.04; N, 8.96. found C, 56.11; H, 6.99; N, 8.88%.

Layering of an acetonitrile solution of 3b with hexane gave crystals suitable for single crystal X-ray diffraction study (FIG. 2).

Example 9

Preparation of [bis(N-2,6-dimethylphenyl-2-aminoethyl)methylamine]cobalt dichloride (3c)

Complex 3c was prepared using an analogous route to that outlined for 3a using 1c (0.104 g, 0.32 mmol) and CoCl$_2$ (0.042 g, 0.32 mmol) in n-butanol. Compound 3c was obtained as a pale blue solid (0.11 g, 76%).

Complex 3c: FAB mass spectrum, m/z 455 [M]$^+$, 420 [M-Cl]$^+$; IR (nujol mull, cm$^{-1}$), 3335 (N—H, weak); $\mu_{eff}$ (Evans Balance), 4.0 BM. C$_{21}$H$_{31}$N$_3$CoCl$_2$: calcd. C 55.38; H, 6.81; N, 9.23. found C, 55.65; H, 7.02; N, 9.11%.

Layering of an acetonitrile solution of 3c with hexane gave crystals suitable for single crystal X-ray diffraction study (FIG. 3).

Example 10

Preparation of [bis(N-2,4,6-trimethylphenyl-2-aminoethyl)methylamine]cobalt dichloride (3d)

Complex 3d was prepared using an analogous route to that outlined for 3a using 1d (0.113 g, 0.32 mmol) and CoCl$_2$ (0.042 g, 0.32 mmol) in n-butanol. Complex 3d was obtained as a pale blue solid (0.11 g, 71%).

Complex 3d: FAB mass spectrum, m/z 483 [M]$^+$, 448 [M-Cl]$^+$; $\mu_{eff}$ (Evans Balance), 3.8 BM.

Example 11

Preparation of [bis(N-2,6-dimethylphenyl-2-aminoethyl)(2-picolyl)amine]cobalt dichloride (4a)

A solution of 2a (0.129 g, 0.32 mmol) in n-butanol (2 cm$^3$) was added dropwise to a solution of CoCl$_2$ (0.042 g, 0.32 mmol) in n-butanol (5 cm$^3$) at 90° C. to yield a green solution. After being stirred at 90° C. for 1 h, the reaction was allowed to cool to room temperature. The reaction mixture was concentrated and hexane added to induce precipitation of the product as a pale blue solid. The suspension was stirred overnight, filtered, washed with hexane (2×30 cm$^3$) and dried under reduced pressure to afford 4a as a pale blue solid. Recrystallization from hot acetonitrile gave 4a as pale blue blocks (0.12 g, 69%).

Complex 4a: FAB mass spectrum, m/z 532 [M]$^+$, 497 [M-Cl]$^+$; $\mu_{eff}$ (Evans Balance), 3.9 BM.

Example 12

Preparation of [bis(N-2,4,6-trimethylphenyl-2-aminoethyl)(2-picolyl)amine]cobalt dichloride (4b)

Complex 4b was prepared using an analogous route to that outlined for 4a using 2b (0.138 g, 0.32 mmol) and CoCl$_2$ (0.042 g, 0.32 mmol) in n-butanol. Complex 4b was obtained as a pale blue solid (0.13 g, 71%). Recrystallization of 4b could be achieved by the slow cooling of a hot acetonitrile solution of 4b.

Complex 4b: FAB mass spectrum, m/z 560 [M]$^+$, 525 [M-Cl]$^+$; $\mu_{eff}$ (Evans Balance), 3.8 BM. C$_{28}$H$_{38}$N$_4$CoCl$_2$: calcd. C, 60.00; H, 6.76; N, 10.00. found C, 60.13; H 6.94; N, 10.14%.

Layering of a dichloromethane solution of 4b with diethylether gave pale blue crystals suitable for a single crystal X-ray diffraction study (FIG. 4).

Oligomerizations

The reagents used in the oligomerization tests were Ethylene Grade 3.5 (supplied from BOC) and methylaluminoxane (MAO, 10% wt solution in toluene, supplied by Aldrich). GC measurements were obtained using an HP 5890 chromatogram [Column type SGE HT-5 (aluminum clad fused silica capillary); Column length 12 m; Column internal diameter 0.53 mm; Initial column temperature 55 C] with a flame ionization detector [FID (440 C)].

Example 13

Schlenk Tube Oligomerization

The complexes 3a and 3b made in Examples 7 and 8 above were dissolved or suspended in toluene (40 cm$^3$) and MAO introduced. The tube was purged with ethylene and the contents stirred under one bar ethylene at 25° C. for the duration of the oligomerization. After half an hour the oligomerization was terminated by the addition of aqueous hydrogen chloride. The aqueous phase was separated and washed with toluene (2×25 ml) and all organic layers combined and dried over anhydrous magnesium sulfate. The solutions were prepared for quantitative GC analysis by diluting the organic phases to 100 ml with toluene in a volumetric flask and adding 1-heptadecene (50 μl) as an internal standard. The runs are summarized in Table 2. FIG.

5 shows the Schulz-Flory distribution for runs 1 and 3 using pre-catalysts, 3a and 3c, respectively. FIG. 6 shows the oligomer distribution of oligomer fractions versus carbon number for runs 2 and 4 using pre-catalysts 3b and 3d, respectively.

TABLE 2

Schlenk test oligomerization runs.[a]

| Run | Precatalyst (mmol) | Activator[b] (mmol/equiv.) | Oligomers (g)[c] | Activity (g/mmol/h/bar) | K (α)[d] | β[e] |
|---|---|---|---|---|---|---|
| 1 | 3a (0.010) | MAO (4/400) | 0.206 | 41 | 0.74 | 0.35 |
| 2 | 3b (0.010) | MAO (4/400) | 0.198 | 40 | 0.74 | 0.35 |
| 3 | 3c (0.010) | MAO (4/400) | 0.168 | 34 | 0.76 | 0.32 |
| 4 | 3d (0.010) | MAO (4/400) | 0.279 | 56 | 0.74 | 0.35 |
| 5 | 4b (0.010) | MAO (4/400) | trace | trace | — | — |

[a]General Conditions: Toluene solvent (40 cm$^3$), 25 C., reaction time 30 min, ethylene pressure 1 bar, reaction quenched with dilute HCl;
[b]MAO = methylaluminoxane;
[c]Determined from GC using extrapolated values based on a Schulz-Flory distribution for C4–C8 and C22–C26 for runs 1–4 employing 1-heptadecene as an internal standard.
[d]K = α = n($C_{n+2}$ olefin)/n($C_n$ olefin), where n($C_n$ olefin) is the number of moles of olefin containing n carbon atoms, and n($C_{n+2}$ olefin) is the number of moles of olefin containing n + 2 carbon atoms, and is the rate of propagation over the sum of the rate of propagation and the rate of chain transfer.
[e]β = (1 − α)/α and is the rate of chain transfer over the rate of propagation.

All documents described herein are incorporated by reference herein, including any priority documents and testing procedures for all jurisdictions in which such incorporation is permitted. As is apparent from the foregoing general description and the specific embodiments, while forms of the invention have been illustrated and described, various modifications can be made without departing from the spirit and scope of the invention. Accordingly, it is not intended that the invention be limited thereby. Certain features of the present invention are described in terms of a set of numerical upper limits and a set of numerical lower limits. This specification discloses all ranges formed by any combination of these limits. All combinations of these limits are within the scope of the invention unless otherwise indicated.

We claim:

1. A transition metal catalyst compound for oligomerization of an unsaturated monomer represented by the formula: $LMX_2$ or the formula $(LMX_2)_2$ wherein
   each M is independently a Group 7, 8, 9 or 10 transition metal;
   each L is, independently, a tridentate or tetradentate neutrally charged ligand that is bonded to M by three or four nitrogen atoms, where at least one of the nitrogen atoms is a central nitrogen atom and at least two of the nitrogen atoms are terminal nitrogen atoms, and at least two terminal nitrogen atoms are substituted with one $C_3$–$C_{50}$ hydrocarbyl and one hydrogen atom or two hydrocarbyls wherein at least one hydrocarbyl is a $C_3$–$C_{50}$ hydrocarbyl, and the central nitrogen atom is bonded to three different carbon atoms or two different carbon atoms and one hydrogen atom; and
   each X is independently a monoanionic ligand, or two X may join together to form a bidentate dianionic ligand.

2. The composition of claim 1 wherein M comprises a group 9, or 10 transition metal.

3. The composition of claim 1 wherein M comprises one or more of nickel, cobalt, iron or manganese.

4. The composition of claim 1 wherein X is a hydride, hydrocarbyl, substituted hydrocarbyl, halocarbyl, substituted halocarbyl, or two X groups together are a hydrocarbdiyl, halocarbdiyl, substituted hydrocarbdiyl, or substituted halocarbdiyl.

5. The composition of claim 1 wherein X is selected from the group consisting of chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, methoxy, ethoxy, propoxy, butoxy, dimethylamido, diethylamido, methylethylamido, phenoxy, benzoxy, and allyl.

6. The composition of claim 1 wherein two X groups are joined and are selected from the group consisting of methylidene, ethylidene, propylidene, tetramethylene, pentamethylene, hexamethylene, butadiene, methylbutadiene, dimethylbutadiene, pentadiene, methylpentadiene, dimethylpentadiene, hexadiene, methylhexadiene, and dimethylhexadiene.

7. A catalyst system comprising the composition of claim 1 and an activator.

8. The catalyst system of claim 7 wherein the activator comprises an alumoxane.

9. The catalyst system of claim 7 wherein the activator comprises an alkyl aluminum compound.

10. The catalyst system of claim 7 wherein the activator comprises an ionizing or stoichiometric activator.

11. The catalyst system of claim 7 wherein the activator comprises one or more of:
   trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, di(isopropyl)ammonium tetraphenylborate, dicyclohexylammonium tetraphenylborate; tri(o-tolyl)phosphonium tetraphenylborate, tri(2,6-dimethylphenyl)phosphonium tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, di(isopropyl)ammonium tetrakis(pentafluorophenyl)borate, dicyclohexylammonium tetrakis(pentafluorophenyl)borate; tri(o-tolyl)phosphonium tetrakis(pentafluorophenyl)borate, tri(2,6-dimethylphenyl)phosphonium tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, di(isopropyl)ammonium tetrakis(2,3,4,6-tetrafluorophenyl)borate, dicyclohexylammonium tetrakis(2,3,4,6-tetrafluorophenyl)borate; tri(o-tolyl)phosphonium tetrakis(2,3,4,6-tetrafluorophenyl)borate, tri(2,6-dimethylphenyl)phosphonium tetrakis(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, di(isopropyl)ammonium tetrakis(pentafluoronaphthyl)borate, dicyclohexylammonium tetrakis(pentafluoronaphthyl)borate; tri(o-tolyl)phosphonium tetrakis(pentafluoronaphthyl)borate, tri(2,6-dimethylphenyl)phosphonium tetrakis(pentafluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, di(isopropyl)ammonium tetrakis(pentafluorobiphenyl)borate, dicyclohexylammonium tetrakis(pentafluorobiphenyl)borate; tri(o-tolyl)phosphonium tetrakis(pentafluorobiphenyl)borate, tri(2,6-dimethylphenyl)phosphonium tetrakis(pentafluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, di(isopropyl)ammonium tetrakis(3,5-bis(trifluoromethyl)phenyl)borate, dicyclohexylammonium tetrakis(3,5-bis(trifluoromethyl)phenyl)borate; tri(o-tolyl)phosphonium tetrakis(3,5-bis(trifluoromethyl)phenyl)borate, and tri(2,6-dimethylphenyl)phosphonium tetrakis(3,5-bis(trifluoromethyl)phenyl)borate.

12. The catalyst system of claim 7 wherein the transition metal catalyst compound is present on a support.

13. The catalyst system of claim 7 wherein the transition metal catalyst compound and the activator are present on a support.

14. The catalyst system of claim 12 wherein the support comprises one or more Group 2, 3, 4, 5, 13 or 14 metal oxides.

15. The catalyst system of claim 13 wherein the support comprises one or more Group 2, 3, 4, 5, 13 or 14 metal oxides.

16. The catalyst system of claim 12 wherein the support comprises one or more of silica, alumina, silica-alumina, magnesia, titania, zirconia, magnesium chloride, montmorillonite, phyllosilicate, zeolites, talc, clays, silica-chromium, silica-titania, porous acrylic polymers, nanocomposites, aerogels, spherulites, or polymeric beads.

17. The catalyst system of claim 13 wherein the support comprises one or more of silica, alumina, silica-alumina, magnesia, titania, zirconia, magnesium chloride, montmorillonite, phyllosilicate, zeolites, talc, clays, silica-chromium, silica-titania, porous acrylic polymers, nanocomposites, aerogels, spherulites, or polymeric beads.

18. The catalyst system of claim 12 wherein the support is silica.

19. The catalyst system of claim 13 wherein the support is silica.

20. The catalyst system of claim 12 wherein the activator is bound to the support prior to combination with the transition metal catalyst compound.

21. The catalyst system of claim 13 wherein the activator is bound to the support prior to combination with the transition metal catalyst compound.

22. The catalyst system of claim 18 wherein the activator is bound to the support prior to combination with the transition metal catalyst compound.

23. The catalyst system of claim 19 wherein the activator is bound to the support prior to combination with the transition metal catalyst compound.

24. A process to oligomerize unsaturated monomers comprising contacting monomers with the compound of claim 1.

25. A process to oligomerize unsaturated monomers comprising contacting monomers with the catalyst system of claim 7.

26. A process to oligomerize unsaturated monomers comprising contacting monomers with the catalyst system of claim 8.

27. A process to oligomerize unsaturated monomers comprising contacting monomers with the catalyst system of claim 9.

28. A process to oligomerize unsaturated monomers comprising contacting monomers with the catalyst system of claim 10.

29. A process to oligomerize unsaturated monomers comprising contacting monomers with the catalyst system of claim 11.

30. A process to oligomerize unsaturated monomers comprising contacting monomers with the catalyst system of claim 12.

31. A process to oligomerize unsaturated monomers comprising contacting monomers with the catalyst system of claim 13.

32. A process to oligomerize unsaturated monomers comprising contacting monomers with the catalyst system of claim 17.

33. A process to oligomerize unsaturated monomers comprising contacting monomers with the catalyst system of claim 19.

34. A process to oligomerize unsaturated monomers comprising contacting monomers with the catalyst system of claim 21.

35. The process of claim 24, wherein the monomer comprises one or more alpha-olefins.

36. The process of claim 24, wherein the monomer comprises one or more C2 to C40 alpha-olefins.

37. The process of claim 24, wherein the monomer comprises one or more C2 to C12 alpha-olefins.

38. The process of claim 24, wherein the monomer comprises one or more dienes.

39. A process to oligomerize an unsaturated monomer comprising contacting the monomer with a catalyst system comprising a transition metal catalyst compound combined with an activator, where the combination is selected from the group consisting of:

[bis(N-2,6-dimethylphenyl-2-aminoethyl)amine]cobalt dichloride/methylalumoxane,
[bis(N-2,4,6-trimethylphenyl-2-aminoethyl)amine]cobalt dichloride/methylalumoxane,
[bis(N-2,6-diisopropylphenyl-2-aminoethyl)amine]cobalt dichloride/methylalumoxane,
[bis(N-2,4,6-triisopropylphenyl-2-aminoethyl)amine]cobalt dichloride/methylalumoxane,
[bis(N-2,6-diisopropyl-4-methylphenyl-2-aminoethyl)amine]cobalt dichloride/methylalumoxane,
[bis(N-2,6-diethylphenyl-2-aminoethyl)amine]cobalt dichloride/methylalumoxane,
[bis(N-2,6-dimethylphenyl-2-aminoethyl)(2-picolyl)amine]cobalt dichloride/methylalumoxane,
[bis(N-2,4,6-trimethylphenyl-2-aminoethyl)(2-picolyl)amine]cobalt dichloride/methylalumoxane,
[bis(N-2,6-diisopropylphenyl-2-aminoethyl)(2-picolyl)amine]cobalt dichloride/methylalumoxane,
[bis(N-2,4,6-triisopropylphenyl-2-aminoethyl)(2-picolyl)amine]cobalt dichloride/methylalumoxane,
[bis(N-2,6-diisopropyl-4-methylphenyl-2-aminoethyl)(2-picolyl)amine]cobalt dichloride/methylalumoxane,
[bis(N-2,6-diethylphenyl-2-aminoethyl)(2-picolyl)amine]cobalt dichloride/methylalumoxane,
[bis(N-2,6-dimethylphenyl-2-aminoethyl)methylamine]cobalt dichloride/methylalumoxane,
[bis(N-2,4,6-trimethylphenyl-2-aminoethyl)methylamine]cobalt dichloride/methylalumoxane,
[bis(N-2,6-diisopropylphenyl-2-aminoethyl)methylamine]cobalt dichloride/methylalumoxane,
[bis(N-2,4,6-triisopropylphenyl-2-aminoethyl)methylamine]cobalt dichloride/methylalumoxane,
[bis(N-2,6-diisopropyl-4-methylphenyl-2-aminoethyl)methylamine]cobalt dichloride/methylalumoxane,
[bis(N-2,6-diethylphenyl-2-aminoethyl)methylamine]cobalt dichloride/methylalumoxane,
[bis(N-2,6-dimethylphenyl-2-aminoethyl)amine]cobalt dibromide/methylalumoxane,
[bis(N-2,4,6-trimethylphenyl-2-aminoethyl)amine]cobalt dibromide/methylalumoxane,
[bis(N-2,6-dimethylphenyl-2-aminoethyl)(2-picolyl)amine]cobalt dibromide/methylalumoxane,
[bis(N-2,4,6-trimethylphenyl-2-aminoethyl)(2-picolyl)amine]cobalt dibromide/methylalumoxane,
[bis(N-2,6-dimethylphenyl-2-aminoethyl)methylamine]cobalt dibromide/methylalumoxane,
[bis(N-2,4,6-trimethylphenyl-2-aminoethyl)methylamine]cobalt dibromide/methylalumoxane,
[bis(N-2,6-dimethylphenyl-2-aminoethyl)amine]cobalt dimethyl/methylalumoxane,
[bis(N-2,4,6-trimethylphenyl-2-aminoethyl)amine]cobalt dimethyl/methylalumoxane,
[bis(N-2,6-dimethylphenyl-2-aminoethyl)methylamine]cobalt dimethyl/methylalumoxane,
[bis(N-2,4,6-trimethylphenyl-2-aminoethyl)methylamine]cobalt dimethyl/methylalumoxane,
[bis(N-2,6-dimethylphenyl-2-aminoethyl)(2-picolyl)amine]cobalt dimethyl/methylalumoxane,
[bis(N-2,4,6-trimethylphenyl-2-aminoethyl)(2-picolyl)amine]cobalt dimethyl/methylalumoxane,
[bis(N-2,6-dimethylphenyl-2-aminoethyl)amine]iron dichloride/methylalumoxane,
[bis(N-2,4,6-trimethylphenyl-2-aminoethyl)amine]iron dichloride/methylalumoxane,
[bis(N-2,6-diisopropylphenyl-2-aminoethyl)amine]iron dichloride/methylalumoxane,
[bis(N-2,4,6-triisopropylphenyl-2-aminoethyl)amine]iron dichloride/methylalumoxane,
[bis(N-2,6-diisopropyl-4-methylphenyl-2-aminoethyl)amine]iron dichloride/methylalumoxane,
[bis(N-2,6-diethylphenyl-2-aminoethyl)amine]iron dichloride/methylalumoxane,
[bis(N-2,6-dimethylphenyl-2-aminoethyl)methylamine]iron dichloride/methylalumoxane,
[bis(N-2,4,6-trimethylphenyl-2-aminoethyl)methylamine]iron dichloride/methylalumoxane,
[bis(N-2,6-diisopropylphenyl-2-aminoethyl)methylamine]iron dichloride/methylalumoxane,
[bis(N-2,4,6-triisopropylphenyl-2-aminoethyl)methylamine]iron dichloride/methylalumoxane,
[bis(N-2,6-diisopropyl-4-methylphenyl-2-aminoethyl)methylamine]iron dichloride/methylalumoxane,
[bis(N-2,6-diethylphenyl-2-aminoethyl)methylamine]iron dichloride/methylalumoxane,
[bis(N-2,6-dimethylphenyl-2-aminoethyl)(2-picolyl)amine]iron dichloride/methylalumoxane,
[bis(N-2,4,6-trimethylphenyl-2-aminoethyl)(2-picolyl)amine]iron dichloride/methylalumoxane,
[bis(N-2,6-diisopropylphenyl-2-aminoethyl)(2-picolyl)amine]iron dichloride/methylalumoxane,
[bis(N-2,4,6-triisopropylphenyl-2-aminoethyl)(2-picolyl)amine]iron dichloride/methylalumoxane,
[bis(N-2,6-diisopropyl-4-methylphenyl-2-aminoethyl)(2-picolyl)amine]iron dichloride/methylalumoxane,
[bis(N-2,6-diethylphenyl-2-aminoethyl)(2-picolyl)amine]iron dichloride/methylalumoxane,
[bis(N-2,6-dimethylphenyl-2-aminoethyl)amine]manganese dichloride/methylalumoxane,

[bis(N-2,4,6-trimethylphenyl-2-aminoethyl)amine]manganese dichloride/methylalumoxane,
[bis(N-2,6-diisopropylphenyl-2-aminoethyl)amine]manganese dichloride/methylalumoxane,
[bis(N-2,4,6-triisopropylphenyl-2-aminoethyl)amine]manganese dichloride/methylalumoxane,
[bis(N-2,6-diisopropyl-4-methylphenyl-2-aminoethyl)amine]manganese dichloride/methylalumoxane,
[bis(N-2,6-diethylphenyl-2-aminoethyl)methylamine]manganese dichloride/methylalumoxane,
[bis(N-2,6-dimethylphenyl-2-aminoethyl)methylamine]manganese dichloride/methylalumoxane,
[bis(N-2,4,6-trimethylphenyl-2-aminoethyl)methylamine]manganese dichloride/methylalumoxane,
[bis(N-2,6-diisopropylphenyl-2-aminoethyl)methylamine]manganese dichloride/methylalumoxane,
[bis(N-2,4,6-triisopropylphenyl-2-aminoethyl)methylamine]manganese dichloride/methylalumoxane,
[bis(N-2,6-diisopropyl-4-methylphenyl-2-aminoethyl)methylamine]manganese dichloride/methylalumoxane,
[bis(N-2,6-diethylphenyl-2-aminoethyl)methylamine]manganese dichloride/methylalumoxane,
[bis(N-2,6-diethylphenyl-2-aminoethyl)(2-picolyl)amine]manganese dichloride/methylalumoxane,
[bis(N-2,4,6-triethylphenyl-2-aminoethyl)(2-picolyl)amine]manganese dichloride/methylalumoxane,
[bis(N-2,6-dimethylphenyl-2-aminoethyl)(2-picolyl)amine]manganese dichloride/methylalumoxane,
[bis(N-2,4,6-trimethylphenyl-2-aminoethyl)(2-picolyl)amine]manganese dichloride/methylalumoxane,
[bis(N-2,6-diisopropylphenyl-2-aminoethyl)(2-picolyl)amine]manganese dichloride/methylalumoxane,
[bis(N-2,4,6-triisopropylphenyl-2-aminoethyl)(2-picolyl)amine]manganese dichloride/methylalumoxane,
[bis(N-2,6-diisopropyl-4-methylphenyl-2-aminoethyl)(2-picolyl)amine]manganese dichloride/methylalumoxane,
[bis(N-2,6-diethylphenyl-2-aminoethyl)(2-picolyl)amine]manganese dichloride/methylalumoxane,
[bis(N-2,6-dimethylphenyl-2-aminoethyl)amine]nickel dichloride/methylalumoxane,
[bis(N-2,4,6-trimethylphenyl-2-aminoethyl)amine]nickel dichloride/methylalumoxane,
[bis(N-2,6-diisopropylphenyl-2-aminoethyl)amine]nickel dichloride/methylalumoxane,
[bis(N-2,4,6-triisopropylphenyl-2-aminoethyl)amine] nickel dichloride/methylalumoxane,
[bis(N-2,6-diisopropyl-4-methylphenyl-2-aminoethyl)amine]nickel dichloride/methylalumoxane,
[bis(N-2,6-diethylphenyl-2-aminoethyl)amine]nickel dichloride/methylalumoxane,
[bis(N-2,6-dimethylphenyl-2-aminoethyl)methylamine]nickel dichloride/methylalumoxane,
[bis(N-2,4,6-trimethylphenyl-2-aminoethyl)methylamine]nickel dichloride/methylalumoxane,
[bis(N-2,6-diisopropylphenyl-2-aminoethyl)methylamine]nickel dichloride/methylalumoxane,
[bis(N-2,4,6-triisopropylphenyl-2-aminoethyl)methylamine]nickel dichloride/methylalumoxane,
[bis(N-2,6-diisopropyl-4-methylphenyl-2-aminoethyl)methylamine]nickel dichloride/methylalumoxane,
[bis(N-2,6-diethylphenyl-2-aminoethyl)methylamine]nickel dichloride/methylalumoxane,
[bis(N-2,6-dimethylphenyl-2-aminoethyl)(2-picolyl)amine]nickel dichloride/methylalumoxane,
[bis(N-2,4,6-trimethylphenyl-2-aminoethyl)(2-picolyl)amine]nickel dichloride/methylalumoxane,
[bis(N-2,6-diisopropylphenyl-2-aminoethyl)(2-picolyl)amine]nickel dichloride/methylalumoxane,
[bis(N-2,4,6-triisopropylphenyl-2-aminoethyl)(2-picolyl)amine]nickel dichloride/methylalumoxane,
[bis(N-2,6-diisopropyl-4-methylphenyl-2-aminoethyl)(2-picolyl)amine]nickel dichloride/methylalumoxane,
[bis(N-2,6-diethylphenyl-2-aminoethyl)(2-picolyl)amine]nickel dichloride/methylalumoxane,
[bis(N-2,6-dimethylphenyl-2-aminoethyl)amine]copper dichloride/methylalumoxane,
[bis(N-2,4,6-trimethylphenyl-2-aminoethyl)amine]copper dichloride/methylalumoxane,
[bis(N-2,6-diisopropylphenyl-2-aminoethyl)amine]copper dichloride/methylalumoxane,
[bis(N-2,6-dimethylphenyl-2-aminoethyl)methylamine] copper dichloride/methylalumoxane,
[bis(N-2,4,6-trimethylphenyl-2-aminoethyl)methylamine]copper dichloride/methylalumoxane,
[bis(N-2,6-diisopropylphenyl-2-aminoethyl)methylamine]copper dichloride/methylalumoxane,
[bis(N-2,6-dimethylphenyl-2-aminoethyl)(2-picolyl)amine]copper dichloride/methylalumoxane,
[bis(N-2,4,6-trimethylphenyl-2-aminoethyl)(2-picolyl)amine]copper dichloride/methylalumoxane,
[bis(N-2,6-diisopropylphenyl-2-aminoethyl)(2-picolyl)amine]copper dichloride/methylalumoxane,
[bis(N-2,6-dimethylphenyl-2-aminoethyl)amine]cobalt dichloride/modified methylalumoxane,
[bis(N-2,4,6-trimethylphenyl-2-aminoethyl)amine]cobalt dichloride/modified methylalumoxane,
[bis(N-2,6-diisopropylphenyl-2-aminoethyl)amine]cobalt dichloride/modified methylalumoxane,
[bis(N-2,4,6-triisopropylphenyl-2-aminoethyl)amine]cobalt dichloride/modified methylalumoxane,
[bis(N-2,6-diisopropyl-4-methylphenyl-2-aminoethyl)amine]cobalt dichloride/modified methylalumoxane,
[bis(N-2,6-diethylphenyl-2-aminoethyl)amine]cobalt dichloride/modified methylalumoxane,
[bis(N-2,6-dimethylphenyl-2-aminoethyl)(2-picolyl)amine]cobalt dichloride/modified methylalumoxane,
[bis(N-2,4,6-trimethylphenyl-2-aminoethyl)(2-picolyl)amine]cobalt dichloride/modified methylalumoxane,
[bis(N-2,6-diisopropylphenyl-2-aminoethyl)(2-picolyl)amine]cobalt dichloride/modified methylalumoxane,
[bis(N-2,4,6-triisopropylphenyl-2-aminoethyl)(2-picolyl)amine]cobalt dichloride/modified methylalumoxane,
[bis(N-2,6-diisopropyl-4-methylphenyl-2-aminoethyl)(2-picolyl)amine]cobalt dichloride/modified methylalumoxane,
[bis(N-2,6-diethylphenyl-2-aminoethyl)(2-picolyl)amine]cobalt dichloride/modified methylalumoxane,
[bis(N-2,6-dimethylphenyl-2-aminoethyl)methylamine]cobalt dichloride/modified methylalumoxane,
[bis(N-2,4,6-trimethylphenyl-2-aminoethyl)methylamine]cobalt dichloride/modified methylalumoxane,
[bis(N-2,6-diisopropylphenyl-2-aminoethyl)methylamine]cobalt dichloride/modified methylalumoxane,
[bis(N-2,4,6-triisopropylphenyl-2-aminoethyl)methylamine]cobalt dichloride/modified methylalumoxane,
[bis(N-2,6-diisopropyl-4-methylphenyl-2-aminoethyl)methylamine]cobalt dichloride/modified methylalumoxane,
[bis(N-2,6-diethylphenyl-2-aminoethyl)methylamine]cobalt dichloride/modified methylalumoxane,
[bis(N-2,6-dimethylphenyl-2-aminoethyl)amine]cobalt dibromide/modified methylalumoxane,

[bis(N-2,4,6-trimethylphenyl-2-aminoethyl)amine]cobalt dibromide/modified methylalumoxane,
[bis(N-2,6-dimethylphenyl-2-aminoethyl)(2-picolyl)amine]cobalt dibromide/modified methylalumoxane,
[bis(N-2,4,6-trimethylphenyl-2-aminoethyl)(2-picolyl)amine]cobalt dibromide/modified methylalumoxane,
[bis(N-2,6-dimethylphenyl-2-aminoethyl)methylamine]cobalt dibromide/modified methylalumoxane,
[bis(N-2,4,6-trimethylphenyl-2-aminoethyl)methylamine]cobalt dibromide/modified methylalumoxane,
[bis(N-2,6-dimethylphenyl-2-aminoethyl)amine]cobalt dimethyl/modified methylalumoxane,
[bis(N-2,4,6-trimethylphenyl-2-aminoethyl)amine]cobalt dimethyl/modified methylalumoxane,
[bis(N-2,6-dimethylphenyl-2-aminoethyl)methylamine]cobalt dimethyl/modified methylalumoxane,
[bis(N-2,4,6-trimethylphenyl-2-aminoethyl)methylamine]cobalt dimethyl/modified methylalumoxane,
[bis(N-2,6-dimethylphenyl-2-aminoethyl)(2-picolyl)amine]cobalt dimethyl/modified methylalumoxane,
[bis(N-2,4,6-trimethylphenyl-2-aminoethyl)(2-picolyl)amine]cobalt dimethyl/modified methylalumoxane,
[bis(N-2,6-dimethylphenyl-2-aminoethyl)amine]iron dichloride/modified methylalumoxane,
[bis(N-2,4,6-trimethylphenyl-2-aminoethyl)amine]iron dichloride/modified methylalumoxane,
[bis(N-2,6-diisopropylphenyl-2-aminoethyl)amine]iron dichloride/modified methylalumoxane,
[bis(N-2,4,6-triisopropylphenyl-2-aminoethyl)amine]iron dichloride/modified methylalumoxane,
[bis(N-2,6-diisopropyl-4-methylphenyl-2-aminoethyl)amine]iron dichloride/modified methylalumoxane,
[bis(N-2,6-diethylphenyl-2-aminoethyl)amine]iron dichloride/modified methylalumoxane,
[bis(N-2,6-dimethylphenyl-2-aminoethyl)methylamine]iron dichloride/modified methylalumoxane,
[bis(N-2,4,6-trimethylphenyl-2-aminoethyl)methylamine]iron dichloride/modified methylalumoxane,
[bis(N-2,6-diisopropylphenyl-2-aminoethyl)methylamine]iron dichloride/modified methylalumoxane,
[bis(N-2,4,6-triisopropylphenyl-2-aminoethyl)methylamine]iron dichloride/modified methylalumoxane,
[bis(N-2,6-diisopropyl-4-methylphenyl-2-aminoethyl)methylamine]iron dichloride/modified methylalumoxane,
[bis(N-2,6-diethylphenyl-2-aminoethyl)methylamine]iron dichloride/modified methylalumoxane,
[bis(N-2,6-dimethylphenyl-2-aminoethyl)(2-picolyl)amine]iron dichloride/modified methylalumoxane,
[bis(N-2,4,6-trimethylphenyl-2-aminoethyl)(2-picolyl)amine]iron dichloride/modified methylalumoxane,
[bis(N-2,6-diisopropylphenyl-2-aminoethyl)(2-picolyl)amine]iron dichloride/modified methylalumoxane,
[bis(N-2,4,6-triisopropylphenyl-2-aminoethyl)(2-picolyl)amine]iron dichloride/modified methylalumoxane,
[bis(N-2,6-diisopropyl-4-methylphenyl-2-aminoethyl)(2-picolyl)amine]iron dichloride/modified methylalumoxane,
[bis(N-2,6-diethylphenyl-2-aminoethyl)(2-picolyl)amine]iron dichloride/modified methylalumoxane,
[bis(N-2,6-dimethylphenyl-2-aminoethyl)amine]manganese dichloride/modified methylalumoxane,
[bis(N-2,4,6-trimethylphenyl-2-aminoethyl)amine]manganese dichloride/modified methylalumoxane,
[bis(N-2,6-diisopropylphenyl-2-aminoethyl)amine]manganese dichloride/modified methylalumoxane,
[bis(N-2,4,6-triisopropylphenyl-2-aminoethyl)amine]manganese dichloride/modified methylalumoxane,
[bis(N-2,6-diisopropyl-4-methylphenyl-2-aminoethyl)amine]manganese dichloride/modified methylalumoxane,
[bis(N-2,6-diethylphenyl-2-aminoethyl)methylamine]manganese dichloride/modified methylalumoxane,
[bis(N-2,6-dimethylphenyl-2-aminoethyl)methylamine]manganese dichloride/modified methylalumoxane,
[bis(N-2,4,6-trimethylphenyl-2-aminoethyl)methylamine]manganese dichloride/modified methylalumoxane,
[bis(N-2,6-diisopropylphenyl-2-aminoethyl)methylamine]manganese dichloride/modified methylalumoxane,
[bis(N-2,4,6-triisopropylphenyl-2-aminoethyl)methylamine]manganese dichloride/modified methylalumoxane,
[bis(N-2,6-diisopropyl-4-methylphenyl-2-aminoethyl)methylamine]manganese dichloride/modified methylalumoxane,
[bis(N-2,6-diethylphenyl-2-aminoethyl)methylamine]manganese dichloride/modified methylalumoxane,
[bis(N-2,6-diethylphenyl-2-aminoethyl)(2-picolyl)amine]manganese dichloride/modified methylalumoxane,
[bis(N-2,4,6-triethylphenyl-2-aminoethyl)(2-picolyl)amine]manganese dichloride/modified methylalumoxane,
[bis(N-2,6-dimethylphenyl-2-aminoethyl)(2-picolyl)amine]manganese dichloride/modified methylalumoxane,
[bis(N-2,4,6-trimethylphenyl-2-aminoethyl)(2-picolyl)amine]manganese dichloride/modified methylalumoxane,
[bis(N-2,6-diisopropylphenyl-2-aminoethyl)(2-picolyl)amine]manganese dichloride/modified methylalumoxane,
[bis(N-2,4,6-triisopropylphenyl-2-aminoethyl)(2-picolyl)amine]manganese dichloride/modified methylalumoxane,
[bis(N-2,6-diisopropyl-4-methylphenyl-2-aminoethyl)(2-picolyl)amine]manganese dichloride/modified methylalumoxane,
[bis(N-2,6-diethylphenyl-2-aminoethyl)(2-picolyl)amine]manganese dichloride/modified methylalumoxane,
[bis(N-2,6-dimethylphenyl-2-aminoethyl)amine]nickel dichloride/modified methylalumoxane,
[bis(N-2,4,6-trimethylphenyl-2-aminoethyl)amine]nickel dichloride/modified methylalumoxane,
[bis(N-2,6-diisopropylphenyl-2-aminoethyl)amine]nickel dichloride/modified methylalumoxane,
[bis(N-2,4,6-triisopropylphenyl-2-aminoethyl)amine] nickel dichloride/modified methylalumoxane,
[bis(N-2,6-diisopropyl-4-methylphenyl-2-aminoethyl)amine]nickel dichloride/modified methylalumoxane,
[bis(N-2,6-diethylphenyl-2-aminoethyl)amine]nickel dichloride/modified methylalumoxane,
[bis(N-2,6-dimethylphenyl-2-aminoethyl)methylamine]nickel dichloride/modified methylalumoxane,
[bis(N-2,4,6-trimethylphenyl-2-aminoethyl)methylamine]nickel dichloride/modified methylalumoxane,
[bis(N-2,6-diisopropylphenyl-2-aminoethyl)methylamine]nickel dichloride/modified methylalumoxane,
[bis(N-2,4,6-triisopropylphenyl-2-aminoethyl)methylamine]nickel dichloride/modified methylalumoxane,

[bis(N-2,6-diisopropyl-4-methylphenyl-2-aminoethyl) methylamine]nickel dichloride/modified methylalumoxane,
[bis(N-2,6-diethylphenyl-2-aminoethyl)methylamine] nickel dichloride/modified methylalumoxane,
[bis(N-2,6-dimethylphenyl-2-aminoethyl)(2-picolyl) amine]nickel dichloride/modified methylalumoxane,
[bis(N-2,4,6-trimethylphenyl-2-aminoethyl)(2-picolyl) amine]nickel dichloride/modified methylalumoxane,
[bis(N-2,6-diisopropylphenyl-2-aminoethyl)(2-picolyl) amine]nickel dichloride/modified methylalumoxane,
[bis(N-2,4,6-triisopropylphenyl-2-aminoethyl)(2-picolyl) amine]nickel dichloride/modified methylalumoxane,
[bis(N-2,6-diisopropyl-4-methylphenyl-2-aminoethyl)(2-picolyl)amine]nickel dichloride/modified methylalumoxane,
[bis(N-2,6-diethylphenyl-2-aminoethyl)(2-picolyl) amine]nickel dichloride/modified methylalumoxane,
[bis(N-2,6-dimethylphenyl-2-aminoethyl)amine]copper dichloride/modified methylalumoxane,
[bis(N-2,4,6-trimethylphenyl-2-aminoethyl)amine]copper dichloride/modified methylalumoxane,
[bis(N-2,6-diisopropylphenyl-2-aminoethyl)amine]copper dichloride/modified methylalumoxane,
[bis(N-2,6-dimethylphenyl-2-aminoethyl)methylamine] copper dichloride/modified methylalumoxane,
[bis(N-2,4,6-trimethylphenyl-2-aminoethyl)methylamine]copper dichloride/modified methylalumoxane,
[bis(N-2,6-diisopropylphenyl-2-aminoethyl)methylamine]copper dichloride/modified methylalumoxane,
[bis(N-2,6-dimethylphenyl-2-aminoethyl)(2-picolyl) amine]copper dichloride/modified methylalumoxane,
[bis(N-2,4,6-trimethylphenyl-2-aminoethyl)(2-picolyl) amine]copper dichloride/modified methylalumoxane, and
[bis(N-2,6-diisopropylphenyl-2-aminoethyl)(2-picolyl) amine]copper dichloride/modified methylalumoxane.

40. A transition metal catalyst compound for oligomerization of an unsaturated monomer is represented by the formula:

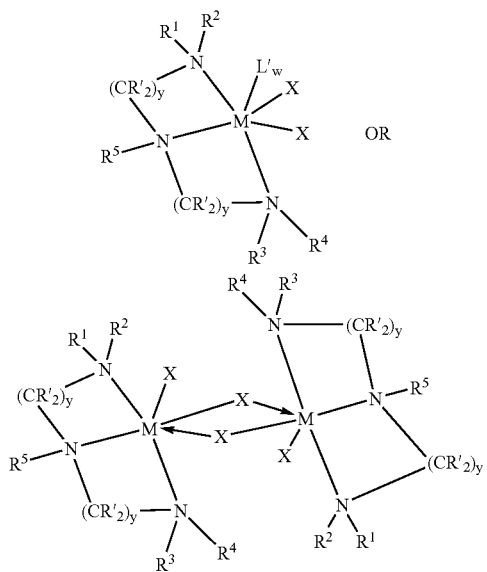

wherein
each M is, independently, a group 7, 8, 9, or 10 transition metal;
N is nitrogen;
C is carbon;
each X is, independently, an anionic monodentate ligand, or both X groups together may form a bidentate dianionic ligand;
each R' is, independently, a hydrogen, a hydrocarbyl, a substituted hydrocarbyl, a halocarbyl, or a substituted halocarbyl; independently, two R' groups on the same carbon may join to form a cyclic or polycyclic ring structure; when y is 2, 3, or 4, two or more R' groups on adjacent carbon atoms may join to form a cyclic or polycyclic ring structure;
each y is, independently, 1, 2, 3 or 4;
each R1 and R3 is, independently, a hydrogen, hydrocarbyl or halocarbyl;
each R2 and R4 is, independently, a C3 to C50 hydrocarbyl or a C3 to C50 halocarbyl;
each R5 is, independently, hydrogen, a hydrocarbyl, a substituted hydrocarbyl, a halocarbyl, or a substituted halocarbyl; optionally R5 may be bonded to M through the heteroatom of a substituted hydrocarbyl, or a substituted halocarbyl;
L' is a neutral ligand bonded to M;
and w is 0 or 1.

41. The compound of claim 40 wherein M comprises a group 9, or 10 transition metal.

42. The compound of claim 40 wherein M comprises one or more of nickel, cobalt, iron or manganese.

43. The compound of claim 40 wherein X is a hydride, hydrocarbyl, substituted hydrocarbyl, halocarbyl, substituted halocarbyl, or two X groups together are a hydrocarbdiyl, halocarbdiyl, substituted hydrocarbdiyl, or substituted halocarbdiyl.

44. The compound of claim 40 wherein X is selected from the group consisting of chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, methoxy, ethoxy, propoxy, butoxy, dimethylamido, diethylamido, methylethylamido, phenoxy, benzoxy, and allyl.

45. The compound of claim 40 wherein two X groups are joined and are selected from the group consisting of methylidene, ethylidene, propylidene, tetramethylene, pentamethylene, hexamethylene, butadiene, methylbutadiene, dimethylbutadiene, pentadiene, methylpentadiene, dimethylpentadiene, hexadiene, methylhexadiene, and dimethylhexadiene.

46. The compound of claim 40 wherein R1 and/or R3, independently, are selected from the group consisting of hydrogen, C1 to C30 hydrocarbyls, and C1 to C30 halocarbyls, and wherein R2 and/or R4, independently, are selected from the group consisting of C3 to C50 hydrocarbyls, and C3 to C50 halocarbyls.

47. The compound of claim 40 wherein R5 is selected from the group consisting of hydrogen, C1 to C30 hydrocarbyls, C1 to C30 substituted hydrocarbyls, C1 to C30 halocarbyls and C1 to C30 substituted halocarbyls.

48. The compound of claim 40 wherein R' is selected from the group consisting of hydrogen, C1 to C30 hydrocarbyls, C1 to C30 substituted hydrocarbyls, C1 to C30 halocarbyls, and C1 to C30 substituted halocarbyls.

49. A catalyst system comprising the compound of claim 40 and an activator.

50. The catalyst system of claim 49 wherein the activator comprises an alumoxane.

51. The catalyst system of claim 50 wherein the activator comprises an alkyl aluminum compound.

52. The catalyst system of claim 50 wherein the activator comprises an ionizing or stoichiometric activator.

53. The catalyst system of claim 50 wherein the activator comprises one or more of:

trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, di(isopropyl)ammonium tetraphenylborate, dicyclohexylammonium tetraphenylborate; tri(o-tolyl)phosphonium tetraphenylborate, tri(2,6-dimethylphenyl)phosphonium tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, di(isopropyl)ammonium tetrakis(pentafluorophenyl)borate, dicyclohexylammonium tetrakis(pentafluorophenyl)borate; tri(o-tolyl)phosphonium tetrakis(pentafluorophenyl)borate, tri(2,6-dimethylphenyl)phosphonium tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, di(isopropyl)ammonium tetrakis(2,3,4,6-tetrafluorophenyl)borate, dicyclohexylammonium tetrakis(2,3,4,6-tetrafluorophenyl)borate; tri(o-tolyl)phosphonium tetrakis(2,3,4,6-tetrafluorophenyl)borate, tri(2,6-dimethylphenyl)phosphonium tetrakis(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, di(isopropyl)ammonium tetrakis(pentafluoronaphthyl)borate, dicyclohexylammonium tetrakis(pentafluoronaphthyl)borate; tri(o-tolyl)phosphonium tetrakis(pentafluoronaphthyl)borate, tri(2,6-dimethylphenyl)phosphonium tetrakis(pentafluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, di(isopropyl)ammonium tetrakis(pentafluorobiphenyl)borate, dicyclohexylammonium tetrakis(pentafluorobiphenyl)borate; tri(o-tolyl)phosphonium tetrakis(pentafluorobiphenyl)borate, tri(2,6-dimethylphenyl)phosphonium tetrakis(pentafluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, di(isopropyl)ammonium tetrakis(3,5-bis(trifluoromethyl)phenyl)borate, dicyclohexylammonium tetrakis(3,5-bis(trifluoromethyl)phenyl)borate; tri(o-tolyl)phosphonium tetrakis(3,5-bis(trifluoromethyl)phenyl)borate, and tri(2,6-dimethylphenyl)phosphonium tetrakis(3,5-bis(trifluoromethyl)phenyl)borate.

54. The catalyst system of claim 49 wherein the transition metal catalyst compound is present on a support.

55. The catalyst system of claim 49 wherein the transition metal catalyst compound and the activator are present on a support.

56. The catalyst system of claim 49 wherein the support comprises one or more Group 2, 3, 4, 5, 13 or 14 metal oxides.

57. The catalyst system of claim 49 wherein the support comprises one or more of silica, alumina, silica-alumina, magnesia, titania, zirconia, magnesium chloride, montmorillonite, phyllosilicate, zeolites, talc, clays, silica-chromium, silica-titania, porous acrylic polymers, nanocomposites, aerogels, spherulites, or polymeric beads.

58. The catalyst system of claim 49 wherein the support is silica.

59. The catalyst system of claim 49 wherein the activator is bound to the support prior to combination with the transition metal catalyst compound.

60. The catalyst system of claim 49 wherein M comprises one or more of nickel, cobalt, iron or manganese and X is selected from the group consisting of chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, methoxy, ethoxy, propoxy, butoxy, dimethylamido, diethylamido, methylethylamido, phenoxy, benzoxy, and allyl and $R^1$ or $R^3$, independently, are selected from the group consisting of hydrogen, $C_1$ to $C_{30}$ hydrocarbyls, and $C_1$ to $C_{30}$ halocarbyls, and wherein $R^2$ or $R^4$, independently, are selected from the group consisting of $C_3$ to $C_{50}$ hydrocarbyls, and $C_3$ to $C_{50}$ halocarbyls and $R^5$ is selected from the group consisting of hydrogen, $C_1$ to $C_{30}$ hydrocarbyls, $C_1$ to $C_{30}$ substituted hydrocarbyls, $C_1$ to $C_{30}$ halocarbyls and $C_1$ to $C_{30}$ substituted halocarbyls and R' is selected from the group consisting of hydrogen, $C_1$ to $C_{30}$ hydrocarbyls, $C_1$ to $C_{30}$ substituted hydrocarbyls, $C_1$ to $C_{30}$ halocarbyls, and $C_1$ to $C_{30}$ substituted halocarbyls.

61. The catalyst system of claim 60 wherein the activator comprises an alumoxane.

62. The catalyst system of claim 60 wherein the activator comprises one or more of:
trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, di(isopropyl)ammonium tetraphenylborate, dicyclohexylammonium tetraphenylborate; tri(o-tolyl)phosphonium tetraphenylborate, tri(2,6-dimethylphenyl)phosphonium tetraphenylborate, trimethylammonium tetrakis(pentafluorophenyl) borate, triethylammonium tetrakis(pentafluorophenyl) borate, tripropylammonium tetrakis (pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis (pentafluorophenyl)borate, tropillium tetrakis (pentafluorophenyl)borate, triphenylcarbenium tetrakis (pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, di(isopropyl)ammonium tetrakis(pentafluorophenyl)borate, dicyclohexylammonium tetrakis(pentafluorophenyl) borate; tri(o-tolyl)phosphonium tetrakis(pentafluorophenyl)borate, tri(2,6-dimethylphenyl)phosphonium tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl) borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, di(isopropyl)ammonium tetrakis(2,3,4,6-tetrafluorophenyl)borate, dicyclohexylammonium tetrakis(2,3,4,6-tetrafluorophenyl)borate; tri(o-tolyl)phosphonium tetrakis(2,3,4,6-tetrafluorophenyl)borate, tri(2,6-dimethylphenyl)phosphonium tetrakis(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl) borate, N,N dimethyl-(2,4,6-trimethylanilinium)tetrakis(perfluoronaphthyl)borate, tropillium tetrakis (perfluoronaphthyl)borate, triphenylcarbenium tetrakis (perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, di(isopropyl)ammonium tetrakis(pentafluoronaphthyl)borate, dicyclohexylammonium tetrakis(pentafluoronaphthyl) borate; tri(o-tolyl)phosphonium tetrakis(pentafluoronaphthyl)borate, tri(2,6-dimethylphenyl)phosphonium tetrakis(pentafluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl) borate, N,N-dimethylanilinium tetrakis(perfluorobiphenyl)borate, N,N-diethylanilinium tetrakis (perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, di(isopropyl)ammonium tetrakis(pentafluorobiphenyl) borate, dicyclohexylammonium tetrakis(pentafluorobiphenyl)borate; tri(o-tolyl)phosphonium tetrakis(pentafluorobiphenyl)borate, tri(2,6-dimethylphenyl) phosphonium tetrakis(pentafluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl) phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl) phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, di(isopropyl) ammonium tetrakis(3,5-bis(trifluoromethyl)phenyl) borate, dicyclohexylammonium tetrakis(3,5-bis (trifluoromethyl)phenyl)borate; tri(o-tolyl) phosphonium tetrakis(3,5-bis(trifluoromethyl)phenyl) borate, and tri(2,6-dimethylphenyl)phosphonium tetrakis(3,5-bis(trifluoromethyl)phenyl)borate.

63. The catalyst system of claim 61 wherein the compound and/or the activator are present on a support and the support comprises one or more of silica, alumina, silica-alumina, magnesia, titania, zirconia, magnesium chloride, montmorillonite, phyllosilicate, zeolites, talc, clays, silica-chromium, silica-titania, porous acrylic polymers, nanocomposites, aerogels, spherulites, or polymeric beads.

64. The catalyst system of claim 62 wherein the compound and/or the activator are present on a support and the support comprises one or more of silica, alumina, silica-alumina, magnesia, titania, zirconia, magnesium chloride, montmorillonite, phyllosilicate, zeolites, talc, clays, silica-chromium, silica-titania, porous acrylic polymers, nanocomposites, aerogels, spherulites, or polymeric beads.

65. The catalyst system of claim 62 wherein the activator is bound to the support prior to combination with the transition metal catalyst compound.

66. The catalyst system of claim 64 where the activator is bound to the support prior to combination with the transition metal catalyst compound.

67. A process to oligomerize an unsaturated monomer comprising contacting the monomer with the catalyst system of claim 49.

68. A process to oligomerize an unsaturated monomer comprising contacting the monomer with the catalyst system of claim 60.

69. A process to oligomerize an unsaturated monomer comprising contacting the monomer with the catalyst system of claim 61.

70. A process to oligomerize an unsaturated monomer comprising contacting the monomer with the catalyst system of claim 62.

71. A process to oligomerize an unsaturated monomer comprising contacting the monomer with the catalyst system of claim 63.

72. A process to oligomerize an unsaturated monomer comprising contacting the monomer with the catalyst system of claim 64.

73. A process to oligomerize an unsaturated monomer comprising contacting the monomer with the catalyst system of claim 65.

74. The process of claim 67 wherein the monomer comprises one or more alpha-olefins.

75. The process of claim 67 wherein the monomer comprises one or more C2 to C12 alpha-olefins.

76. A transition metal catalyst compound for oligomerization of an unsaturated monomer represented by the formula:

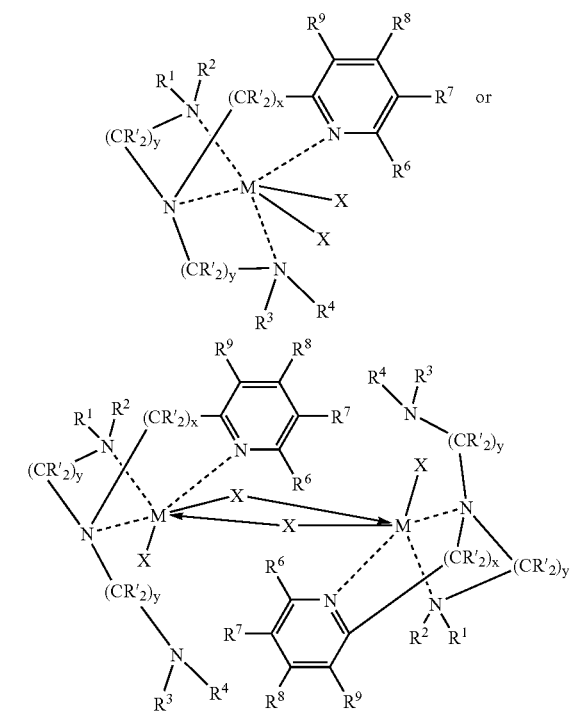

wherein
each M is, independently, a Group 7, 8, 9, or 10 transition metal;
N is nitrogen;
C is carbon;
each X is, independently, an anionic monodentate ligand, or both X groups together may form a bidentate dianionic ligand;
each R' is, independently, a hydrogen, a hydrocarbyl, a substituted hydrocarbyl, a halocarbyl, or a substituted halocarbyl; independently, two R' groups on the same carbon may join to form a cyclic or polycyclic ring structure; when x is 2, 3, or 4, and or when y is 2, 3, or 4, two or more R' groups on adjacent carbon atoms may join to form a cyclic or polycyclic ring structure;
each x is, independently, 1, 2, 3 or 4;
each y is, independently, 1, 2, 3 or 4;
each $R^1$ and $R^3$ is, independently, a hydrogen, hydrocarbyl or halocarbyl;
each $R^2$ and $R^4$ is, independently, a $C_3$ to $C_{50}$ hydrocarbyl or a $C_3$ to $C_{50}$ halocarbyl; and
each $R^6$, $R^7$, $R^8$, or $R^9$ is, independently, a hydrogen, a hydrocarbyl, a substituted a hydrocarbyl, a halocarbyl, or a substituted halocarbyl, or independently, two adjacent $R^6$, $R^7$, $R^8$, or $R^9$ may join together to form a cyclic or polycyclic ring structure.

77. The compound of claim 76 wherein M comprises a group Group 9, or 10 transition metal.

78. The compound of claim 76 wherein M comprises one or more of nickel, cobalt, iron or manganese.

79. The compound of claim 76 wherein X is a hydride, hydrocarbyl, substituted hydrocarbyl, halocarbyl, substituted halocarbyl, or two X groups together are a hydrocarbdiyl, halocarbdiyl, substituted hydrocarbdiyl, or substituted halocarbdiyl.

80. The compound of claim 76 wherein is selected from the group consisting of chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, methoxy, ethoxy, propoxy, butoxy, dimethylamido, diethylamido, methylethylamido, phenoxy, benzoxy, and allyl.

81. The compound of claim 76 wherein two X groups are joined and are selected from the group consisting of methylidene, ethylidene, propylidene, tetramethylene, pentamethylene, hexamethylene, butadiene, methylbutadiene, dimethylbutadiene, pentadiene, methylpentadiene, dimethylpentadiene, hexadiene, methylhexadiene, and dimethylhexadiene.

82. The compound of claim 76 wherein $R^6$ is selected from the group consisting of hydrogen, $C_1$ to $C_{30}$ hydrocarbyls, $C_1$ to $C_{30}$ substituted hydrocarbyls, $C_1$ to $C_{30}$ halocarbyls and $C_1$ to $C_{30}$ substituted halocarbyls.

83. The compound of claim 76 wherein $R^1$ or $R^3$, independently, are selected from the group consisting of hydrogen, $C_1$ to $C_{30}$ hydrocarbyls, and $C_1$ to $C_{30}$ halocarbyls, and wherein $R^2$ or $R^4$, independently, are selected from the group consisting of $C_3$ to $C_{50}$ hydrocarbyls, and $C_3$ to $C_{50}$ halocarbyls.

84. The compound of claim 76 wherein $R^7$, $R^8$ and $R^9$, if present, are, independently, selected from the group consisting of hydrogen, $C_1$ to $C_{30}$ hydrocarbyls, $C_1$ to $C_{30}$ substituted hydrocarbyls, $C_1$ to $C_{30}$ halocarbyls, and $C_1$ to $C_{30}$ substituted halocarbyls.

85. The compound of claim 76 wherein R', if present, is selected from the group consisting of hydrogen, $C_1$ to $C_{30}$ hydrocarbyls, $C_1$ to $C_{30}$ substituted hydrocarbyls, $C_1$ to $C_{30}$ halocarbyls, and $C_1$ to $C_{30}$ substituted halocarbyls.

86. A catalyst system comprising the compound of claim 76 and an activator.

87. The catalyst system of claim 86 wherein the activator comprises an alumoxane.

88. The catalyst system of claim 86 wherein the activator comprises an alkyl aluminum compound.

89. The catalyst system of claim 86 wherein the activator comprises an ionizing or stoichiometric activator.

90. The catalyst system of claim 86 wherein the activator comprises of or more of: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, di(isopropyl)ammonium tetraphenylborate, dicyclohexylammonium tetraphenylborate; tri(o-tolyl)phosphonium tetraphenylborate, tri(2,6-dimethylphenyl)phosphonium tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis (pentafluorophenyl)borate, tropillium tetrakis (pentafluorophenyl)borate, triphenylcarbenium tetrakis (pentafluorophenyl)borate, triphenylphosphonium tetrakis (pentafluorophenyl)borate, triethylsilylium tetrakis (pentafluorophenyl)borate, benzene(diazonium)tetrakis (pentafluorophenyl)borate, di(isopropyl)ammonium tetrakis (pentafluorophenyl)borate, dicyclohexylammonium tetrakis (pentafluorophenyl)borate; tri(o-tolyl)phosphonium tetrakis (pentafluorophenyl)borate, tri(2,6-dimethylphenyl) phosphonium tetrakis(pentafluorophenyl)borate, trimethylammonium tetrakis-(2,3,4,6-tetrafluorophenyl)borate, triethylammonium tetrakis-(2,3,4,6-tetrafluorophenyl) borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, di(isopropyl)ammonium tetrakis(2,3,4,6-tetrafluorophenyl)borate, dicyclohexylammonium tetrakis(2,3,4,6-tetrafluorophenyl)borate; tri(o-tolyl)phosphonium tetrakis(2,3,4,6-tetrafluorophenyl)borate, tri(2,6-dimethylphenyl)phosphonium tetrakis(2,3,4,6-tetrafluorophenyl)borate, trimethylammonium tetrakis (perfluoronaphthyl)borate, triethylammonium tetrakis (perfluoronaphthyl)borate, tripropylammonium tetrakis (perfluoronaphthyl)borate, tri(n-butyl)ammonium tetrakis (perfluoronaphthyl)borate, tri(t-butyl)ammonium tetrakis (perfluoronaphthyl)borate, N,N-dimethylanilinium tetrakis (perfluoronaphthyl)borate, N,N-diethylanilinium tetrakis (perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, di(isopropyl)ammonium tetrakis(pentafluoronaphthyl)borate, dicyclohexylammonium tetrakis(pentafluoronaphthyl)borate; tri(o-tolyl)phosphonium tetrakis(pentafluoronaphthyl)borate, tri(2,6-dimethylphenyl)phosphonium tetrakis(pentafluoronaphthyl) borate, trimethylammonium tetrakis(perfluorobiphenyl) borate, triethylammonium tetrakis(perfluorobiphenyl) borate, tripropylammonium tetrakis(perfluorobiphenyl) borate, tri(n-butyl)ammonium tetrakis(perfluorobiphenyl) borate, tri(t-butyl)ammonium tetrakis(perfluorobiphenyl) borate, N,N-dimethylanilinium tetrakis(perfluorobiphenyl) borate, N,N-diethylanilinium tetrakis(perfluorobiphenyl) borate, N,N-dimethyl-(2,4,6-trimethylanilinium)tetrakis (perfluorobiphenyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium)tetrakis (perfluorobiphenyl)borate, di(isopropyl)ammonium tetrakis (pentafluorobiphenyl)borate, dicyclohexylammonium tetrakis(pentafluorobiphenyl)borate; tri(o-tolyl)phosphonium tetrakis(pentafluorobiphenyl)borate, tri(2,6-dimethylphenyl)phosphonium tetrakis(pentafluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, di(isopropyl)ammonium tetrakis(3,5-bis(trifluoromethyl)phenyl)borate, dicyclohexylammonium tetrakis(3,5-bis(trifluoromethyl)phenyl)borate; tri(o-tolyl)phosphonium tetrakis(3,5-bis(trifluoromethyl)phenyl)borate, and tri(2,6-dimethylphenyl)phosphonium tetrakis(3,5-bis(trifluoromethyl)phenyl)borate.

91. The catalyst system of claim 86 wherein the transition metal catalyst compound is present on a support.

92. The catalyst system of claim 86 wherein the transition metal catalyst compound and the activator are present on a support.

93. The catalyst system of claim 86 wherein the support comprises one or more Group 2, 3, 4, 5, 13 or 14 metal oxides.

94. The catalyst system of claim 86 wherein the support comprises one or more of silica, alumina, silica-alumina, magnesia, titania, zirconia, magnesium chloride, montmorillonite, phyllosilicate, zeolites, talc, clays, silica-chromium, silica-titania, porous acrylic polymers, nanocomposites, aerogels, spherulites, or polymeric beads.

95. The catalyst system of claim 86 wherein the support is silica.

96. The catalyst system of claim 86 wherein the activator is bound to the support prior to combination with the transition metal catalyst compound.

97. The catalyst system of claim 76 wherein M comprises one or more of nickel, cobalt, iron or manganese, and X is selected from the group consisting of chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, methoxy, ethoxy, propoxy, butoxy, dimethylamido, diethylamido, methylethylamido, phenoxy, benzoxy, and allyl and $R^6$ is selected from the group consisting of hydrogen, $C_1$ to $C_{30}$ hydrocarbyls, $C_1$ to $C_{30}$ substituted hydrocarbyls, $C_1$ to $C_{30}$ halocarbyls and $C_1$ to $C_{30}$ substituted halocarbyls and $R^1$ and $R^3$, independently, are selected from the group consisting of hydrogen, $C_1$ to $C_{30}$ hydrocarbyls, and $C_1$ to $C_{30}$ halocarbyls, and wherein $R^2$ and $R^4$, independently, are selected from the group consisting of $C_3$ to $C_{50}$ hydrocarbyls, and $C_3$ to $C_{50}$ halocarbyls and $R^7$, $R^8$ and $R^9$, if present, are, independently, selected from the group consisting of hydrogen, $C_1$ to $C_{30}$ hydrocarbyls, $C_1$ to $C_{30}$ substituted hydrocarbyls, $C_1$ to $C_{30}$ halocarbyls, and $C_1$ to $C_{30}$ substituted halocarbyls and R' is selected from the group consisting of hydrogen, $C_1$ to $C_{30}$ hydrocarbyls, $C_1$ to $C_{30}$ substituted hydrocarbyls, $C_1$ to $C_{30}$ halocarbyls, and $C_1$ to $C_{30}$ substituted halocarbyls.

98. The catalyst system of claim 97 wherein the activator comprises an alumoxane.

99. The catalyst system of claim 97 wherein the activator comprises on or more of:
trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, di(isopropyl)ammonium tetraphenylborate, dicyclohexylammonium tetraphenylborate; tri(o-tolyl)phosphonium tetraphenylborate, tri(2,6-dimethylphenyl)phosphonium tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, di(isopropyl)ammonium tetrakis(pentafluorophenyl)borate, dicyclohexylammonium tetrakis(pentafluorophenyl)borate; tri(o-tolyl)phosphonium tetrakis(pentafluorophenyl)borate, tri(2,6-dimethylphenyl)phosphonium tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, di(isopropyl)ammonium tetrakis(2,3,4,6-tetrafluorophenyl)borate, dicyclohexylammonium tetrakis(2,3,4,6-tetrafluorophenyl)borate; tri(o-tolyl)phosphonium tetrakis(2,3,4,6-tetrafluorophenyl)borate, tri(2,6-dimethylphenyl)phosphonium tetrakis(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)

borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, di(isopropyl)ammonium tetrakis(pentafluoronaphthyl)borate, dicyclohexylammonium tetrakis(pentafluoronaphthyl) borate; tri(o-tolyl)phosphonium tetrakis(pentafluoronaphthyl)borate, tri(2,6-dimethylphenyl)phosphonium tetrakis(pentafluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl) borate, N,N-dimethylanilinium tetrakis(perfluorobiphenyl)borate, N,N-diethylanilinium tetrakis (perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, di(isopropyl)ammonium tetrakis(pentafluorobiphenyl) borate, dicyclohexylammonium tetrakis(pentafluorobiphenyl)borate; tri(o-tolyl)phosphonium tetrakis(pentafluorobiphenyl)borate, tri(2,6-dimethylphenyl) phosphonium tetrakis(pentafluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, di(isopropyl)ammonium tetrakis(3,5-bis(trifluoromethyl)phenyl) borate, dicyclohexylammonium tetrakis(3,5-bis(trifluoromethyl)phenyl)borate; tri(o-tolyl)phosphonium tetrakis(3,5-bis(trifluoromethyl)phenyl) borate, and tri(2,6-dimethylphenyl)phosphonium tetrakis(3,5-bis(trifluoromethyl)phenyl)borate.

100. The catalyst system of claim 98 wherein the compound and/or activator are present on a support and the support comprises one or more of silica, alumina, silica-alumina, magnesia, titania, zirconia, magnesium chloride, montmorillonite, phyllosilicate, zeolites, talc, clays, silica-chromium, silica-titania, porous acrylic polymers, nanocomposites, aerogels, spherulites, or polymeric beads.

101. The catalyst system of claim 99 wherein the compound and/or activator are present on a support and the support comprises one or more of silica, alumina, silica-alumina, magnesia, titania, zirconia, magnesium chloride, montmorillonite, phyllosilicate, zeolites, talc, clays, silica-chromium, silica-titania, porous acrylic polymers, nanocomposites, aerogels, spherulites, or polymeric beads.

102. The catalyst system of claim 101 wherein the activator is bound to the support prior to combination with the transition metal catalyst compound.

103. A process to oligomerize an unsaturated monomer comprising contacting the monomer with the catylyst system of claim 86.

104. A process to oligomerize an unsaturated monomer comprising contacting the monomer with the catylyst system of claim 97.

105. A process to oligomerize an unsaturated monomer comprising contacting the monomer with the catylyst system of claim 98.

106. A process to oligomerize an unsaturated monomer comprising contacting the monomer with the catylyst system of claim 99.

107. A process to oligomerize an unsaturated monomer comprising contacting the monomer with the catylyst system of claim 100.

108. A process to oligomerize an unsaturated monomer comprising contacting the monomer with the catylyst system of claim 101.

109. A process to oligomerize an unsaturated monomer comprising contacting the monomer with the catylyst system of claim 102.

110. The process of claim 103 wherein the monomer comprises one or more alpha-olefins.

111. The process of claim 103 wherein the monomer comprises one or more of C2 to C12 alpha-olefins.

112. A transition metal catalyst compound for ologomerization of an unsaturated monomer represented by the formula:

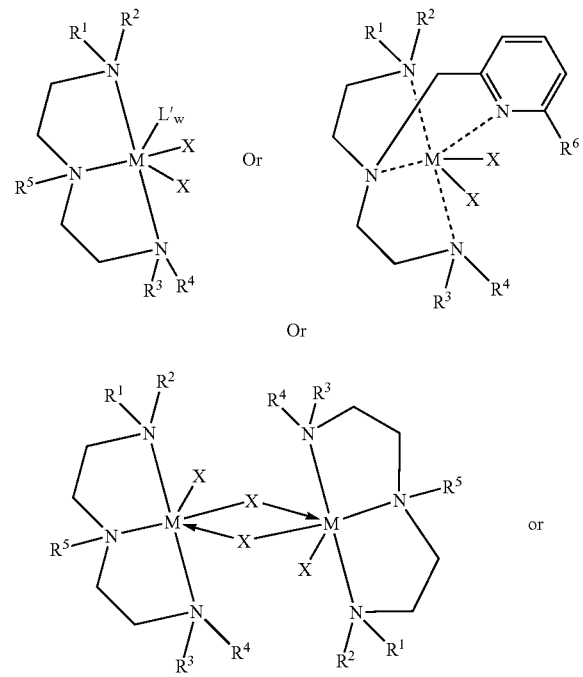

-continued

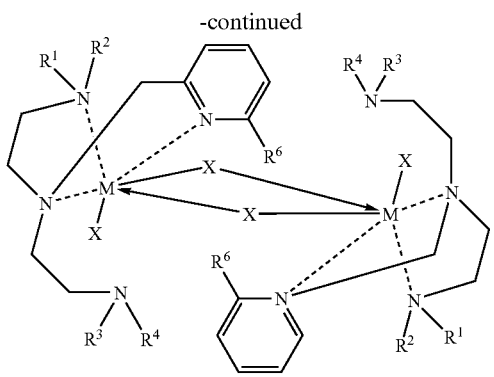

wherein
each M is, independently, a Group 7, 8, 9, or 10, transition metal;
N is nitrogen;
each X is, independently, an anionic monodentate ligand, or both X groups together may form a bidentate dianionic ligand;
$R^1$ and $R^3$ is, independently, a hydrogen, hydrocarbyl or halocarbyl;
$R^2$ and $R^4$ is, independently, a $C_3$ to $C_{50}$ hydrocarbyl or a $C_3$ to $C_{50}$ halocarbyl;
$R^5$ is, independently, hydrogen, a hydrocarbyl, a substituted hydrocarbyl, a halocarbyl, or a substituted halocarbyl; optionally $R^5$ may be bonded to M through the heteroatom of a substituted hydrocarbyl, or a substituted halocarbyl;
L' is a neutral ligand bonded to M;
and w is 0 or 1;
$R^6$ is a hydrogen, a hydrocarbyl, a substituted a hydrocarbyl, a halocarbyl, or a substituted halocarbyl.

113. The compound of claim 112 wherein M comprises a group 9, or 10 transition metal.

114. The compound of claim 112 wherein M comprises one or more of nickel, cobalt, iron or manganese.

115. The compound of claim 112 wherein X is a hydride, hydrocarbyl, substituted hydrocarbyl, halocarbyl, substituted halocarbyl, or two X groups together are a hydrocarbdiyl, halocarbdiyl, substituted hydrocarbdiyl, or substituted halocarbdiyl.

116. The compound of claim 112 wherein X is selected from the group consisting of chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, methoxy, ethoxy, propoxy, butoxy, dimethylamido, diethylamido, methylethylamido, phenoxy, benzoxy, and allyl.

117. The compound of claim 112 wherein two X groups are joined and are selected from the group consisting of methylidene, ethylidene, propylidene, tetramethylene, pentamethylene, hexamethylene, butadiene, methylbutadiene, dimethylbutadiene, pentadiene, methylpentadiene, dimethylpentadiene, hexadiene, methylhexadiene, and dimethylhexadiene.

118. The compound of claim 112 wherein $R^6$ is selected from the group consisting of hydrogen, $C_1$ to $C_{30}$ hydrocarbyls, $C_1$ to $C_{30}$ substituted hydrocarbyls, $C_1$ to $C_{30}$ halocarbyls and $C_1$ to $C_{30}$ substituted halocarbyls.

119. The compound of claim 112 wherein $R^1$ and $R^3$, independently, are selected from the group consisting of hydrogen, $C_1$ to $C_{30}$ hydrocarbyls, and $C_1$ to $C_{30}$ halocarbyls, and wherein $R^2$ and $R^4$, independently, are selected from the group consisting of $C_3$ to $C_{50}$ hydrocarbyls, and $C_3$ to $C_{50}$ halocarbyls.

120. A catalyst system comprising the compound of claim 112 and an activator.

121. The catalyst system of claim 120 wherein the activator comprises an alumoxane.

122. The catalyst system of claim 120 wherein the activator comprises an alkyl aluminum compound.

123. The catalyst system of claim 120 wherein the activator comprises an ionizing or stoichiometric activator.

124. The catalyst system of claim 120 wherein the activator comprises of or more of:
trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, di(isopropyl)ammonium tetraphenylborate, dicyclohexylammonium tetraphenylborate; tri(o-tolyl)phosphonium tetraphenylborate, tri(2,6-dimethylphenyl)phosphonium tetraphenylborate, trimethylammonium tetrakis(pentafluorophenyl) borate, triethylammonium tetrakis(pentafluorophenyl) borate, tripropylammonium tetrakis (pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis (pentafluorophenyl)borate, tropillium tetrakis (pentafluorophenyl)borate, triphenylcarbenium tetrakis (pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, di(isopropyl)ammonium tetrakis(pentafluorophenyl)borate, dicyclohexylammonium tetrakis(pentafluorophenyl) borate; tri(o-tolyl)phosphonium tetrakis(pentafluorophenyl)borate, tri(2,6-dimethylphenyl)phosphonium tetrakis(pentafluorophenyl)borate, trimethylammonium tetrakis-(2,3,4,6-tetrafluorophenyl)borate, triethylammonium tetrakis-(2,3,4,6-tetrafluorophenyl) borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl) borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, di(isopropyl)ammonium tetrakis(2,3,4,6-tetrafluorophenyl)borate, dicyclohexylammonium tetrakis(2,3,4,6-tetrafluorophenyl)borate; tri(o-tolyl)phosphonium tetrakis(2,3,4,6-tetrafluorophenyl)borate, tri(2,6-dimethylphenyl)phosphonium tetrakis(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, di(isopropyl)ammonium tetrakis(pentafluoronaphthyl)borate, dicyclohexylammonium tetrakis(pentafluoronaphthyl)borate; tri(o-tolyl)phosphonium tetrakis(pentafluoronaphthyl)borate, tri(2,6-dimethylphenyl)phosphonium tetrakis(pentafluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, di(isopropyl)ammonium tetrakis(pentafluorobiphenyl)borate, dicyclohexylammonium tetrakis(pentafluorobiphenyl)borate; tri(o-tolyl)phosphonium tetrakis(pentafluorobiphenyl)borate, tri(2,6-dimethylphenyl)phosphonium tetrakis(pentafluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, di(isopropyl)ammonium tetrakis(3,5-bis(trifluoromethyl)phenyl)borate, dicyclohexylammonium tetrakis(3,5-bis(trifluoromethyl)phenyl)borate; tri(o-tolyl)phosphonium tetrakis(3,5-bis(trifluoromethyl)phenyl)borate, and tri(2,6-dimethylphenyl)phosphonium tetrakis(3,5-bis(trifluoromethyl)phenyl)borate.

125. The catalyst system of claim 120 wherein the transition metal catalyst compound is present on a support.

126. The catalyst system of claim 120 wherein the transition metal catalyst compound and the activator are present on a support.

127. The catalyst system of claim 120 wherein the support comprises one or more Group 2, 3, 4, 5, 13 or 14 metal oxides.

128. The catalyst system of claim 120 wherein the support comprises one or more of silica, alumina, silica-alumina, magnesia, titania, zirconia, magnesium chloride, montmorillonite, phyllosilicate, zeolites, talc, clays, silica-chromium, silica-titania, porous acrylic polymers, nanocomposites, aerogels, spherulites, or polymeric beads.

129. The catalyst system of claim 120 wherein the support is silica.

130. The catalyst system of claim 120 wherein the activator is bound to the support prior to combination with the transition metal catalyst compound.

131. The catalyst system of claim 120 wherein M comprises one or more of nickel, cobalt, iron or manganese, and X is selected from the group consisting of chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, methoxy, ethoxy, propoxy, butoxy, dimethylamido, diethylamido, methylethylamido, phenoxy, benzoxy, and allyl and $R^6$ is selected from the group consisting of hydrogen, $C_1$ to $C_{30}$ hydrocarbyls, $C_1$ to $C_{30}$ substituted hydrocarbyls, $C_1$ to $C_{30}$ halocarbyls and $C_1$ to $C_{30}$ substituted halocarbyls and $R^1$ and $R^3$, independently, are selected from the group consisting of hydrogen, $C_1$ to $C_{30}$ hydrocarbyls, and $C_1$ to $C_{30}$ halocarbyls, and wherein $R^2$ and $R^4$, independently, are selected from the group consisting of $C_3$ to $C_{50}$ hydrocarbyls, and $C_3$ to $C_{50}$ halocarbyls, and $R^5$ is selected from the group consisting of hydrogen, $C_1$ to $C_{30}$ hydrocarbyls, $C_1$ to $C_{30}$ substituted hydrocarbyls, $C_1$ to $C_{30}$ halocarbyls and $C_1$ to $C_{30}$ substituted halocarbyls, and R' is selected from the group consisting of hydrogen, $C_1$ to $C_{30}$ hydrocarbyls, $C_1$ to $C_{30}$ substituted hydrocarbyls, $C_1$ to $C_{30}$ halocarbyls, and $C_1$ to $C_{30}$ substituted halocarbyls.

132. The catalyst system of claim 131 wherein the activator comprises an alumoxane.

133. The catalyst system of claim 131 wherein the activator comprises one or more of the following:
trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, di(isopropyl)ammonium tetraphenylborate, dicyclohexylammonium tetraphenylborate; tri(o-tolyl)phosphonium tetraphenylborate, tri(2,6-dimethylphenyl)phosphonium tetraphenylborate, trimethylammonium tetrakis(pentafluorophenyl)borate, triethylammonium tetrakis(pentafluorophenyl)borate, tripropylammonium tetrakis (pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis (pentafluorophenyl)borate, tropillium tetrakis (pentafluorophenyl)borate, triphenylcarbenium tetrakis (pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, di(isopropyl)ammonium tetrakis(pentafluorophenyl)borate, dicyclohexylammonium tetrakis(pentafluorophenyl) borate; tri(o-tolyl)phosphonium tetrakis(pentafluorophenyl)borate, tri(2,6-dimethylphenyl)phosphonium tetrakis(pentafluorophenyl)borate, trimethylammonium tetrakis-(2,3,4,6-tetrafluorophenyl)borate, triethylammonium tetrakis-(2,3,4,6-tetrafluorophenyl) borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl) borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, di(isopropyl)ammonium tetrakis(2,3,4,6-tetrafluorophenyl)borate, dicyclohexylammonium tetrakis(2,3,4,6-tetrafluorophenyl)borate; tri(o-tolyl)phosphonium tetrakis(2,3,4,6-tetrafluorophenyl)borate, tri(2,6-dimethylphenyl)phosphonium tetrakis(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri (t-butyl)ammonium tetrakis(perfluoronaphthyl)borate, N,N-dimethylanilinium tetrakis(perfluoronaphthyl)borate, N,N-diethylanilinium tetrakis(perfluoronaphthyl) borate, N,N-dimethyl-(2,4,6-trimethylanilinium)tetrakis(perfluoronaphthyl)borate, tropillium tetrakis (perfluoronaphthyl)borate, triphenylcarbenium tetrakis (perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, di(isopropyl)ammonium tetrakis(pentafluoronaphthyl)borate, dicyclohexylammonium tetrakis(pentafluoronaphthyl) borate; tri(o-tolyl)phosphonium tetrakis(pentafluoronaphthyl)borate, tri(2,6-dimethylphenyl)phosphonium tetrakis(pentafluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl) borate, N,N-dimethylanilinium tetrakis(perfluorobiphenyl)borate, N,N-diethylanilinium tetrakis (perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, di(isopropyl)ammonium tetrakis(pentafluorobiphenyl) borate, dicyclohexylammonium tetrakis(pentafluorobiphenyl)borate; tri(o-tolyl)phosphonium tetrakis(pentafluorobiphenyl)borate, tri(2,6-dimethylphenyl) phosphonium tetrakis(pentafluorobiphenyl)borate, trimethylammonium tetrakis(3,5-bis(trifluoromethyl) phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl) phenyl)borate, tri(t-butyl)ammonium tetrakis(3,5-bis(trifluoromethyl)phenyl)borate, N,N-dimethylanilinium tetrakis(3,5-bis(trifluoromethyl) phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl) phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, di(isopropyl) ammonium tetrakis(3,5-bis(trifluoromethyl)phenyl) borate, dicyclohexylammonium tetrakis(3,5-bis(trifluoromethyl)phenyl)borate; tri(o-tolyl) phosphonium tetrakis(3,5-bis(trifluoromethyl)phenyl) borate, and tri(2,6-dimethylphenyl)phosphonium tetrakis(3,5-bis(trifluoromethyl)phenyl)borate.

134. The catalyst system of claim 132 wherein the compound and/or activator are present on a support and the support comprises one or more of silica, alumina, silica-alumina, magnesia, titania, zirconia, magnesium chloride, montmorillonite, phyllosilicate, zeolites, talc, clays, silica-chromium, silica-titania, porous acrylic polymers, nanocomposites, aerogels, spherulites, or polymeric beads.

135. The catalyst system of claim 133 wherein the compound and/or activator are present on a support and the support comprises one or more of silica, alumina, silica-alumina, magnesia, titania, zirconia, magnesium chloride, montmorillonite, phyllosilicate, zeolites, talc, clays, silica-chromium, silica-titania, porous acrylic polymers, nanocomposites, aerogels, spherulites, or polymeric beads.

136. The catalyst system of claim 135 wherein the activator is bound to the support prior to combination with the transition metal catalyst compound.

137. A process to oligomerize an unsaturated monomer comprising contacting the monomer with the catalyst system of claim 120.

138. A process to oligomerize an unsaturated monomer comprising contacting the monomer with the catalyst system of claim 131.

139. A process to oligomerize an unsaturated monomer comprising contacting the monomer with the catalyst system of claim 132.

140. A process to oligomerize an unsaturated monomer comprising contacting the monomer with the catalyst system of claim 133.

141. A process to oligomerize an unsaturated monomer comprising contacting the monomer with the catalyst system of claim 134.

142. A process to oligomerize an unsaturated monomer comprising contacting the monomer with the catalyst system of claim 135.

143. A process to oligomerize an unsaturated monomer comprising contacting the monomer with the catalyst system of claim 136.

144. The process of claim 137 wherein the monomer comprises one or more alpha-olefins.

145. The process of claim 137 wherein the monomer comprises one or more C2 to C12 alpha-olefins.

146. A transition metal catalyst compound for oligomerization of an unsaturated monomer selected from the group consisting of

[bis(N-2,6-dimethylphenyl-2-aminoethyl)amine]cobalt dichloride,
[bis(N-2,4,6-trimethylphenyl-2-aminoethyl)amine]cobalt dichloride,
[bis(N-2,6-diisopropylphenyl-2-aminoethyl)amine]cobalt dichloride,
[bis(N-2,4,6-triisopropylphenyl-2-aminoethyl)amine]cobalt dichloride,
[bis(N-2,6-diisopropyl-4-methylphenyl-2-aminoethyl)amine]cobalt dichloride,
[bis(N-2,6-diethylphenyl-2-aminoethyl)amine]cobalt dichloride,
[bis(N-2,6-dimethylphenyl-2-aminoethyl)(2-picolyl)amine]cobalt dichloride,
[bis(N-2,4,6-trimethylphenyl-2-aminoethyl)(2-picolyl)amine]cobalt dichloride,
[bis(N-2,6-diisopropylphenyl-2-aminoethyl)(2-picolyl)amine]cobalt dichloride,
[bis(N-2,4,6-triisopropylphenyl-2-aminoethyl)(2-picolyl)amine]cobalt dichloride,
[bis(N-2,6-diisopropyl-4-methylphenyl-2-aminoethyl)(2-picolyl)amine]cobalt dichloride,
[bis(N-2,6-diethylphenyl-2-aminoethyl)(2-picolyl)amine]cobalt dichloride,
[bis(N-2,6-dimethylphenyl-2-aminoethyl)methylamine]cobalt dichloride,
[bis(N-2,4,6-trimethylphenyl-2-aminoethyl)methylamine]cobalt dichloride,
[bis(N-2,6-diisopropylphenyl-2-aminoethyl)methylamine]cobalt dichloride,
[bis(N-2,4,6-triisopropylphenyl-2-aminoethyl)methylamine]cobalt dichloride,
[bis(N-2,6-diisopropyl-4-methylphenyl-2-aminoethyl)methylamine]cobalt dichloride,
[bis(N-2,6-diethylphenyl-2-aminoethyl)methylamine]cobalt dichloride,
[bis(N-2,6-dimethylphenyl-2-aminoethyl)amine]cobalt dibromide,
[bis(N-2,4,6-trimethylphenyl-2-aminoethyl)amine]cobalt dibromide,
[bis(N-2,6-diisopropylphenyl-2-aminoethyl)amine]cobalt dibromide,
[bis(N-2,4,6-triisopropylphenyl-2-aminoethyl)amine]cobalt dibromide,
[bis(N-2,6-diisopropyl-4-methylphenyl-2-aminoethyl)amine]cobalt dibromide,
[bis(N-2,6-diethylphenyl-2-aminoethyl)amine]cobalt dibromide,
[bis(N-2,6-dimethylphenyl-2-aminoethyl)(2-picolyl)amine]cobalt dibromide,
[bis(N-2,4,6-trimethylphenyl-2-aminoethyl)(2-picolyl)amine]cobalt dibromide,
[bis(N-2,6-diisopropylphenyl-2-aminoethyl)(2-picolyl)amine]cobalt dibromide,
[bis(N-2,4,6-triisopropylphenyl-2-aminoethyl)(2-picolyl)amine]cobalt dibromide,
[bis(N-2,6-diisopropyl-4-methylphenyl-2-aminoethyl)(2-picolyl)amine]cobalt dibromide,
[bis(N-2,6-diethylphenyl-2-aminoethyl)(2-picolyl)amine]cobalt dibromide,
[bis(N-2,6-dimethylphenyl-2-aminoethyl)methylamine]cobalt dibromide,
[bis(N-2,4,6-trimethylphenyl-2-aminoethyl)methylamine]cobalt dibromide,
[bis(N-2,6-diisopropylphenyl-2-aminoethyl)methylamine]cobalt dibromide,
[bis(N-2,4,6-triisopropylphenyl-2-aminoethyl)methylamine]cobalt dibromide,
[bis(N-2,6-diisopropyl-4-methylphenyl-2-aminoethyl)methylamine]cobalt dibromide,
[bis(N-2,6-diethylphenyl-2-aminoethyl)methylamine]cobalt dibromide,
[bis(N-2,6-dimethylphenyl-2-aminoethyl)amine]cobalt dimethyl,
[bis(N-2,4,6-trimethylphenyl-2-aminoethyl)amine]cobalt dimethyl,
[bis(N-2,6-diisopropylphenyl-2-aminoethyl)amine]cobalt dimethyl,
[bis(N-2,4,6-triisopropylphenyl-2-aminoethyl)amine]cobalt dimethyl,
[bis(N-2,6-diisopropyl-4-methylphenyl-2-aminoethyl)amine]cobalt dimethyl,
[bis(N-2,6-diethylphenyl-2-aminoethyl)amine]cobalt dimethyl,
[bis(N-2,6-dimethylphenyl-2-aminoethyl)methylamine]cobalt dimethyl,
[bis(N-2,4,6-trimethylphenyl-2-aminoethyl)methylamine]cobalt dimethyl,
[bis(N-2,6-diisopropylphenyl-2-aminoethyl)methylamine]cobalt dimethyl,
[bis(N-2,4,6-triisopropylphenyl-2-aminoethyl)methylamine]cobalt dimethyl,
[bis(N-2,6-diisopropyl-4-methylphenyl-2-aminoethyl)methylamine]cobalt dimethyl,
[bis(N-2,6-diethylphenyl-2-aminoethyl)methylamine]cobalt dimethyl,
[bis(N-2,6-dimethylphenyl-2-aminoethyl)(2-picolyl)amine]cobalt dimethyl,
[bis(N-2,4,6-trimethylphenyl-2-aminoethyl)(2-picolyl)amine]cobalt dimethyl,
[bis(N-2,6-diisopropylphenyl-2-aminoethyl)(2-picolyl)amine]cobalt dimethyl,
[bis(N-2,4,6-triisopropylphenyl-2-aminoethyl)(2-picolyl)amine]cobalt dimethyl,
[bis(N-2,6-diisopropyl-4-methylphenyl-2-aminoethyl)(2-picolyl)amine]cobalt dimethyl,
[bis(N-2,6-diethylphenyl-2-aminoethyl)(2-picolyl)amine]cobalt dimethyl,
[bis(N-2,6-dimethylphenyl-2-aminoethyl)amine]iron dichloride,
[bis(N-2,4,6-trimethylphenyl-2-aminoethyl)amine]iron dichloride,
[bis(N-2,6-diisopropylphenyl-2-aminoethyl)amine]iron dichloride,
[bis(N-2,4,6-triisopropylphenyl-2-aminoethyl)amine]iron dichloride,
[bis(N-2,6-diisopropyl-4-methylphenyl-2-aminoethyl)amine]iron dichloride,
[bis(N-2,6-diethylphenyl-2-aminoethyl)amine]iron dichloride,

[bis(N-2,6-dimethylphenyl-2-aminoethyl)methylamine] iron dichloride,
[bis(N-2,4,6-trimethylphenyl-2-aminoethyl)methylamine]iron dichloride,
[bis(N-2,6-diisopropylphenyl-2-aminoethyl)methylamine]iron dichloride,
[bis(N-2,4,6-triisopropylphenyl-2-aminoethyl)methylamine]iron dichloride,
[bis(N-2,6-diisopropyl-4-methylphenyl-2-aminoethyl)methylamine]iron dichloride,
[bis(N-2,6-diethylphenyl-2-aminoethyl)methylamine] iron dichloride,
[bis(N-2,6-dimethylphenyl-2-aminoethyl)(2-picolyl)amine]iron dichloride,
[bis(N-2,4,6-trimethylphenyl-2-aminoethyl)(2-picolyl)amine]iron dichloride,
[bis(N-2,6-diisopropylphenyl-2-aminoethyl)(2-picolyl)amine]iron dichloride,
[bis(N-2,4,6-triisopropylphenyl-2-aminoethyl)(2-picolyl)amine]iron dichloride,
[bis(N-2,6-diisopropyl-4-methylphenyl-2-aminoethyl)(2-picolyl)amine]iron dichloride,
[bis(N-2,6-diethylphenyl-2-aminoethyl)(2-picolyl)amine]iron dichloride,
[bis(N-2,6-dimethylphenyl-2-aminoethyl)amine]manganese dichloride,
[bis(N-2,4,6-trimethylphenyl-2-aminoethyl)amine]manganese dichloride,
[bis(N-2,6-diisopropylphenyl-2-aminoethyl)amine]manganese dichloride,
[bis(N-2,4,6-triisopropylphenyl-2-aminoethyl)amine] manganese dichloride,
[bis(N-2,6-diisopropyl-4-methylphenyl-2-aminoethyl)amine]manganese dichloride,
[bis(N-2,6-diethylphenyl-2-aminoethyl)methylamine] manganese dichloride,
[bis(N-2,6-dimethylphenyl-2-aminoethyl)methylamine] manganese dichloride,
[bis(N-2,4,6-trimethylphenyl-2-aminoethyl)methylamine]manganese dichloride,
[bis(N-2,6-diisopropylphenyl-2-aminoethyl)methylamine]manganese dichloride,
[bis(N-2,4,6-triisopropylphenyl-2-aminoethyl)methylamine]manganese dichloride,
[bis(N-2,6-diisopropyl-4-methylphenyl-2-aminoethyl)methylamine]manganese dichloride,
[bis(N-2,6-diethylphenyl-2-aminoethyl)methylamine] manganese dichloride,
[bis(N-2,6-diethylphenyl-2-aminoethyl)(2-picolyl)amine]manganese dichloride,
[bis(N-2,4,6-triethylphenyl-2-aminoethyl)(2-picolyl)amine]manganese dichloride,
[bis(N-2,6-dimethylphenyl-2-aminoethyl)(2-picolyl)amine]manganese dichloride,
[bis(N-2,4,6-trimethylphenyl-2-aminoethyl)(2-picolyl)amine]manganese dichloride,
[bis(N-2,6-diisopropylphenyl-2-aminoethyl)(2-picolyl)amine]manganese dichloride,
[bis(N-2,4,6-triisopropylphenyl-2-aminoethyl)(2-picolyl)amine]manganese dichloride,
[bis(N-2,6-diisopropyl-4-methylphenyl-2-aminoethyl)(2-picolyl)amine]manganese dichloride,
[bis(N-2,6-diethylphenyl-2-aminoethyl)(2-picolyl)amine]manganese dichloride,
[bis(N-2,6-dimethylphenyl-2-aminoethyl)amine]nickel dichloride,
[bis(N-2,4,6-trimethylphenyl-2-aminoethyl)amine]nickel dichloride,
[bis(N-2,6-diisopropylphenyl-2-aminoethyl)amine]nickel dichloride,
[bis(N-2,4,6-triisopropylphenyl-2-aminoethyl)amine] nickel dichloride,
[bis(N-2,6-diisopropyl-4-methylphenyl-2-aminoethyl)amine]nickel dichloride,
[bis(N-2,6-diethylphenyl-2-aminoethyl)amine]nickel dichloride,
[bis(N-2,6-dimethylphenyl-2-aminoethyl)methylamine] nickel dichloride,
[bis(N-2,4,6-trimethylphenyl-2-aminoethyl)methylamine]nickel dichloride,
[bis(N-2,6-diisopropylphenyl-2-aminoethyl)methylamine]nickel dichloride,
[bis(N-2,4,6-triisopropylphenyl-2-aminoethyl)methylamine]nickel dichloride,
[bis(N-2,6-diisopropyl-4-methylphenyl-2-aminoethyl)methylamine]nickel dichloride,
[bis(N-2,6-diethylphenyl-2-aminoethyl)methylamine] nickel dichloride,
[bis(N-2,6-dimethylphenyl-2-aminoethyl)(2-picolyl)amine]nickel dichloride,
[bis(N-2,4,6-trimethylphenyl-2-aminoethyl)(2-picolyl)amine]nickel dichloride,
[bis(N-2,6-diisopropylphenyl-2-aminoethyl)(2-picolyl)amine]nickel dichloride,
[bis(N-2,4,6-triisopropylphenyl-2-aminoethyl)(2-picolyl)amine]nickel dichloride,
[bis(N-2,6-diisopropyl-4-methylphenyl-2-aminoethyl)(2-picolyl)amine]nickel dichloride, and
[bis(N-2,6-diethylphenyl-2-aminoethyl)(2-picolyl)amine]nickel dichloride.

147. A catalyst system comprising the compound of claim 146 and an activator.

148. The catalyst system of claim 147 wherein the activator comprises an alumoxane.

149. The catalyst system of claim 147 wherein the activator comprises an alkyl aluminum compound.

150. The catalyst system of claim 147 wherein the activator comprises an ionizing or stoichiometric activator.

151. The catalyst system of claim 147 wherein the activator comprises one or more of:
trimethylammonium tetraphenylborate, triethylammonium tetraphenylborate, tripropylammonium tetraphenylborate, tri(n-butyl)ammonium tetraphenylborate, tri (t-butyl)ammonium tetraphenylborate, N,N-dimethylanilinium tetraphenylborate, N,N-diethylanilinium tetraphenylborate, N,N-dimethyl-(2, 4,6-trimethylanilinium)tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, di(isopropyl)ammonium tetraphenylborate, dicyclohexylammonium tetraphenylborate; tri(o-tolyl)phosphonium tetraphenylborate, tri(2,6-dimethylphenyl)phosphonium tetraphenylborate, trimethylammonium tetrakis(pentafluorophenyl) borate, triethylammonium tetrakis(pentafluorophenyl) borate, tripropylammonium tetrakis (pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis (pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, di(isopropyl)ammonium tetrakis(pentafluorophenyl)borate, dicyclohexylammonium tetrakis(pentafluorophenyl)borate; tri(o-tolyl)phosphonium tetrakis(pentafluorophenyl)borate, tri(2,6-dimethylphenyl)phosphonium tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, di(isopropyl)ammonium tetrakis(2,3,4,6-tetrafluorophenyl)borate, dicyclohexylammonium tetrakis(2,3,4,6-tetrafluorophenyl)borate; tri(o-tolyl)phosphonium tetrakis(2,3,4,6-tetrafluorophenyl)borate, tri(2,6-dimethylphenyl)phosphonium tetrakis(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, di(isopropyl)ammonium tetrakis(pentafluoronaphthyl)borate, dicyclohexylammonium tetrakis(pentafluoronaphthyl)borate; tri(o-tolyl)phosphonium tetrakis(pentafluoronaphthyl)borate, tri(2,6-dimethylphenyl)phosphonium tetrakis(pentafluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, di(isopropyl)ammonium tetrakis(pentafluorobiphenyl)borate, dicyclohexylammonium tetrakis(pentafluorobiphenyl)borate; tri(o-tolyl)phosphonium tetrakis(pentafluorobiphenyl)borate, tri(2,6-dimethylphenyl)phosphonium tetrakis(pentafluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, di(isopropyl)ammonium tetrakis(3,5-bis(trifluoromethyl)phenyl)borate, dicyclohexylammonium tetrakis(3,5-bis(trifluoromethyl)phenyl)borate; tri(o-tolyl)phosphonium tetrakis(3,5-bis(trifluoromethyl)phenyl)borate, and tri(2,6-dimethylphenyl)phosphonium tetrakis(3,5-bis(trifluoromethyl)phenyl)borate.

152. The catalyst system of claim 147 wherein the compound and/or the activator is present on a support.

153. The catalyst system of claim 151 wherein the compound and/or the activator is present on a support.

154. The catalyst system of claim 153 wherein the support comprises one or more Group 2, 3, 4, 5, 13 or 14 metal oxides.

155. The catalyst system of claim 153 the support comprises one or more of silica, alumina, silica-alumina, magnesia, titania, zirconia, magnesium chloride, montmorillonite, phyllosilicate, zeolites, talc, clays, silica-chromium, silica-titania, porous acrylic polymers, nanocomposites, aerogels, spherulites, or polymeric beads.

156. The catalyst system of claim 153 the support is silica.

157. The catalyst system of claim 153 the activator is bound to the support prior to combination with the transition metal catalyst compound.

158. The catalyst system of claim 152 the activator comprises an alkyl aluminum compound and the support comprises one or more of silica, alumina, silica-alumina, magnesia, titania, zirconia, magnesium chloride, montmorillonite, phyllosilicate, zeolites, talc, clays, silica-chromium, silica-titania, porous acrylic polymers, nanocomposites, aerogels, spherulites, or polymeric beads.

159. A process to polymerize an unsaturated monomer comprising contacting the monomer with the catalyst system of claim 147.

160. The process of claim 154 wherein the monomer comprises one or more alpha-olefins.

161. The process of claim 154 wherein the monomer comprises one or more $C_2$ to $C_{40}$ alpha-olefins.

162. The process of claim 154 wherein the monomer comprises one or more C2 to C12 alpha-olefins.

163. The process of claim 154 wherein the monomer further comprises one or more dienes.

* * * * *